United States Patent
Mangold et al.

(10) Patent No.: US 12,122,748 B2
(45) Date of Patent: Oct. 22, 2024

(54) OPTICAL DATA COMMUNICATION SYSTEM COMPRISING PARA-PHENYLENEVINYLENES AND SPECIFIC PARA-PHENYLENEVINYLENES

(71) Applicant: BASF SE, Ludwigshafen am Rhein (DE)

(72) Inventors: Hannah Stephanie Mangold, Ludwigshafen (DE); Martin Koenemann, Ludwigshafen (DE); Sorin Ivanovici, Ludwigshafen (DE); Michael Kuehn, Ludwigshafen (DE)

(73) Assignee: BASF SE (DE)

( * ) Notice: Subject to any disclaimer, the term of this patent is extended or adjusted under 35 U.S.C. 154(b) by 823 days.

(21) Appl. No.: 16/973,648

(22) PCT Filed: Jun. 6, 2019

(86) PCT No.: PCT/EP2019/064834
§ 371 (c)(1),
(2) Date: Dec. 9, 2020

(87) PCT Pub. No.: WO2019/238532
PCT Pub. Date: Dec. 19, 2019

(65) Prior Publication Data
US 2021/0284608 A1 Sep. 16, 2021

(30) Foreign Application Priority Data
Jun. 11, 2018 (EP) .................................. 18177027

(51) Int. Cl.
*C07D 209/86* (2006.01)
*C07C 1/34* (2006.01)
(Continued)

(52) U.S. Cl.
CPC .............. *C07D 209/86* (2013.01); *C07C 1/34* (2013.01); *C07C 209/68* (2013.01);
(Continued)

(58) Field of Classification Search
CPC ........ C07D 209/86; C07C 1/34; C07C 209/68; C07C 253/30; C09K 11/06;
(Continued)

(56) References Cited

U.S. PATENT DOCUMENTS 2,551,731 A  5/1951  Drewitt et al.
6,267,913 B1  7/2001  Marder et al.
(Continued)

FOREIGN PATENT DOCUMENTS

DE   2 262 531        8/1973
EP   1 858 179 A1    11/2007
(Continued)

OTHER PUBLICATIONS

International Search Report issued on Jul. 24, 2019 in PCT/EP2019/064834 filed on Jun. 6, 2019.
(Continued)

*Primary Examiner* — Caleen O Sullivan
(74) *Attorney, Agent, or Firm* — Faegre Drinker Biddle & Reath LLP

(57) ABSTRACT

An optical data communication system may include one or more para-phenylenevinylenes, a receiver for an optical data communication system comprising para-phenylenevinylene(s), a transmitter for an optical data communication system comprising para-phenylenevinylene(s), the use of para-phenylenevinylene(s) in an optical data communication system, specific para-phenylenevinylene(s) and their preparation.

17 Claims, 1 Drawing Sheet

(51) Int. Cl.
    C07C 209/68    (2006.01)
    C07C 253/30    (2006.01)
    C09K 11/06    (2006.01)
    H04B 10/50    (2013.01)
    H04B 10/60    (2013.01)
    H10K 85/60    (2023.01)

(52) U.S. Cl.
    CPC ............ *C07C 253/30* (2013.01); *C09K 11/06* (2013.01); *H04B 10/502* (2013.01); *H04B 10/60* (2013.01); *H10K 85/60* (2023.02); *H10K 85/615* (2023.02); *H10K 85/626* (2023.02); *H10K 85/6572* (2023.02); *C09K 2211/1007* (2013.01); *C09K 2211/1011* (2013.01); *C09K 2211/1018* (2013.01)

(58) Field of Classification Search
    CPC .... C09K 2211/1007; C09K 2211/1011; C09K 2211/1018; H04B 10/502; H04B 10/60; H10K 85/60; H10K 85/615; H10K 85/626; H10K 85/6572; H10K 85/115
    USPC ............................ 430/7, 270.1, 271.1, 272.1
    See application file for complete search history.

(56) References Cited

U.S. PATENT DOCUMENTS

| | | |
|---|---|---|
| 2002/0185634 A1 | 12/2002 | Marder et al. |
| 2003/0091859 A1 | 5/2003 | Cho et al. |
| 2005/0249248 A1 | 11/2005 | He et al. |
| 2006/0056855 A1 | 3/2006 | Nakagawa et al. |
| 2009/0034561 A1 | 2/2009 | He et al. |
| 2009/0206520 A1 | 8/2009 | Park |
| 2009/0297156 A1 | 12/2009 | Nakagawa et al. |
| 2009/0297157 A1 | 12/2009 | Nakagawa |
| 2009/0297166 A1 | 12/2009 | Nakagawa et al. |
| 2009/0297167 A1 | 12/2009 | Nakagawa et al. |
| 2009/0310976 A1 | 12/2009 | Nakagawa et al. |
| 2010/0066241 A1 | 3/2010 | Cho et al. |
| 2010/0323298 A1 | 12/2010 | Park |
| 2011/0282020 A1 | 11/2011 | Sipos |
| 2011/0306804 A1 | 12/2011 | Cortright |
| 2014/0336349 A1 | 11/2014 | Sipos et al. |
| 2017/0075191 A1 | 3/2017 | Tiecke et al. |
| 2017/0346556 A1 | 11/2017 | Tiecke et al. |

FOREIGN PATENT DOCUMENTS

| | | | |
|---|---|---|---|
| EP | 2 138 551 A2 | 12/2009 | |
| WO | WO 2010/132740 A2 | 11/2010 | |
| WO | WO 2011/043660 A2 | 4/2011 | |
| WO | WO 2011/043661 A1 | 4/2011 | |
| WO | WO 2011/093603 A1 | 8/2011 | |
| WO | WO 2015/137804 A1 | 9/2015 | |

OTHER PUBLICATIONS

International Preliminary Report on Patentability issued on Sep. 25, 2020 in PCT/EP2019/064834 filed on Jun. 6, 2019.

Written Opinion of the International Preliminary Examining Authority issued on Jun. 9, 2020 in PCT/EP2019/064834 filed on Jun. 6, 2019.

Zhang, X. et al., "Synthesis of carbazole derivatives with high quantum yield and high glass transition temperature," Optical Materials, vol. 32, 2009, pp. 94-98, XP055536318.

Lee, K. H. et al., "Blue electroluminescent materials based on 2,7-distyrylfluorene for organic light-emitting diodes," Thin Solid Films, vol. 518, 2010, pp. 5091-5097, XP055535622.

Yanez, C. O. et al., "Photosensitive Polymeric Materials for Two-Photon 3D Worm Optical Data Storage Systems," ACS Applied Materials & Interfaces, vol. 1, No. 10, 2009, pp. 2219-2229, XP055535660.

Sajjad, M. T. et al., "Novel Fast Color-Converter for Visible Light Communication Using a Blend of Conjugated Polymers," ACS Photonics, vol. 2, 2015, pp. 194-199, XP055535670.

Wang, H. et al., "A highly luminescent organic crystal with the well-balanced charge transport property: The role of cyano-substitution in the terminal phenyl unit of distyrylbenzene," Organic Electronics, vol. 28, 2015, pp. 287-293, XP029346622.

Zheng, Z. et al., "Theory and experiment studies of the 1,4-bis(4-methoxylstyryl)benzene as a wavelength shifter of liquid scintillator," Journal of Luminescence, vol. 183, 2016, pp. 1-6, XP029859389.

Gruzinskii, V. et al., "Spectral Luminescent and Generation Properties of New Active Media in the Blue Region of the Spectrum," Zhurnal Prikladnoi Spektroskopii, vol. 46, No. 1, 1987, pp. 40-44, XP009055695.

Chun et al., "Visible Light Communication using a Blue GaN (Mue)LED and Fluorescent Polymer Colour Converter," available online at <https://pure.strath.ac.uk/portal/files/44580356/Chun_etal_IEEE_PTL_2015_Visible_light_communication_using_a_blue_GaN_uLED_and_fluorescent.pdf>, 4 pages.

Collins et al., "High gain, wide field of view concentrator for optical communications," Optics Letters, vol. 39, No. 7, Apr. 1, 2014, pp. 1756-1759.

Dimitrov et al., "Principles of LED light communications", Cambridge University Press 2015, Chapter 2.1 to Chapter 2.4.

Elgala et al., "Indoor optical wireless communication: Potential and state-of-the-art," Topics in Optical Communications, Article in IEEE Communications Magazine, Oct. 2011, pp. 56-62.

Manousiadis et al., "Wide field-of-view fluorescent antenna for visible light communications beyond the 6tendue limit," Optica., vol. 3, No. 7, Jul. 2016, pp. 702-706.

Mulyawan et al., "MIMO Visible Light Communications Using a Wide Field-of-View Fluorescent Concentrator," IEEE Photonics Technology Letters, vol. 29, No. 3, Feb. 1, 2017, pp. 306-309.

Peyronel et al., "Luminescent detector for free-space optical communication," Optica., vol. 3, No. 7, Jul. 2016, pp. 787-792.

Sajad et al., "A saturated red color converter for visible light communication using a blend of starshaped organic semiconductors," Appl. Phys. Lett., vol. 110, 013302, 2017, 5 pages.

Sajjad et al., "Fluorescent Red-Emitting BODIPY Oligofl uorene Star-Shaped Molecules as a Color Converter Material for Visible Light Communications," Adv. Optical Mater., vol. 3, 2015, pp. 536-540.

Wang et al., "Postfunctionalization of BN-Embedded Polycyclic Aromatic Compounds for Fine-Tuning of Their Molecular Properties," Chemistry a European Journal, vol. 21, 2015, pp. 8867-8873.

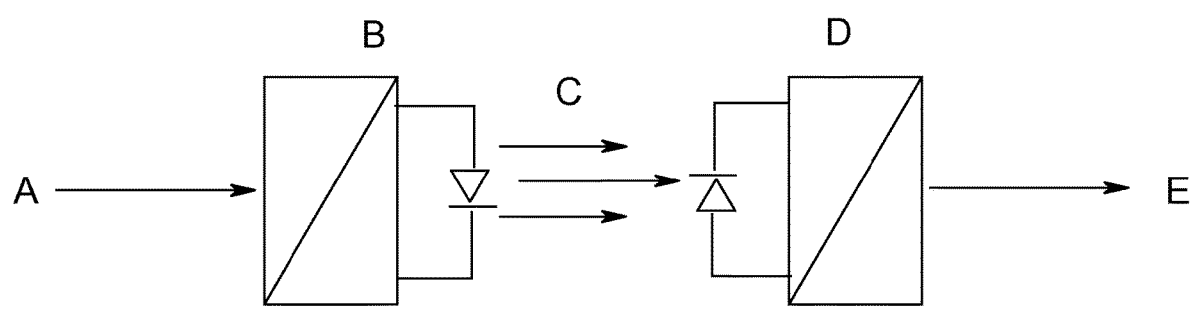

OPTICAL DATA COMMUNICATION SYSTEM COMPRISING PARA-PHENYLENEVINYLENES AND SPECIFIC PARA-PHENYLENEVINYLENES

The present invention relates to an optical data communication system comprising para-phenylenevinylenes, a receiver for an optical data communication system comprising para-phenylenevinylenes, a transmitter for an optical data communication system comprising para-phenylenevinylenes, the use of para-phenylenevinylenes in an optical data communication system, specific para-phenylenevinylenes and their preparation.

BACKGROUND OF THE INVENTION

Optical data communication, especially optical wireless communication (OWC) like visible Light Communication (VLC), free space optical communication (FSO) and Li-Fi (Light Fidelity) are rapid growing technological fields that aim to implement fast and safe wireless communication to replace or complement existing wireless technologies. New technologies like the internet of things (being the basis for industry 4.0, IP 4.0®, etc.), wearables (i.e. smart electronic devices with microcontrollers that can be worn on the body as implant or accessories) and the general increase in mobile communication lead to a rapid increase in data streams and the necessity for new communication channels. In optical data communication systems generally an electrical signal is transformed to an optical signal in a transmitter. The optical light source is usually either a light-emitting diode (LED) or a laser diode (LD). The modulated optical field then propagates through a free-space path before arriving at a receiver. In the receiver, the optical signal is transformed back to an electrical signal.

Li-Fi is the term established for the transmission of data through illumination using LED lighting that varies in its intensity for high speed wireless communication. Together with the widespread use of LED lighting in offices, streetlights and homes, Li-Fi is an added benefit to the existing lighting infrastructure.

One common approach for LED illumination is to use phosphor converted white LEDs. Di-, tri- and tetrachromatic methods are adopted to optimize the wavelength for producing white light in phosphor converted white LEDs.

In said LEDs usually a blue LED, for example InGaN, is coated with a yellow phosphor as a frequency (color) converter so that a fraction of the blue light is absorbed and re-emitted at longer wavelength to give a two-color white (dichromatic mode).

Alternatively, white-light LEDs can be created by a mix of the colors red, green and blue. In this case for example an UV LED is coated with a red, a green and a blue phosphor (trichromatic mode).

It is also known to generate white light based on LEDs in tetrachromatic mode, generally by combining the colors blue, cyan, green and red (four-color white). In this case for example a blue LED and a red LED is coated with a cyan and a green phosphor.

Organic compounds that can be used inter alia as frequency converters in remote phosphor LEDs offer many potential advantages for OWC, especially for VLC, respectively Li-Fi, due to their visible band gaps, short radiative lifetime, and high photoluminescence quantum yield (PLQY). Actually, light emitting diodes (LEDs) are replacing existing lighting sources to an ever increasing extent.

A key problem that still needs to be solved is the slow response of commercial white LEDs. So far, there exists no LED which can emit white light directly. White-light LEDs can be created from light-emitting LED chips (emission wavelength depend on the mode—di-, tri- or tetrachromatic) coated or covered with one or more luminescent materials as a frequency (color) converter (phosphor) (as mentioned above). According to this concept, the luminescent material is applied directly and without intervening space to the LED light source (LED chip). This concept is also referred to as "phosphor on a chip". In phosphor on a chip LEDs, the luminescent material used is generally an inorganic material that absorbs part of the LED emission and reemits a broad spectrum. Often LEDs of this type generate cool white light (i.e. they have a correlated color temperature CCT of greater than 6 000 K) and their average color rendering index CRI is low, usually about 70 to 85.

To provide a more pleasing and natural white light having a CCT of below 6 000 K, a different concept may be used. According to this concept, the luminescent material is dissolved or dispersed in a polymeric matrix which is at a certain distance from the emitting LED chip. This structure is referred to as "remote phosphor".

However, the photoluminescence lifetime (fluorescent/phosphorescent lifetime or excited-state lifetime) of conventional phosphors is too long (ranging in the order of greater than 10 nanoseconds and up to some microseconds) to support high rates of data transmission. To transmit data via LED lighting the IEEE 802.15.7-2011 standard specifies optical clock frequencies up to 120 Mhz, which requires on-off times of the LEDs in the order of nanoseconds. To be fast enough for data transmission another option is to use only the blue LED emission and filter out the other wavelengths converted by the phosphors with too long fluorescent lifetimes. As only a small amount (typically about 6%) of the energy is in the blue part of the spectrum these systems are limited in range. First commercial Li-Fi products that enable a wireless network through a bidirectional line, like the Lucibel Li-Fi system, are already available but still need remarkable improvement.

H. Chun et al. describe in their online article with the title "Visible Light Communication using a Blue GaN μLED and Fluorescent Polymer Colour Converter" (https://pure.strath.ac.uk/portal/files/44580356/Chun_etal_IEEE_PTL_2015_Visible_light_comm unication_using_a_blue_GaN_uLED_and_fluorescent.pdf) a novel technique to achieve high-speed visible light communication using white light generated by a blue GaN μLED and a yellow fluorescent copolymer. By this technique the ratio between the blue electroluminescence of the μLED and the yellow photoluminescence of the copolymer frequency converter is improved.

M. T. Sajjad et al. describe in Adv. Optical Mater. 2015, 3, 536-540 fluorescent red-emitting boron dipyrromethene (BODIPY)-oligofluorene star-shaped molecules as a frequency converter material for VLC.

M. T. Sajjad et al. describe in Appl. Phys. Lett. 110, 013302 (2017) a saturated red frequency converter for visible light communication using a blend of starshaped organic semiconductors. M. T. Sajjad et al. describe in their online published article "A novel fast color-converter for visible light communication using a blend of conjugated polymers" (https://pure.strath.ac.uk/portal/files/41605644/Sajjad_etal_ACS_Photonics_2015_Novel_fast_co lor_converter_for_visible_light_communication.pdf) to use a blend of semiconducting polymers, in particular the highly fluorescent green emitting poly[2,5-bis(2/,5/-bis(2//-ethylhexyloxy)phenyl)-p-phenylenevinylene) (BBEHP-PPV) and the orange-red emitting poly[2-methoxy-5-(2-ethyl-hexyloxy)-1,4-phenylene-vinylene] (MEH-PPV) as fast color-converters to replace commercial phosphors in hybrid LEDs for visible light communication. It was possible to achieve a broadband, balanced frequency converter with a very high modulation bandwidth to replace commercial phosphors in hybrid LEDs for visible light communications. The resulting frequency converter exploits partial Forster energy transfer from green-emitting BBEHP-PPV to orange-red emitting MEH-PPV. The achieved 3 dB modulation bandwidth (electrical-electrical) was 40 times higher than with commercially available phosphor LEDs, and 5 times higher than with the afore-mentioned red-emitting organic frequency converters.

On the receiver side of an OWC system, semiconductor photodiodes are commonly used as optical detectors at high frequencies. However, the response times of these diodes are limited by the junction capacitance and the carrier transit time, and scale with detector size. In T. G. Tiecke et al., Optica, Vol. 3, No. 7, July 2016, 787-792, a method to increase the effective area and field of view of an optical receiver while maintaining fast response times is presented. This is achieved by using optical waveguides doped with wavelength shifting dyes (luminous concentrators). The incident light, modulated with a communication signal, is absorbed by the dye molecules independently of the light incidence angle and subsequently re-emitted at a different wavelength. A portion of the emitted light is collected by the fiber and guided to a small area semiconductor photodiode. It is referred to the combined system of the luminescent concentrators and photodiode as a luminescent detector (LD). However, in T. G. Tiecke et al., no specific wavelength shifting dyes are mentioned.

US 2017/0346556 A discloses an apparatus comprising: a wavelength-shifting element configured to receive an input-light signal, wherein the wavelength-shifting element comprises a wavelength-shifting material configured to: absorb at least a portion of the received input-light signal; and produce an emitted-light signal from the absorbed portion of the received input-light signal; a plasmonic grating comprising a plurality of plasmonic-structure elements, the plasmonic grating configured to: receive at least a portion of the emitted-light signal; and direct the received portion of the emitted-light signal toward a photodetector; and the photodetector configured to: receive the directed portion of the emitted-light signal; and produce an electrical current corresponding to the directed portion of the emitted-light signal. As an example for a wave-length-shifting material, the inorganic materials cadmium/selenide/cadmium sulfide (CdSe/CdS) quantum dots and lead selenide/led sulfide (PdSe/PdS) quantum dots are mentioned.

However, the photoluminescence lifetime (fluorescent/phosphorescent lifetime or excited-state lifetime) of conventional phosphors as wavelength-shifting material is too long (ranging in the order of greater than 10 nanoseconds and up to some microseconds) to support high rates of data transmission.

There is therefore a great demand in phosphors that have luminescent, especially fluorescent lifetimes in the order of a few nanoseconds and preferably even lower while maintaining good emission efficiency.

Further—in the case of using the phosphors in the transmitter of an optical data communication system—it should at the same time be possible to provide a lighting device having a good color reproduction and color temperature. Preferably, the lighting device should have a CCT (correlated color temperature) below 6500 K and an average color rendering index CRI greater than 80, even better higher than 90.

It is therefore an object of the present invention to provide organic luminescent, especially fluorescent, compounds having short luminescent, especially fluorescent lifetimes for use in optical data communication systems. The organic luminescent, especially fluorescent, compounds should especially be useful in the transmitter and/or the receiver of the optical data communication system, preferably emitting or receiving electromagnetic radiation in the visible spectral range having short excited-state lifetimes and preferably—when used in the transmitter—a good color reproduction rendering and/or color temperature.

Preferably, the organic luminescent, especially fluorescent, compounds should also have one or more of the following characteristics:
- short excited-state lifetimes in the order of a few nanoseconds;
- high light stability, especially under blue light and/or white light irradiation conditions;
- high heat stability, especially under blue light and/or white light irradiation conditions;
- high chemical stability with respect to moisture and oxygen;
- high luminescence quantum yield (QY).

It has been found that the afore-mentioned objects are solved by an optical data communication system comprising para-phenylenevinylenes of formula (I), and a receiver respectively a transmitter for an optical data communication system comprising said para-phenylenevinylenes.

SUMMARY OF THE INVENTION

The present invention relates to an optical data communication system comprising at least one compound of formula (I)

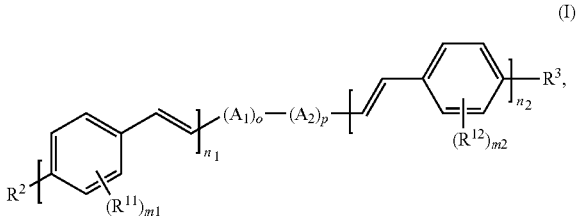

wherein
n1 and n2 are each independently 1, 2 or 3, preferably 1 or 2,
m1 and m2 are each independently 0, 1, 2, 3 or 4, preferably 0, 1 or 2, and
$R^{11}$ and $R^{12}$ are each independently H, unsubstituted or substituted $C_1$-$C_{20}$alkyl or $C_1$-$C_{20}$alkoxy, $C_6$-$C_{30}$aryl or $C_7$-$C_{31}$alkaryl, preferably H, unsubstituted or substituted $C_1$-$C_{20}$alkyl or unsubstituted or substituted $C_1$-$C_{20}$alkoxy,
$R^2$ and $R^3$ are each independently hydrogen, unsubstituted or substituted $C_1$-$C_{20}$alkyl, unsubstituted or substituted $C_2$-$C_{20}$alkenyl, unsubstituted or substituted $C_1$-$C_{20}$alkoxy, unsubstituted or substituted $C_3$-$C_{20}$cycloalkyl, unsubstituted or substituted $C_6$-$C_{24}$aryl, an aliphatic heterocycle having an unsubstituted or substituted ring formed of 3 to 24 atoms; unsubstituted or substituted heteroaryl having a ring formed of 3 to 24 atoms; amino, CN, $CF_3$, $COOC_1$-$C_{20}$alkyl, $OCOC_1$-$C_{20}$alkyl or unsubstituted or substituted $C_7$-$C_{31}$alkaryl, $A_2$ is

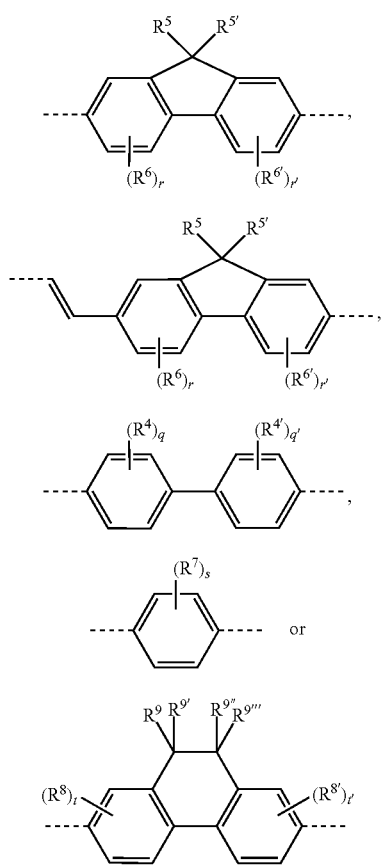

$A_1$ is

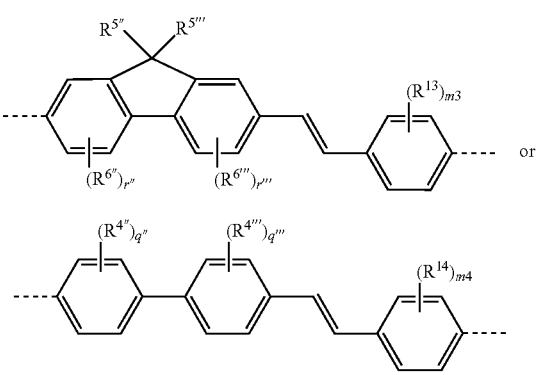

p is 1 or 2, preferably 1, o is 0, 1 or 2, q, q', q", q''', s, m3 and m4 are each independently 0, 1, 2, 3 or 4, preferably 0, 1 or 2, r, r', r", r''', t and t' are each independently 0, 1, 2 or 3, preferably 0, 1 or 2, $R^4$, $R^{4'}$, $R^{4''}$, $R^{4'''}$, $R^6$, $R^{6'}$, $R^{6''}$, $R^{6'''}$, $R^7$, $R^8$, $R^{8'}$, $R^{13}$ and $R^{14}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl, $R^5$, $R^{5'}$, $R^{5''}$, $R^{5'''}$, $R^9$, $R^{9'}$, $R^{9''}$ and $R^{9'''}$ are each independently H or unsubstituted or substituted $C_1$-$C_{20}$alkyl, unsubstituted or substituted $C_6$-$C_{30}$aryl or unsubstituted or substituted $C_7$-$C_{31}$alkaryl, wherein the dotted lines are bonding sites.

The present invention further relates to a receiver and a transmitter for an optical data communication system comprising at least one compound of formula (I) and the use of a compound of formula (I) in an optical data communication system.

A further aspect of the invention relates to specific novel compounds of formula (I) and their preparation.

DESCRIPTION OF THE INVENTION

In the context of the present invention, the term "luminescent compound(s)" is also referred to as phosphor(s). The luminescent compounds may be inorganic or organic compounds.

Accordingly, in the context of the present invention, the terms "phosphor" and "luminescent compound(s)" are used interchangeably to describe a luminescent material.

The term "conversion material" or "color converter" refers to a material that is excited by a photon of a first wavelength and emits photons of a second, different wavelength.

In the context of the present invention, "a phosphor-converted LED" refers to an LED element having a phosphor material layer coated thereon for converting or changing the color of the light emitted by the LED element to a different color.

A quantum dot is a nanocrystal made of semiconductor materials that is small enough to exhibit quantum mechanical properties. Quantum dots are showing remarkably narrow emission spec-tra, i.e. with extraordinary small FWHM (full width of half maximum). The color output of the dots can be tuned by controlling the size of the crystals. With a smaller size in quantum dots, the quantum dots emit light of a shorter wavelength.

In the context of the present invention, the term "center wavelength" of a given spectral distribution F(A) is defined as the following average: $Ac=\int A^\wedge F(A)\ dA/\int_F(A)\ dA$.

In the context of the present invention, a "blue light" is understood to mean light in the blue range of the electromagnetic spectrum with a center wavelength of emission usually in the range of 350 to 500 nm, preferably 420 to 495 nm, more preferably 440 to 492 nm.

Suitable semiconductor materials for generating blue light are silicon carbide, zinc selenide and nitrides such as aluminum nitride (AlN), gallium nitride (GaN), indium nitride (InN) and indium gallium nitride (InGaN). LEDs typically have a narrow wavelength distribution that is tightly centered about their peak wavelength. Standard InGaN-based blue LEDs are fabricated on a sapphire substrate and the peak emission wavelength is usually centered at 445 to 455 nm.

In the context of the present invention, a "red light" is understood to mean light in the red range of the electromagnetic spectrum with a center wavelength of emission usually in the range of 620 to 780 nm, preferably 622 to 750 nm.

In the context of the present invention, a "green light" is understood to mean light in the green range of the electromagnetic spectrum with a center wavelength of emission usually in the range of 495 to 577 nm, preferably 492 to 570 nm.

In the context of the present invention, a "yellow light" is understood to mean light in the yellow range of the electromagnetic spectrum with a center wavelength of emission usually in the range of 570 to 597 nm, preferably 577 to 590 nm.

In the context of the present invention, a "cyan light" is understood to mean light in the cyan range of the electromagnetic spectrum with a center wavelength of emission usually in the range of 490 to 520 nm.

White LEDs cannot be differentiated by wavelength. They appear "cool", "neutral" or "warm" white due to their color temperature, measured in Kelvin (K).

The correlated color temperature (CCT) is the temperature of a black body radiator that is perceived by the human eye to emit the same white light as the LEDs. The correlated color temperature (CCT) describes the color appearance of white light emitted from electric light sources and is measured in Kelvin. It is determined according to the CIE international standard. CCT from a white light source usually is in the range from 1 500 K to 20 000 K, especially 2 000 K to 20 000 K. White light having higher CCT contains relatively higher intensity in the short wave-length region (blue) and relatively lower intensity in the longer wavelength region (red) compared to white light with lower CCT. Accordingly, higher CCTs generally indicate white light having a more significant blue component or a cool tone, while lower CCTs generally indicate light having a more significant red tint or a warm tone. A white light having a CCT in the range from 4 500 K to 20 000 K is often referred to as cool white light, a white light having a CCT in the range from 2 700 K to 3 200 K is often referred to as warm-white light and a white light having a CCT in the range between 3 200 K to 4 500 K is often referred to as neutral white. Warmer color temperatures are especially suitable for living spaces, especially in Europe. Depending on the geographic region and application, in European offices a white light having a CCT around 4000 K is usually preferred, while common European households usually prefer a white light having a CCT around 2700 K to 3000 K. In Asia usually a white light having a CCT around 5000 K to 6500K is preferred, but sometimes also a white light having a CCT around 2700 K is preferred.

Color rendering (CRI) is a measure how a light source makes the color of an object appear to the human eye and how well subtle variations in color shade are revealed. According to CIE 17.4, International Lighting Vocabulary, color rendering (CRI) is defined as "the effect of an illuminant on the color appearance of objects by conscious or unconscious comparison with the color appearance under a reference illuminant". The average or general color rendering index Ra is calculated from the differences in the chromaticities of the eight pastel CIE standard (reference) color samples R1 to R8 (CIE 13.3-1995). Negative values are also possible. A reference source, such as black body radiation, is defined as having a CRI index (Ra) of 100 (which is the maximum), i.e. a value of 100 indicates that the source renders colors in a manner identical to the reference. The lower the CRI rating, the less accurately colors will be reproduced. For many general interior illumination applications, a CRI value (Ra) of greater than 80 is acceptable. For general lighting, the color rendering index should be above 85. In applications where accurate color rendering is required, a high CRI Ra of at least 90 is usually highly desirable, so that objects illuminated by the lighting source may appear to have more natural coloring to the human eye.

CRI Ra does not include coefficients corresponding to six highly saturated colors (R9-R14). Of these, R9 corresponds to a strong red color, which may affect a red-green contrast that may be beneficial in rendering colors. Often, the ability to reproduce red colors well is essential for accurately rendering colors, as the color red is often found mixed into processed colors. Thus, if a light source cannot render red correctly, things that are reddish will turn dull. Accordingly, light sources with high CRI Ra and with positive R9 value tend to produce the most vivid colors.

According to the CIE 1931 standard colorimetric system, colors are perceived by human eye following specific color curves. The standard luminosity curve VA accounts for the wavelength dependence of the sensitivity of human eye. The luminosity curve has a maximum possible value of 683 lm/W, for the case of monochromatic light at a wavelength of 555 nm (green). Luminous flux is the measure of the perceived power of light.

The residues mentioned in the specification of the present application generally have the following preferred meanings, if said residues are not further specified in specific embodiments mentioned below: The expression "halogen" denotes in each case fluorine, bromine, chlorine or iodine, particularly chlorine, bromide or iodine.

The term "unsubstituted or substituted $C_1$-$C_{20}$alkyl" as used herein and in the alkyl moieties of alkoxy, COO$C_1$-$C_{20}$alkyl, OCO$C_1$-$C_{20}$alkyl, $C_8$alkylamino, $C_6$-$C_{10}$arylamino and the like refers to saturated straight-chain or branched hydrocarbon radicals having usually 1 to 20 ("$C_1$-$C_{20}$-alkyl"), 1 to 18 ("$C_1$-$C_{18}$-alkyl"), 1 to 12 ("$C_1$-$C_{12}$-alkyl"), 1 to 8 ("$C_1$-$C_5$-alkyl") or 3 to 8 ("$C_3$-$C_8$-alkyl") carbon atoms. Examples of alkyl groups are especially methyl, ethyl, n-propyl, isopropyl, n-butyl, isobutyl, sec-butyl, tert-butyl, n-pentyl, 1-methylbutyl, 1-ethylpropyl, neo-pentyl, n-hexyl, 1-methylpentyl, 2-methylpentyl, 1-ethylbutyl, 2-ethylbutyl, n-heptyl, 1-methylhexyl, 2-methylhexyl, 1-ethylpentyl, 1-propylbutyl, 2-ethylpentyl, n-octyl, 1-methylheptyl, 2-methylheptyl, 1-ethylhexyl, 2-ethylhexyl, 1-propylpentyl, 2-propylpentyl, n-nonyl, etc.

Substituted alkyl groups, depending on the length of the alkyl chain, have one or more (e.g. 1, 2, 3, 4, 5 or more than 5) substituents. These are preferably each independently of each other selected from unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted heteroaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, $CF_3$, unsubstituted or substituted alkylcarbonyloxy, formyl, acyl, COOH, carboxylate, —COO$R^{Ar1}$, N$E^1E^2$, —NR$^{Ar1}$COR$^{Ar2}$, —CONR$^{Ar1}$R$^{Ar2}$, —SO2NR$^{Ar1}$R$^{Ar2}$ and SO3R$^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted alkyl groups have one or more, for example 1,2 or 3 substituent(s) selected from unsubstituted or substituted cycloalkyl, unsubstituted or substituted aryl, fluorine, chlorine, bromine, hydroxyl, alkoxy, polyalkyleneoxy, mercapto, alkylthio, cyano, $CF_3$, $NE^1E^2$, —$NR^{Ar1}COR^{Ar2}$, —$CONR^{Ar1}R^{Ar2}$, —$SO2NR^{Ar1}R^{Ar2}$, and $SO3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

Special embodiments of substituted alkyl groups are alkyl groups, wherein one hydrogen atom has been replaced by an aryl radical ("aralkyl", also referred to hereinafter as arylalkyl or arylalkylene), in particular a phenyl radical. The aryl radical in turn may be unsubstituted or substituted, suitable substituents are the substituents mentioned below for aryl. Particular examples of aryl-$C_1$-$C_4$-alkyl include benzyl, 1-phenethyl, 2-phenetyl, 1-phenylpropyl, 2-phenylpropyl, 3-phenyl-1-propyl, 2-phenyl-1-propyl, naphthylmethyl, naphthylethyl, etc.

Further special embodiments of substituted alkyl groups are alkyl groups, where some or all of the hydrogen atoms in these groups may be replaced by halogen atoms as mentioned above, for example $C_1$-$C_4$-haloalkyl.

Preferably, the alkyl groups are unsubstituted.

The term "$C_2$-$C_{20}$alkenyl" as used herein refers to straight-chain or branched hydrocarbon groups having usually 2 to 20 ("$C_2$-$C_{20}$-alkenyl"), 2 to 18 ("$C_2$-$C_{18}$-alkenyl"), 2 to 10 ("$C_2$-$C_{10}$-alkenyl"), 2 to 8 ("$C_2$-$C_8$-alkenyl"), or 2 to 6 ("$C_2$-$C_6$-alkenyl") carbon atoms and one or more, e.g. 2 or 3, double bonds in any position. Substituted alkenyl groups, depending on the length of the alkenyl chain, have one or more (e.g. 1, 2, 3, 4, 5 or more than 5) substituents. These are preferably each independently of each other selected from unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, $CF_3$, unsubstituted or substituted alkylcarbonyloxy, formyl, acyl, COOH, carboxylate, —$COOR^{Ar1}$, $NE^1E^2$, —$NR^{Ar1}COR^{Ar2}$, —$CONR^{Ar1}R^{Ar2}$, —$SO2NR^{Ar1}R^{Ar2}$ and $SOsR^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted alkenyl groups have one or more, for example 1, 2 or 3 substituent(s) selected from unsubstituted or substituted cycloalkyl, unsubstituted or substituted aryl, fluorine, chlorine, bromine, hydroxyl, alkoxy, polyalkyleneoxy, mercapto, alkylthio, cyano, $CF_3$, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. Preferably, the alkenyl groups are unsubstituted.

The term "$C_1$-$C_{20}$alkoxy" as used herein refers to an alkyl group bound through an oxygen atom, that is, an "alkoxy" group may be represented as —O-alkyl, where alkyl is as defined above. Preferred alkoxy groups are $C_1$-$C_4$-alkoxy groups, for example, methoxy, ethoxy, n-propoxy, 1-methylethoxy (isopropoxy), butoxy, 1-methylpropoxy (sec-butoxy), 2-methylpropoxy (isobutoxy) or 1,1-dimethylethoxy (tert-butoxy).

Accordingly, the term "unsubstituted or substituted alkoxy" as used herein refers to —O-alkyl, where alkyl is unsubstituted or substituted as defined above.

Preferably, the alkoxy groups are unsubstituted.

The term "$C_3$-$C_{20}$cycloalkyl" as used herein refers to mono- or bi- or polycyclic saturated hydrocarbon radicals having usually 3 to 20 ($C_3$-$C_{20}$-cycloalkyl), preferably 3 to 8 ("$C_3$-$C_8$-cycloalkyl") or 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 to 12 carbon atoms comprise bicyclo[2.2.1]heptyl, bicyclo[3.1.1]heptyl, bicyclo[2.2.2]octyl, bicyclo[3.3.0]octyl, bicyclo[3.2.1]octyl, bicyclo[3.3.1]nonyl, bicyclo[4.2.1]nonyl, bicyclo[4.3.1]decyl, bicyclo[3.3.2]decyl, bicyclo[4.4.0]decyl, bicyclo[4.2.2]decyl, bicyclo[4.3.2]undecyl, bicyclo[3.3.3]undecyl, bicyclo[4.3.3]dodecyl, and perhydronaphthyl. Examples of polycyclic rings are perhydroanthracyl, perhydrofluorenyl, perhydrochrysenyl, perhydropicenyl, and adamantyl.

Substituted cycloalkyl groups may, depending on the ring size, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, $CF_3$, unsubstituted or substituted alkylcarbonyloxy, formyl, acyl, COOH, carboxylate, —$COOR^{Ar1}$, —$NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted cycloalkyl groups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, $CF_3$, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

Preferably, the cycloalkyl groups are unsubstituted.

The term "an aliphatic heterocycle having a ring formed of 3 to 24 atoms" refers to nonaromatic, partially unsaturated or fully saturated, heterocyclic rings having generally 3 to 24 ring members, preferably 4 to 10 ring members, more preferably 5 to 8 ring members, most preferably 5 or 6 ring members, comprising besides carbon atoms as ring members, one, two, three or four heteroatoms or heteroatom-containing groups selected from O, N, $NR^{cc}$, S, SO and $S(O)_2$ as ring members, wherein $R^{cc}$ is hydrogen, $C_1$-$C_{20}$-alkyl, $C_3$-$C_{24}$-cycloalkyl, heterocycloalkyl, $C_6$-$C_{24}$-aryl or heteroaryl. Examples of heterocycloalkyl groups are especially pyrrolidinyl, piperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted aliphatic heterocyclic groups may, depending on the ring size, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, $CF_3$, unsubstituted or substituted alkylcarbonyloxy, formyl, acyl, COOH, carboxylate, —$COOR^{Ar1}$, —$NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted aliphatic heterocyclic groups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, $CF_3$, $NE^1E^2$, —$NR^{Ar1}COR^{Ar2}$, —$CONR^{Ar1}R^{Ar2}$, —$SO2NR^{Ar1}R^{Ar2}$, and —$SOsR^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

Preferably, the aliphatic heterocyclic groups are unsubstituted.

For the purpose of the present invention, the term "$C_6$-$C_{24}$aryl" refers to phenyl and bi- or polycyclic carbocycles having at least one fused phenylene ring, which is bound to the remainder of the molecule. Examples of bi- or polycyclic carbocycles having at least one phenylene ring include naphthyl, tetrahydronaphthyl, indanyl, indenyl, anthracenyl, fluorenyl, pyrenyl etc. Preferably, the term "aryl" denotes phenyl and naphthyl.

Substituted aryls may, depending on the number and size of their ring systems, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted heteroaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, $CF_3$, unsubstituted or substituted alkylcarbonyloxy, formyl, acyl, COOH, carboxylate, —$COOR^{Ar1}$, —$NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted arylgroups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, $CF_3$, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

Substituted aryl is preferably aryl substituted by at least one alkyl group ("alkaryl", also referred to hereinafter as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. A special embodiment relates to alkaryl groups, wherein alkyl is unsubstituted. Alkaryl is preferably phenyl which bears 1, 2, 3, 4 or 5, preferably 1, 2 or 3, more preferably 1 or 2 alkyl substituents. Aryl which bears one or more alkyl radicals, is, for example, 2-, 3- and 4-methylphenyl, 2,4-, 2,5-, 3,5-, 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-n-propylphenyl, 2-, 3- and 4-iso-propylphenyl, 2,4-, 2,5-, 3,5- and 2,6-di-n-propylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 1-,3- and 4-butylphenyl, 2,4-, 2,5-, 3,5- and 2,6-dibutylphenyl, 2,4,6-tributylphenyl, 2-,1- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl.

Preferably, the aryl groups are unsubstituted.

In the context of the present invention, the expression "heteroaryl having a ring formed of 3 to 24 atoms" (also referred to as heteroaryl) comprises heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The heteroaryl groups have preferably 5 to 18, e.g. 5, 6, 8, 9, 10, 11, 12, 13 or 14, ring atoms.

Monocyclic heteroaryl groups are preferably 5- or 6-membered heteroaryl groups, such as 2-furyl (furan-2-yl), 3-furyl (furan-3-yl), 2-thienyl (thiophen-2-yl), 3-thienyl (thiophen-2-yl), 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxa-diazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic heteroaryl groups have 2, 3, 4 or more than 4 fused rings. The fused-on rings may be aromatic, saturated or partly unsaturated. Examples of polycyclic heteroaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, carbazolyl (dibenzopyrrolyl), dibenzofuranyl, dibenzothiophenyl, naphtho[2,3-b]thiophenyl, naphtha[2,3-b]furyl, dihydroindolyl, dihydroindoliz-inyl, dihydroisoindolyl, dihydroquinolinyl, benzimidazolo[1,2-a]benzimidazolyl and dihydroiso-quinolinyl.

Substituted heteroaryl groups may, depending on the number and size of their ring systems, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted heteroaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, $CF_3$, unsubstituted or substituted alkylcarbonyloxy, formyl, acyl, COOH, carboxylate, —$COOR^{Ar1}$, —$NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted heteroaryl groups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, $CF_3$, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, $R^{Ar1}$ and $R^{Ar2}$ are as defined above.

Preferably, the heteroaryl groups are unsubstituted.

The term "$C_7$-$C_{31}$alkaryl" refers to aryl substituted by at least one alkyl group ("alkaryl", also referred to as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard as well as in view of preferred alkaryl groups, reference is made to the above statements regarding unsubstituted and substituted aryl.

Preferably, the alkaryl groups are unsubstituted.

The term "amino" refers to amino groups preferably having the formula —$NE^1E^2$, where $E^1$ and $E^2$ are each independently hydrogen, unsubstituted or substituted $C_1$-$C_{18}$-alkyl, unsubstituted or substituted $C_2$-$C_{18}$-alkenyl, unsubstituted or substituted $C_3$-$C_{20}$-cycloalkyl or unsubstituted or substituted $C_6$-$C_{10}$-aryl, and amino; or $E^1$ and $E^2$ form together with the N atom a 3 to 24 membered ring, preferably a 4 to 10 membered ring, more preferably a 5 to 6 membered ring, which is unsubstituted or substituted by one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, $CF_3$, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, $R^{Ar1}$ and $R^{Ar2}$ are as defined above, or fused with one or two 5 or 6 membered rings which may be aromatic or aliphatic and unsubstituted or substituted by one or more, for example 1, 2 or 3 of the substituent(s) mentioned before. Preferred amino groups are $C_1$-$C_8$alkylamino and $C_6$-$C_{10}$arylamino. The alkyl and aryl groups in the alkylamino group respectively in the arylamino group are defined as the alkyl and aryl groups mentioned above.

The "carbon number of a to b" in the expression of "$C_a$-$C_b$ X groups" is the carbon number of the unsubstituted X group and does not include the carbon atom(s) of an optional substituent.

Fused ring systems can comprise alicyclic, aliphatic heterocyclic, aromatic and heteroaromatic rings and combinations thereof, hydroaromatic joined by fusion. Fused ring systems comprise two, three or more (e.g. 4, 5, 6, 7 or 8) rings. Depending on the way in which the rings in fused ring systems are joined, a distinction is made between ortho-fusion, i.e. each ring shares at least one edge or two atoms with each adjacent ring, and peri-fusion in which a carbon atom belongs to more than two rings. Preferred fused ring systems are ortho-fused ring systems.

When a dotted line appears in a formula showing a substructure of a compound of the present invention, it denotes the attachment bond in the remainder molecule.

Compounds of formula (I) The optical data communication system according to the present invention comprises at least one compound of formula (I)

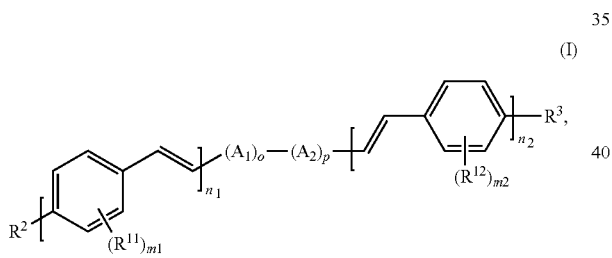

(I)

wherein
n1 and n2 are each independently 1, 2 or 3, preferably 1 or 2,
m1 and m2 are each independently 0, 1, 2, 3 or 4, preferably 0, 1 or 2, and
$R^{11}$ and $R^{12}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl, preferably H, unsubstituted or substituted $C_1$-$C_{20}$alkyl or unsubstituted or substituted $C_1$-$C_{20}$alkoxy,
$R^2$ and $R^3$ are each independently hydrogen, unsubstituted or substituted $C_1$-$C_{20}$alkyl, unsubstituted or substituted $C_2$-$C_{20}$alkenyl, unsubstituted or substituted $C_1$-$C_{20}$alkoxy, unsubstituted or substituted $C_3$-$C_{20}$cycloalkyl, unsubstituted or substituted $C_6$-$C_{24}$aryl, an unsubstituted or substituted aliphatic heterocycle having a ring formed of 3 to 24 atoms; unsubstituted or substituted heteroaryl having a ring formed of 3 to 24 atoms; amino, CN, $CF_3$, $COOC_1$-$C_{20}$alkyl, $OCOC_1$-$C_{20}$alkyl or unsubstituted or substituted $C_7$-$C_{31}$alkaryl, $A_2$ is

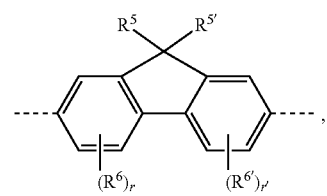

(1)

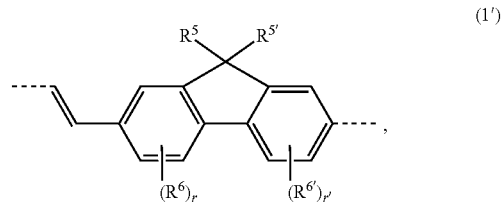

(1')

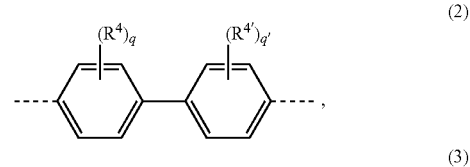

(2)

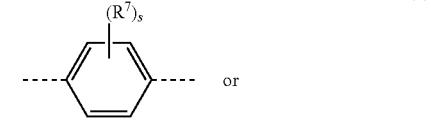

(3)

or

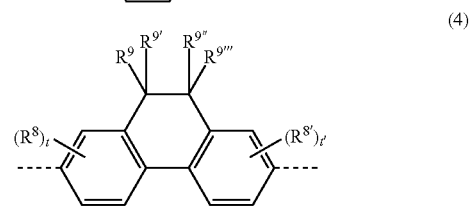

(4)

$A_1$ is

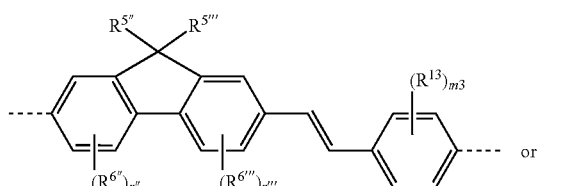

(5)

or

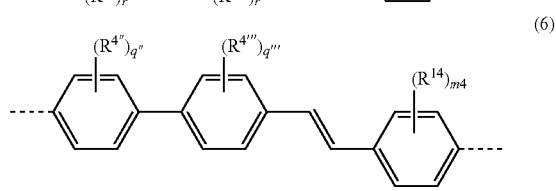

(6)

p is 1 or 2, preferably 1,
o is 0, 1 or 2,
q, q', q", q''', s, m3 and m4 are each independently 0, 1, 2, 3 or 4, preferably 0, 1 or 2,
r, r', r", r''', t and t' are each independently 0, 1, 2 or 3, preferably 0, 1 or 2,
$R^4$, $R^{4'}$, $R^{4''}$, $R^{4'''}$, $R^6$, $R^{6'}$, $R^{6''}$, $R^{6'''}$, $R^7$, $R^8$, $R^{8'}$, $R^{13}$ and $R^{14}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl, $R^5$, $R^{5'}$, $R^{5''}$, $R^{5'''}$, $R^9$, $R^{9'}$, $R^{9''}$ and $R^{9'''}$ are each independently H or unsubstituted or substituted $C_1$-$C_{20}$alkyl, unsubstituted or substituted $C_6$-$C_{30}$aryl or $C_7$-$C_{31}$alkaryl, wherein the dotted lines are bonding sites.

n1 and n2 in the compound of formula (I) are each independently 1, 2 or 3, preferably 1 or 2.

m1 and m2 in the compound of formula (I) are each independently 0, 1, 2, 3 or 4, preferably 0, 1 or 2.

$R^{11}$ and $R^{12}$ in the compound of formula (I) are each independently H, unsubstituted or substituted $C_1$-$C_{20}$alkyl, unsubstituted or substituted $C_1$-$C_{20}$alkoxy, unsubstituted or substituted $C_6$-$C_{30}$aryl or unsubstituted or substituted $C_7$-$C_{31}$alkaryl, preferably H, unsubstituted or substituted $C_1$-$C_{20}$alkyl or unsubstituted or substituted $C_1$-$C_{20}$alkoxy.

$R^2$ and $R^3$ in the compound of formula (I) are each independently hydrogen, unsubstituted or substituted $C_1$-$C_{20}$alkyl, unsubstituted or substituted $C_2$-$C_{20}$alkenyl, unsubstituted or substituted $C_1$-$C_{20}$alkoxy, unsubstituted or substituted $C_3$-$C_{20}$cycloalkyl, unsubstituted or substituted $C_6$-$C_{24}$aryl, an unsubstituted or substituted aliphatic heterocycle having a ring formed of 3 to 24 atoms; unsubstituted or substituted heteroaryl having a ring formed of 3 to 24 atoms; amino, CN, $CF_3$, $COOC_1$-$C_{20}$alkyl, $OCOC_1$-$C_{20}$alkyl or unsubstituted or substituted $C_7$-$C_{31}$alkaryl, preferably hydrogen, unsubstituted or substituted $C_1$-$C_8$alkyl, unsubstituted or substituted $C_2$-$C_8$alkenyl, unsubstituted or substituted $C_1$-$C_8$alkoxy, unsubstituted or substituted $C_5$-$C_6$cycloalkyl, unsubstituted or substituted $C_6$-$C_{10}$aryl, an unsubstituted or substituted aliphatic heterocycle having a ring formed of 5 or 6 atoms; unsubstituted or substituted heteroaryl having a ring formed of 5 to 18 atoms; $C_1$-$C_8$alkylamino, $C_6$-$C_{10}$arylamino, CN, $CF_3$, $COOC_1$-$C_8$alkyl, $OCOC_1$-$C_8$alkyl or unsubstituted or substituted $C_7$-$C_{11}$alkaryl, more preferably hydrogen, unsubstituted or substituted $C_6$-$C_{10}$aryl, unsubstituted or substituted heteroaryl having a ring formed of 5 to 18 atoms; $C_1$-$C_8$alkylamino, $C_6$-$C_{10}$arylamino, CN, $CF_3$ or $COOC_1$-$C_8$alkyl.

Most preferably, $R^2$ and $R^3$ are each independently hydrogen,

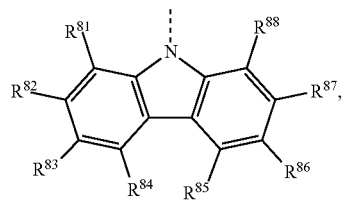

$C_1$-$C_8$alkylamino, $C_6$-$C_{10}$arylamino, CN, $CF_3$, $COO(C_1$-$C_8)$alkyl,

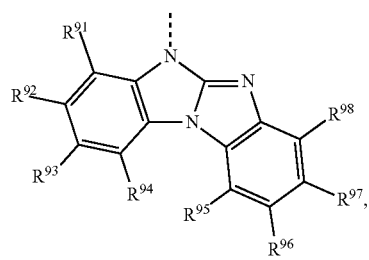

-continued

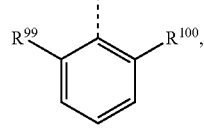

wherein $R^{81}$, $R^{82}$, $R^{83}$, $R^{84}$, $R^{85}$, $R^{86}$, $R^{87}$ and $R^{88}$ are each independently hydrogen or unsubstituted or substituted $C_1$-$C_{20}$alkyl, unsubstituted or substituted $C_1$-$C_{20}$alkoxy, unsubstituted or substituted $C_6$-$C_{30}$aryl or unsubstituted or substituted $C_7$-$C_{31}$alkaryl, preferably hydrogen or unsubstituted or substituted $C_1$-$C_{20}$alkyl, more preferably, $R^{81}$, $R^{82}$, $R^{84}$, $R^{85}$, $R^{87}$ and $R^{88}$ are hydrogen and $R^{83}$ and $R^{86}$ are unsubstituted or substituted $C_1$-$C_{20}$alkyl, preferably unsubstituted or substituted $C_3$-$C_8$alkyl, $R^{91}$, $R^{92}$, $R^{93}$, $R^{94}$, $R^{95}$, $R^{96}$, $R^{97}$ and $R^{98}$ are each independently hydrogen or unsubstituted or substituted $C_1$-$C_{20}$alkyl, unsubstituted or substituted $C_1$-$C_{20}$alkoxy, unsubstituted or substituted $C_6$-$C_{30}$aryl, for example phenyl, naphthyl or pyrenyl, or unsubstituted or substituted $C_7$-$C_{31}$alkaryl, preferably hydrogen or unsubstituted or substituted $C_1$-$C_{20}$alkyl, $R^{99}$ and $R^{100}$ are each independently hydrogen or unsubstituted or substituted $C_1$-$C_{20}$alkyl, unsubstituted or substituted $C_1$-$C_{20}$alkoxy, unsubstituted or substituted $C_6$-$C_{30}$aryl, for example phenyl, naphthyl or pyrenyl, or unsubstituted or substituted $C_7$-$C_{31}$alkaryl, preferably hydrogen or unsubstituted or substituted $C_1$-$C_{20}$alkyl, wherein the dotted lines are bonding sites.

Further most preferably, $R^2$ and $R^3$ are each independently hydrogen,

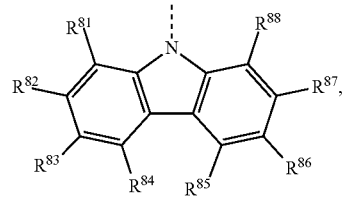

$CF_3$ or CN, wherein $R^{81}$, $R^{82}$, $R^{83}$, $R^{84}$, $R^{85}$, $R^{86}$, $R^{87}$ and $R^{88}$ are each independently hydrogen or unsubstituted or substituted $C_1$-$C_{20}$alkyl, unsubstituted or substituted $C_1$-$C_{20}$alkoxy, unsubstituted or substituted $C_6$-$C_{30}$aryl, for example phenyl, naphthyl or pyrenyl, or unsubstituted or substituted $C_7$-$C_{31}$alkaryl, preferably hydrogen or unsubstituted or substituted $C_1$-$C_{20}$alkyl, more preferably, $R^{81}$, $R^{82}$, $R^{84}$, $R^{85}$, $R^{87}$ and $R^{88}$ are hydrogen and $R^{83}$ and $R^{86}$ are unsubstituted or substituted $C_1$-$C_{20}$alkyl, preferably unsubstituted or substituted $C_3$-$C_8$alkyl.

$A_1$ is

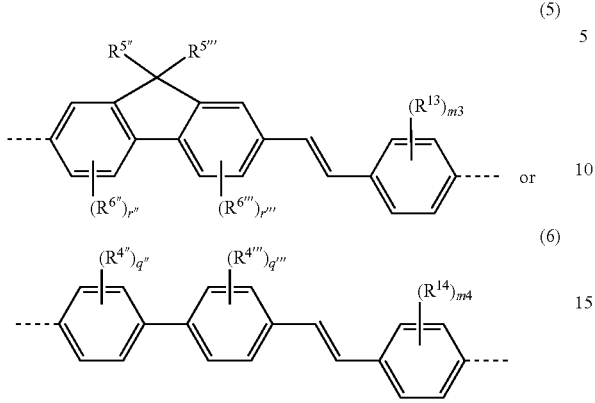

q", q''', m3 and m4 are each independently 0, 1, 2, 3 or 4, preferably 0, 1 or 2, r" and r''' are each independently 0, 1, 2 or 3, preferably 0, 1 or 2, $R^{4''}$, $R^{4'''}$, $R^{6''}$, $R^{6'''}$, $R^{13}$ and $R^{14}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl, preferably each independently H, unsubstituted or substituted $C_1$-$C_8$alkyl or unsubstituted or substituted $C_1$-$C_8$alkoxy, unsubstituted or substituted $C_6$-$C_{10}$aryl or unsubstituted or substituted $C_7$-$C_{11}$alkaryl, more preferably H, $R^{5''}$ and $R^{5'''}$ are each independently H or unsubstituted or substituted $C_1$-$C_{20}$alkyl, unsubstituted or substituted $C_6$-$C_{30}$aryl or $C_7$-$C_{31}$alkaryl, preferably H or unsubstituted or substituted $C_1$-$C_8$alkyl, unsubstituted or substituted $C_6$-$C_{10}$aryl or $C_7$-$C_{11}$alkaryl, more preferably unsubstituted $C_1$-$C_8$alkyl, wherein the dotted lines are bonding sites.
Preferably, $A_1$ is

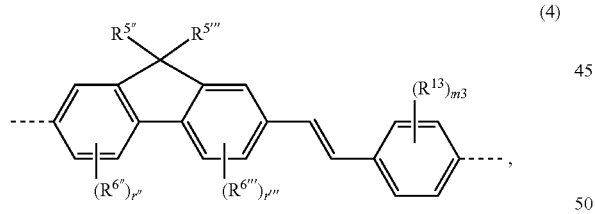

wherein
m3 is 0,1,2,3 or 4, preferably 0, 1 or 2,
r" and r''' are each independently 0, 1, 2 or 3, preferably 0, 1 or 2,
$R^{6''}$, $R^{6'}$ and $R^{13}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl, preferably each independently H, unsubstituted or substituted $C_1$-$C_8$alkyl or unsubstituted or substituted $C_1$-$C_8$alkoxy, unsubstituted or substituted $C_6$-$C_{10}$aryl or unsubstituted or substituted $C_7$-$C_{11}$alkaryl, more preferably H, $R^{5''}$ and $R^{5'''}$ are each independently H or unsubstituted or substituted $C_1$-$C_{20}$alkyl, unsubstituted or substituted $C_6$-$C_{30}$aryl or $C_7$-$C_{31}$alkaryl, preferably H or unsubstituted or substituted $C_1$-$C_8$alkyl, unsubstituted or substituted $C_6$-$C_{10}$aryl or $C_7$-$C_{11}$alkaryl, more preferably unsubstituted $C_1$-$C_8$alkyl, wherein the dotted lines are bonding sites.

$A_2$ is

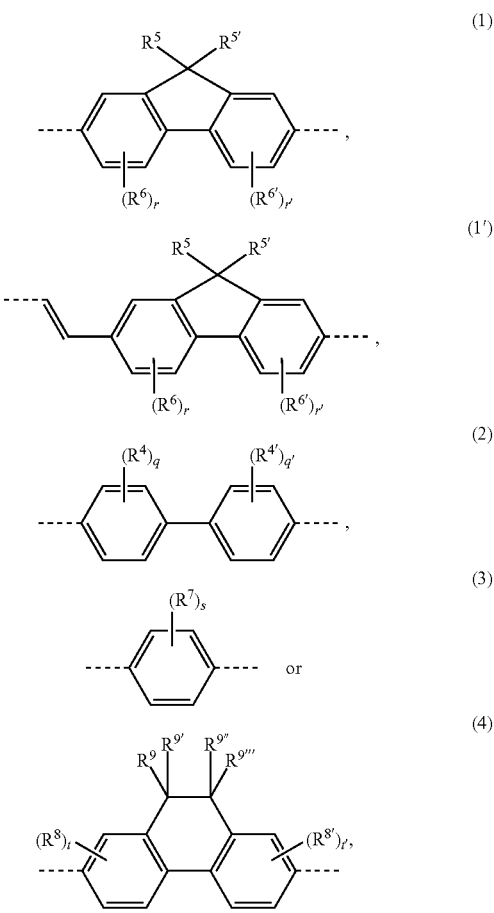

wherein
q, q', s are each independently 0, 1, 2, 3 or 4, preferably 0, 1 or 2,
r, r', t and t' are each independently 0, 1, 2 or 3, preferably 0, 1 or 2,
$R^4$, $R^{4'}$, $R^6$, $R^{6'}$, $R^{6''}$, $R^7$, $R^8$ and $R^{8'}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl, preferably each independently H, unsubstituted or substituted $C_1$-$C_8$alkyl or unsubstituted or substituted $C_1$-$C_8$alkoxy, unsubstituted or substituted $C_6$-$C_{10}$aryl or unsubstituted or substituted $C_7$-$C_{11}$alkaryl, more preferably H,
$R^5$, $R^{5'}$, $R^9$, $R^{9'}$, $R^{9''}$ and $R^{9'''}$ are each independently H or unsubstituted or substituted $C_1$-$C_{20}$alkyl, unsubstituted or substituted $C_6$-$C_{30}$aryl or $C_7$-$C_{31}$alkaryl, preferably H or unsubstituted or substituted $C_1$-$C_8$alkyl, unsubstituted or substituted $C_6$-$C_{10}$aryl or $C_7$-$C_{11}$alkaryl, more preferably H or unsubstituted $C_1$-$C_8$alkyl, most preferably, $R^5$ and $R^{5'}$ are unsubstituted $C_1$-$C_8$alkyl, wherein the dotted lines are bonding sites.

Preferably, A₂ is a group formula

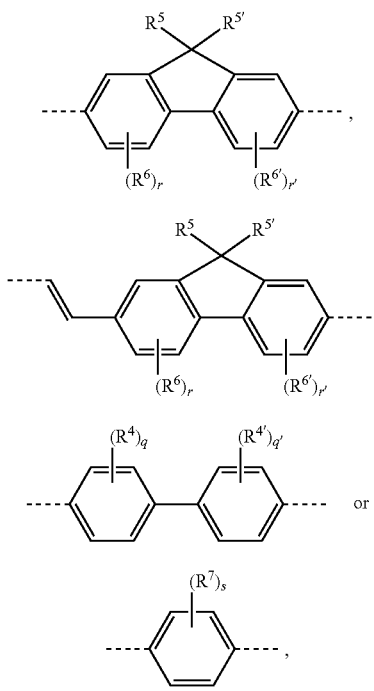

more preferably A₂ is a group of formula (1), (1') or (2), most preferably,
A₂ is a group of formula (1) or (!1),
wherein
in formula (1) and (1'):
r and r' are each independently 0, 1, 2 or 3, preferably 0, 1 or 2,
$R^5$ and $R^{5'}$ are each independently H or unsubstituted or substituted $C_1$-$C_{20}$alkyl, unsubstituted or substituted $C_6$-$C_{30}$aryl or $C_7$-$C_{31}$alkaryl, preferably H or unsubstituted or substituted $C_1$-$C_8$alkyl, unsubstituted or substituted $C_6$-$C_{10}$aryl or $C_7$-$C_{11}$alkaryl, more preferably H or unsubstituted $C_1$-$C_8$alkyl, most preferably unsubstituted $C_1$-$C_8$alkyl,
wherein the dotted lines are bonding sites;
in formula (2):
q and q' are each independently 0, 1, 2, 3 or 4, preferably 0, 1 or 2,
$R^4$ and $R^{4'}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl, preferably each independently H, unsubstituted or substituted $C_1$-$C_8$alkyl or unsubstituted or substituted $C_1$-$C_8$alkoxy, unsubstituted or substituted $C_6$-$C_{10}$aryl or unsubstituted or substituted $C_7$-$C_{11}$alkaryl, more preferably H,
wherein the dotted lines are bonding sites;
in formula (3):
s is 0, 1, 2, 3 or 4, preferably 0, 1 or 2,
$R^7$ is H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{30}$alkaryl, preferably H, unsubstituted or substituted $C_1$-$C_8$alkyl or unsubstituted or substituted $C_1$-$C_8$alkoxy, unsubstituted or substituted $C_6$-$C_{10}$aryl or unsubstituted or substituted $C_7$-$C_{11}$alkaryl, more preferably H,
wherein the dotted lines are bonding sites.

Further most preferably, A₂ is a group of formula (1), wherein r and r' are 0 and $R^5$ and $R^{5'}$ are unsubstituted $C_1$-$C_8$alkyl.

Preferably, $R^5$, $R^{5'}$, $R''$ and $R^{5''''}$ are each independently unsubstituted or substituted $C_1$-$C_{20}$alkyl, unsubstituted or substituted $C_6$-$C_{30}$aryl or unsubstituted or substituted $C_7$-$C_{31}$alkaryl, preferably unsubstituted or substituted $C_1$-$C_{20}$alkyl, more preferably unsubstituted or substituted $C_3$-$C_8$alkyl, most preferably unsubstituted $C_3$-$C_8$alkyl.

Most preferably, A₁ is

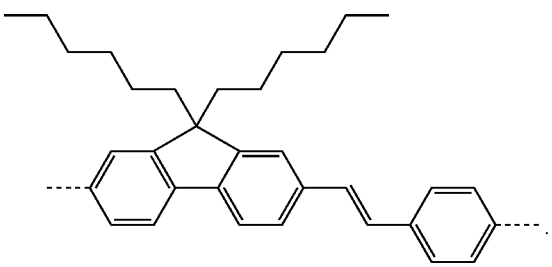

Most preferably, A₂ is or

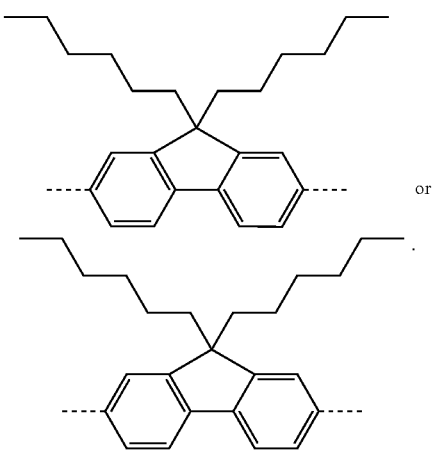

In formula (I), o is preferably 0.
Further preferably, the compound of formula (I) is represented by a compound of formula (Ia)

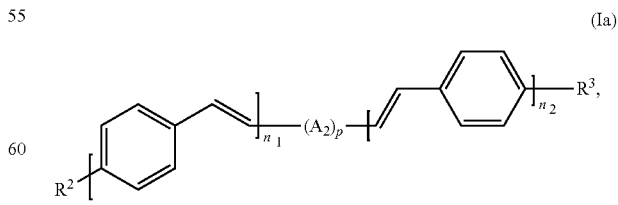

wherein
n1 and n2 are each independently 1 or 2,
$R^2$ and $R^3$ are each independently hydrogen,

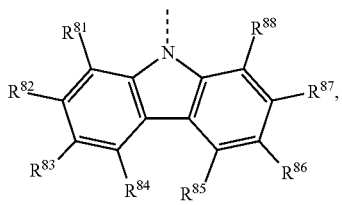

CF$_3$ or CN,
wherein
R$^{81}$, R$^{82}$, R$^{83}$, R$^{84}$, R$^{85}$, R$^{86}$, R$^{87}$, R$^{88}$ are each independently hydrogen or unsubstituted or substituted C$_1$-C$_{20}$alkyl, unsubstituted or substituted C$_1$-C$_{20}$alkoxy, unsubstituted or substituted C$_6$-C$_{30}$aryl, for example phenyl, naphthyl or pyrenyl, or unsubstituted or substituted C$_7$-C$_{31}$alkaryl, preferably hydrogen or unsubstituted or substituted C$_1$-C$_{20}$alkyl, more preferably, R$^{81}$, R$^{82}$, R$^{84}$, R$^{85}$, R$^{87}$ and R$^{88}$ are hydrogen and R$^{83}$ and R$^{86}$ are unsubstituted or substituted C$_1$-C$_{20}$alkyl, preferably unsubstituted or substituted C$_3$-C$_8$alkyl, A$_2$ is,

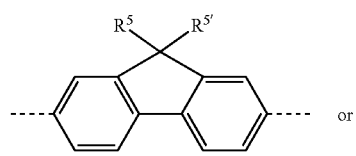

(1)

or (1')

p is 1 or 2, preferably 1,

R$^5$ are R$^{5'}$ are each independently unsubstituted or substituted C$_1$-C$_{20}$alkyl, unsubstituted or substituted C$_6$-C$_{30}$aryl or unsubstituted or substituted C$_7$-C$_{31}$alkaryl, preferably unsubstituted or substituted C$_1$-C$_{20}$alkyl, more preferably unsubstituted or substituted C$_3$-C$_8$alkyl, most preferably unsubstituted C$_3$-C$_8$alkyl, wherein the dotted lines are bonding sites.

More preferably, in formula (I) and (Ia), p is 1;

o is 0;

n1 and n2 are each independently 1 or 2;

q, q', q", q'", s, m3 and m4 are 0; and r, r', r" and r'" are 0.

Preferred compounds of formula (I) are shown in the following:

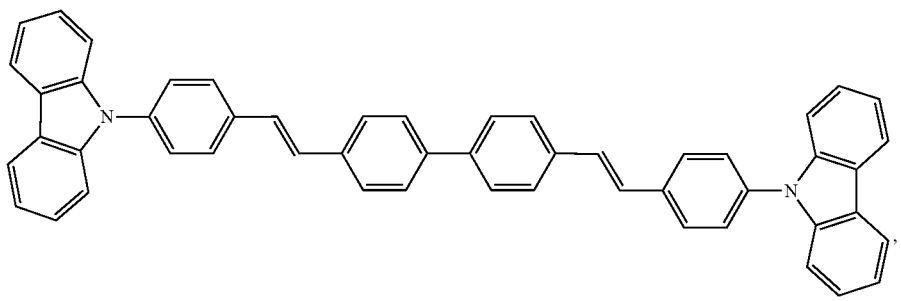

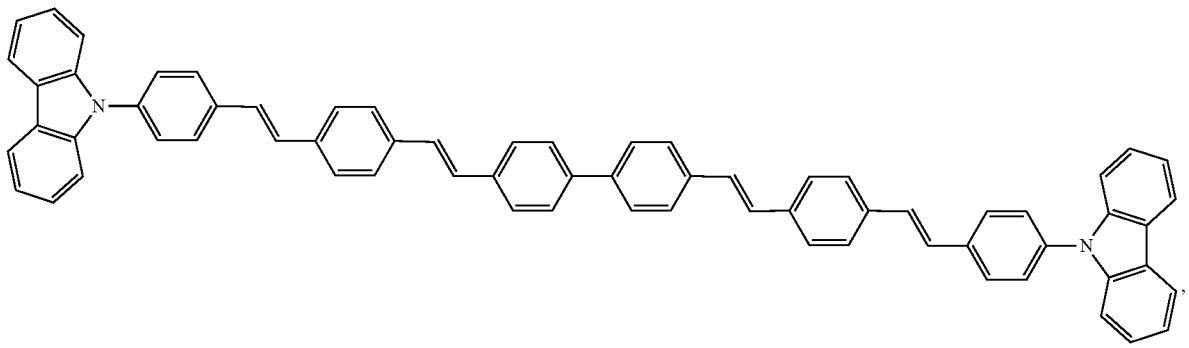

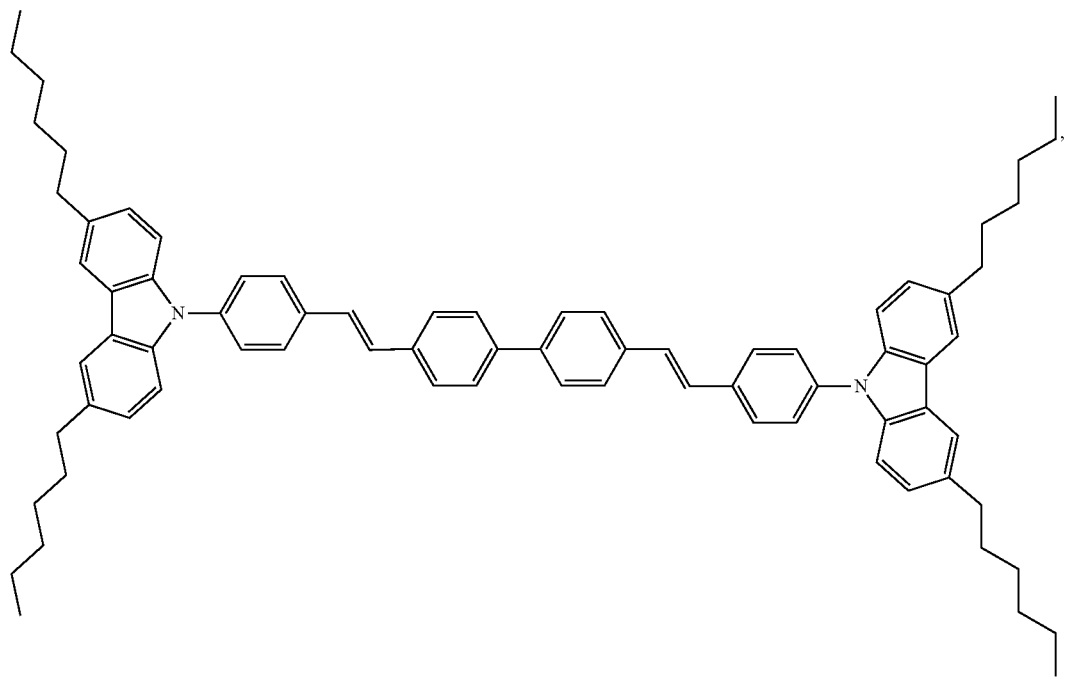
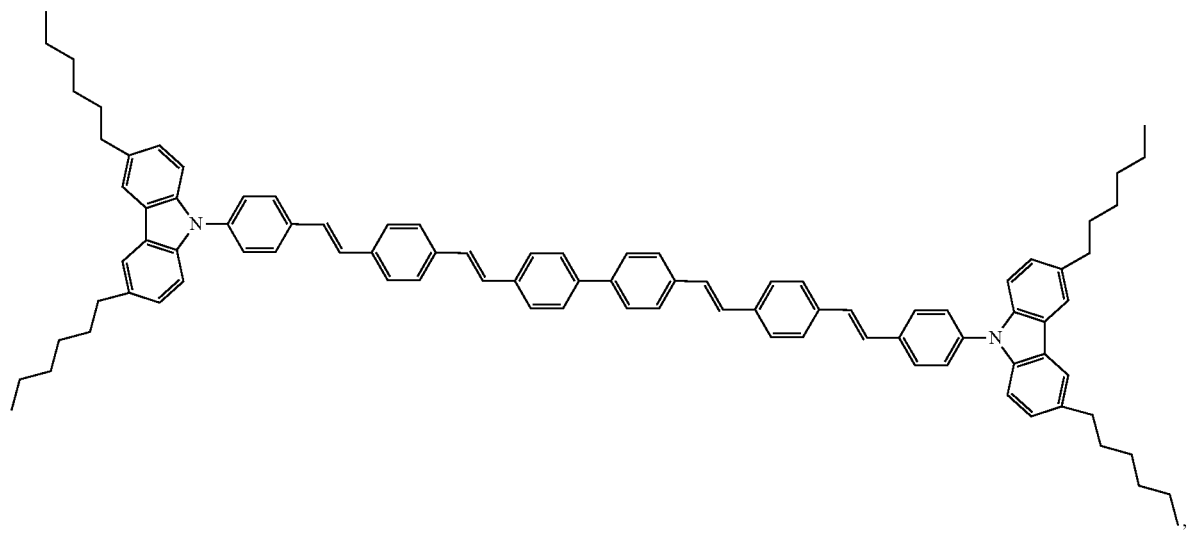
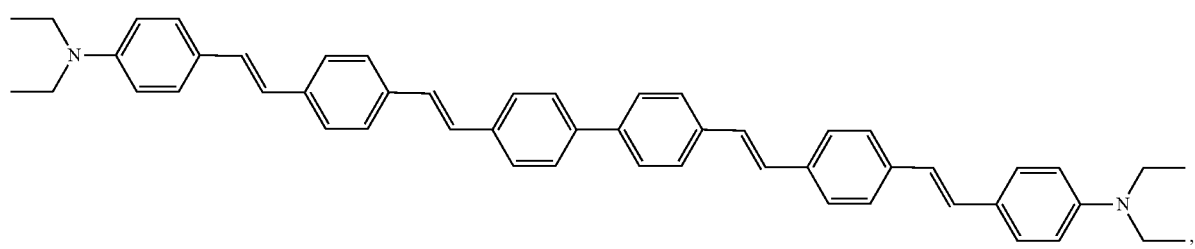
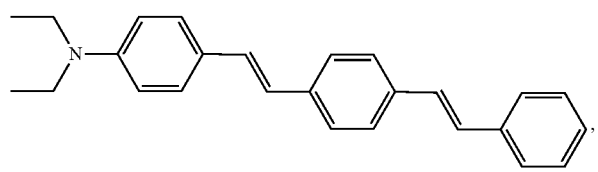

-continued
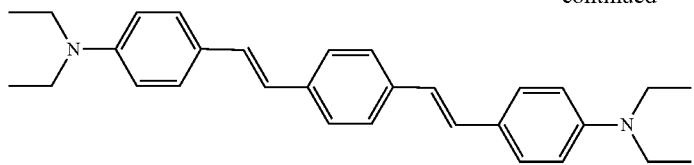
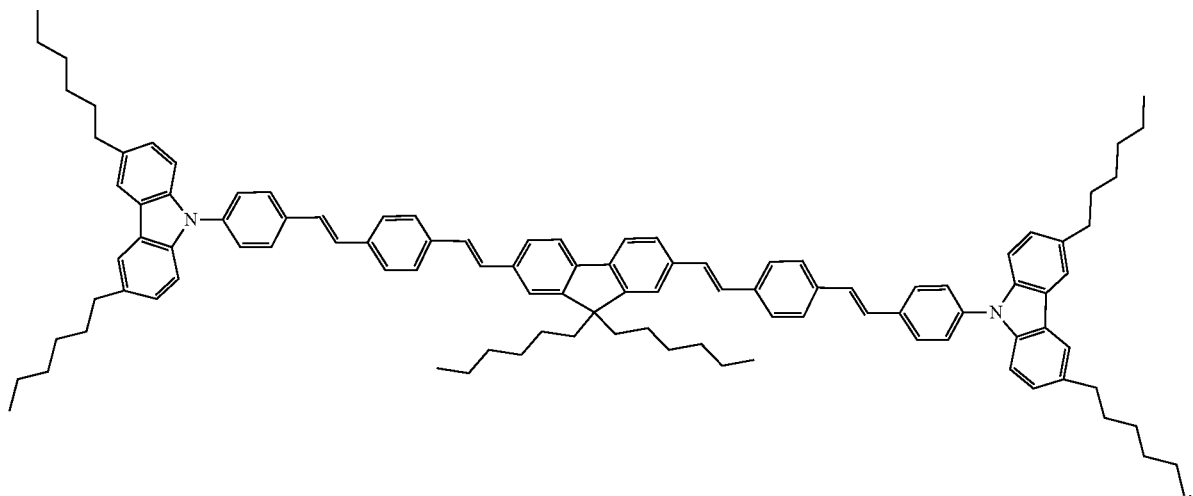
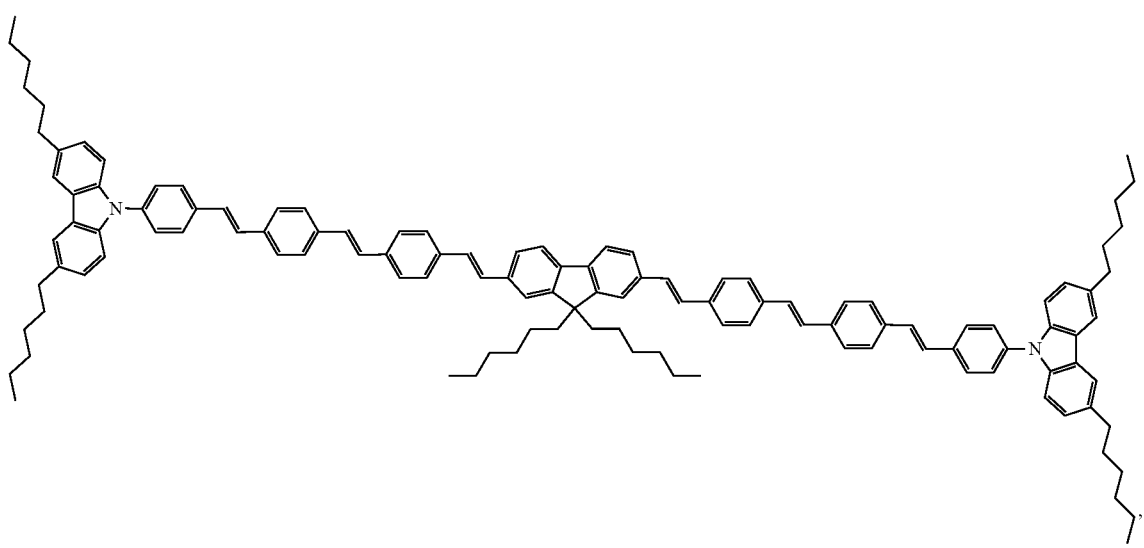
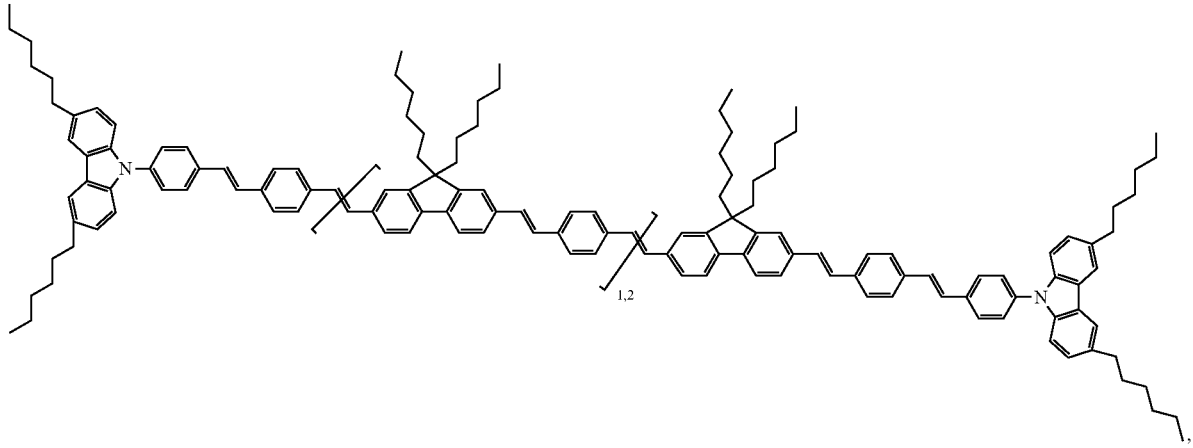

-continued

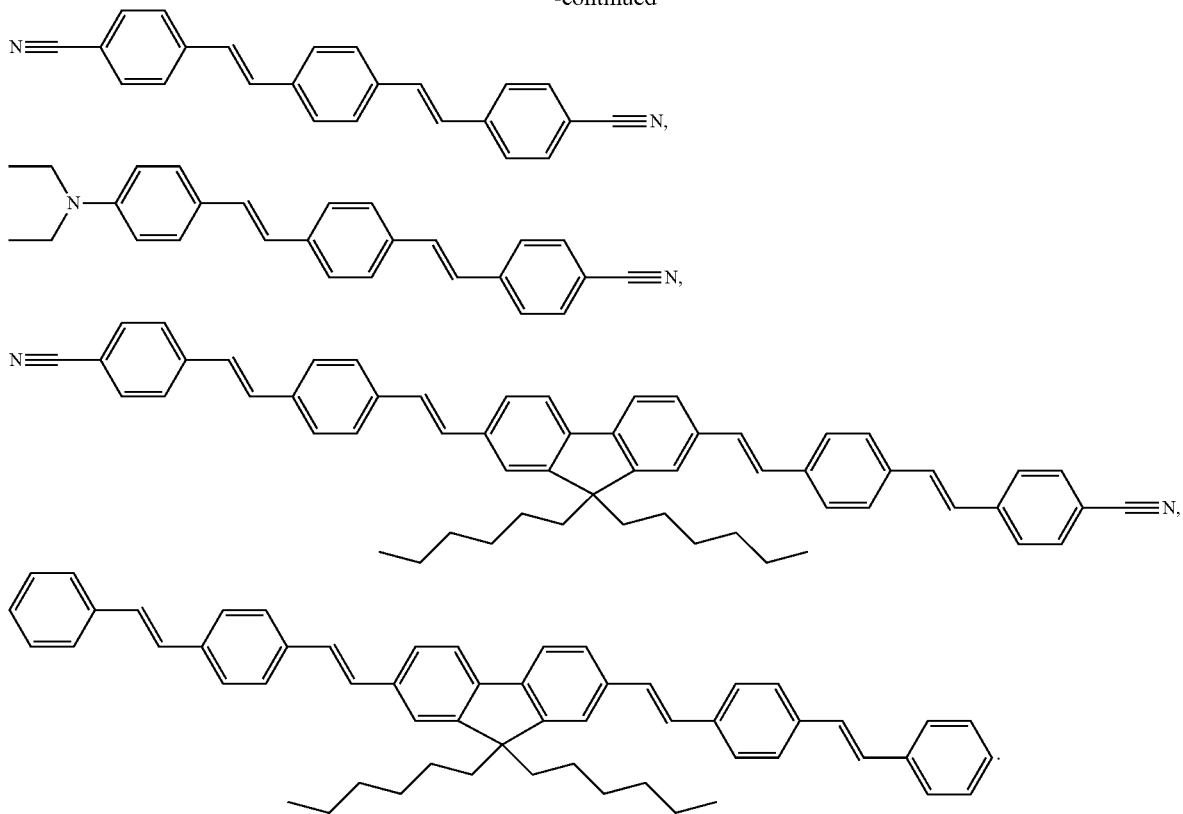

The present invention further relates to specific novel compounds of formula (I), marked as compounds of formula (I*)

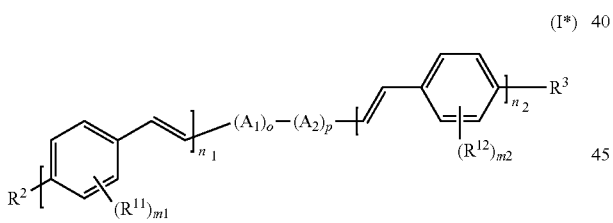

wherein
n1 and n2 are each independently 1, 2 or 3, preferably 1 or 2,
m1 and m2 are each independently 0, 1, 2, 3 or 4, preferably 0, 1 or 2, and
$R^{11}$ and $R^{12}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl, preferably H, unsubstituted or substituted $C_1$-$C_{20}$alkyl or unsubstituted or substituted $C_1$-$C_{20}$alkoxy,
$R^2$ and $R^3$ are each independently hydrogen, unsubstituted or substituted $C_1$-$C_{20}$alkyl or unsubstituted or substituted $C_1$-$C_{20}$alkoxy, unsubstituted or substituted $C_3$-$C_{20}$cycloalkyl, unsubstituted or substituted $C_6$-$C_{24}$aryl, an aliphatic heterocycle having a ring formed of 3 to 24 atoms; unsubstituted or substituted heteroaryl having a ring formed of 3 to 24 atoms; amino, CN, $CF_3$, $COOC_1$-$C_{20}$alkyl, $OCOC_1$-$C_{20}$alkyl or unsubstituted or substituted $C_7$-$C_{31}$alkaryl, wherein in the case that $A_2$ is a group of formula (3), $R^2$ and $R^3$ are not CN at the same time, and in the case that $A_2$ is a group of formula (2), the heteroaryl having a ring formed of 3 to 24 atoms is substituted by at least one $C_1$-$C_{20}$alkyl group;
$A_2$ is

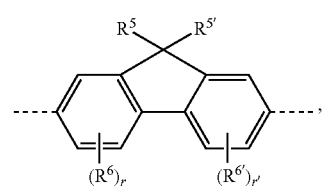

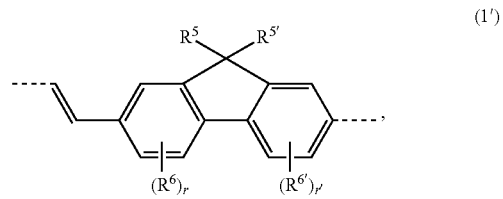

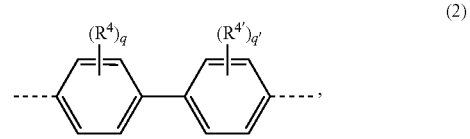

-continued

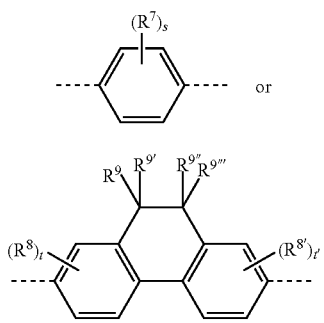

$A_1$ is

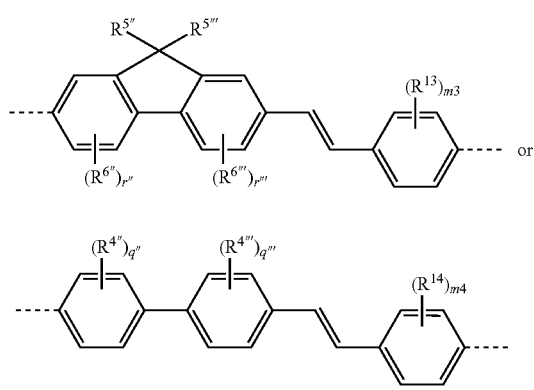

p is 1 or 2, preferably 1,
o is 0, 1 or 2,
q, q', q", q''', s, m3 and m4 are each independently 0, 1, 2, 3 or 4, preferably 0, 1 or 2,
r, r', r", r''', t and t' are each independently 0, 1, 2 or 3, preferably 0, 1 or 2,
$R^4$, $R^{4'}$, $R^{4''}$, $R^{4'''}$, $R^6$, $R^{6'}$, $R^{6''}$, $R^{6'''}$, $R^7$, $R^8$, $R^{8'}$, $R^{13}$ and $R^{14}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl,
$R^5$, $R^{5'}$, $R^{5''}$, $R^{5'''}$, $R^9$, $R^{9'}$, $R^{9''}$ and $R^{9'''}$ are each independently H or unsubstituted or substituted $C_1$-$C_{20}$alkyl, unsubstituted or substituted $C_6$-$C_{30}$aryl or unsubstituted or substituted $C_7$-$C_{31}$alkaryl,
wherein the dotted lines are bonding sites.

Preferred definitions of the residues, groups and indices of the novel compounds of formula (I*) are the same definitions as mentioned above concerning the compounds of formula (I).

The compounds of formula (I) and of formula (I*) are for example prepared by coupling a group of formula

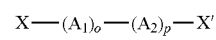 (II)

wherein $A_1$, $A_2$, o and p have been defined above and the dotted lines are bonding sites, with suitable groups for obtaining the units

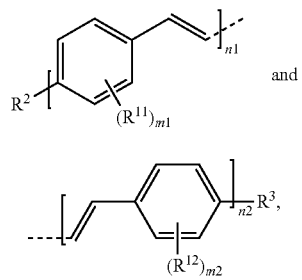

wherein
$R^2$, $R^3$, n1, n2, $R^{11}$, $R^{12}$, m1 and m2 have been defined above and the dotted lines are bonding sites. Suitable coupling methods are known by a person skilled in the art.

Preferably, phosphonic acid ester of the group of formula (II) (see formula (II*) below) are prepared from the corresponding halides in an Arbuzov reaction. Said phosphonic acid ester are—after deprotonation to the corresponding ylides—reacted with aldehydes based on formulae (III) and (IV) (see formulae (III*) and (IV*) below) in a Wittig Horner Wadsworth Emmons reaction.

The present invention therefore further relates to a process for the preparation of the novel compounds according to formula (I*) comprising the following step:

(i) Coupling a group of formula (II*)

$$X\text{---}(A_1)_o\text{---}(A_2)_p\text{---}X' \quad (\text{II*})$$

with a group of formula (III*) and a group of formula (IV*)

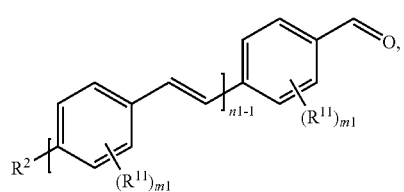

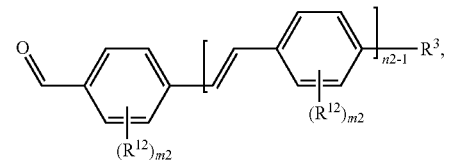

wherein
X and X' are each independently a phosphonic acid ester group (V)

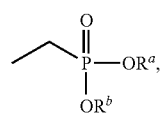

wherein $R^a$ and $R^b$ are each independently unsubstituted or substituted $C_1$-$C_{20}$alkyl, preferably unsubstituted or substituted $C_1$-$C_{20}$alkyl, more preferably ethyl, n1 and n2 are each independently 1, 2 or 3, preferably 1 or 2, m1 and m2 are each independently 0, 1, 2, 3 or 4, preferably 0, 1 or 2, and $R^{11}$ and $R^{12}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl, preferably H, unsubstituted or substituted $C_1$-$C_{20}$alkyl or unsubstituted or substituted $C_1$-$C_{20}$alkoxy, $R^2$ and $R^3$ are each independently hydrogen, unsubstituted or substituted $C_1$-$C_{20}$alkyl or unsubstituted or substituted $C_1$-$C_{20}$alkoxy, unsubstituted or substituted $C_3$-$C_{20}$cycloalkyl, unsubstituted or substituted $C_6$-$C_{24}$aryl, an aliphatic heterocycle having a unsubstituted or substituted ring formed of 3 to 24 atoms; unsubstituted or substituted heteroaryl having a ring formed of 3 to 24 atoms; amino, CN, $CF_3$, $COOC_1$-$C_{20}$alkyl, $OCOC_1$-$C_{20}$alkyl or unsubstituted or substituted $C_7$-$C_{31}$alkaryl, wherein in the case that $A_2$ is a group of formula (3), $R^2$ and $R^3$ are not CN at the same time, and in the case that $A_2$ is a group of formula (2) heteroaryl having a ring formed of 3 to 24 atoms is substituted by at least one $C_1$-$C_{20}$alkyl group;

$A_2$ is

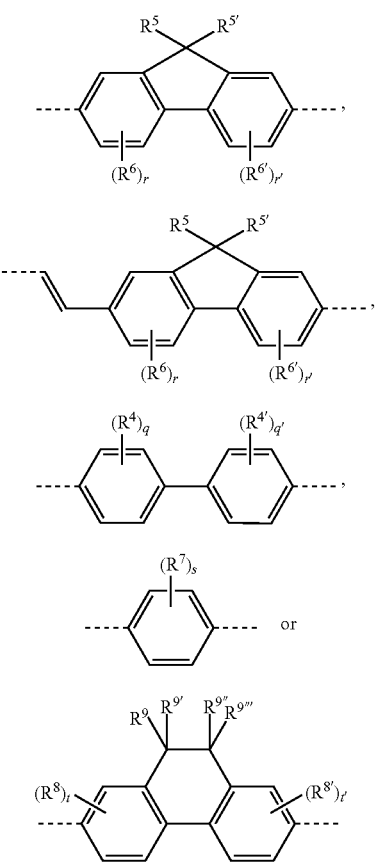

$A_1$ is

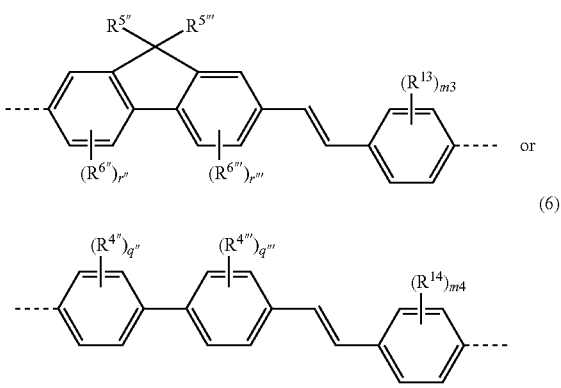

p is 1 or 2, preferably 1, o is 0, 1 or 2, q, q', q'', q''', s, m3 and m4 are each independently 0, 1, 2, 3 or 4, preferably 0, 1 or 2, r, r', r'', r''', t and t' are each independently 0, 1, 2 or 3, preferably 0, 1 or 2, $R^4$, $R^{4\prime}$, $R^{4\prime\prime}$, $R^{4\prime\prime\prime}$, $R^6$, $R^{6\prime}$, $R^{6\prime\prime}$, $R^{6\prime\prime\prime}$, $R^7$, $R^8$, $R^{8\prime}$, $R^{13}$ and $R^{14}$ are each independently H, unsubstituted or substituted $C_1$-$C_{20}$alkyl or unsubstituted or substituted $C_1$-$C_{20}$alkoxy, unsubstituted or substituted $C_6$-$C_{30}$aryl or unsubstituted or substituted $C_7$-$C_{31}$alkaryl, $R^5$, $R^{5\prime}$, $R^{5\prime\prime}$, $R^{5\prime\prime\prime}$, $R^9$, $R^{9\prime}$, $R^{9\prime\prime}$ and $R^{9\prime\prime\prime}$ are each independently H or unsubstituted or substituted $C_1$-$C_{20}$alkyl, unsubstituted or substituted $C_6$-$C_{30}$aryl or unsubstituted or substituted $C_7$-$C_{31}$alkaryl, wherein the dotted lines are bonding sites.

Preferred definitions of the residues, groups and indices mentioned in the process for preparing the novel compounds of formula (I*) are the same definitions as mentioned above concerning the compounds of formula (I).

Specific reaction conditions of the process are mentioned in the examples of the present application.

The compounds of formula (I) and formula (I*) of the present invention are characterized by short luminescence lifetimes. The luminescence lifetime (decay time, emissive lifetime $\tau_0$) is according to the present invention the quotient of the decay time measured (excited-state lifetime $\tau_\nu$) and the quantum yield of the luminescence, i.e. the emissive lifetime (luminescent lifetime) $\tau_0$ is calculated by $\tau_0 = \tau_\nu/QY$. The conditions of the measurement of QY, $\tau_0$ and $\tau_\nu$ are given in the example part.

Preferably, the luminescence lifetime $\tau_0$ of the compounds of formula (I) and formula (I*) of the present invention is 0.1 ns to 5 ns, more preferably 0.2 ns to 4.5 ns, further more preferably 0.3 ns to 4 ns, most preferably 0.4 ns to 3.5 ns It is a particular advantage of the compounds of formula (I) and formula (I*) of the present invention to have a very short luminescence lifetime (decay time). Such short luminescent lifetimes support high rates of data transmission.

Optical Data Communication System

In the optical data communication system according to the present invention an electrical signal is transformed to an optical signal in a transmitter. The modulated optical signal then propagates before arriving at a receiver. In the receiver, the optical signal is transformed back to an electrical signal.

Preferably, the optical data communication system according to the present invention is a free space optical data communication system. In said free space optical data communication system, the modulated optical signal propagates through a free-space path before arriving at a receiver.

The optical data communication system, preferably the free space optical data communication system, according to the present invention is useful in indoor as well as in outdoor environments. The general setup for optical data communication systems, preferably for free space optical data communication systems, for indoor and outdoor environment are known by a person skilled in the art and for example described in "Principles of LED light communications", S. Dimitrov, H. Haas, Cambridge University Press 2015, Chapter 2.1 to Chapter 2.4.

The optical data communication system according to the present invention preferably comprises
- at least one transmitter (T), and
- at least one receiver (R);
- wherein at least one compound of formula (I) or (I*) according to the present invention is present in the transmitter and/or receiver of the optical data communication system.

The present invention further relates to a receiver for an optical data communication system comprising at least one compound of formula (I) or (I*) according to the present invention, to a transmitter for an optical data communication system comprising at least one compound of formula (I) or (I*) according to the present invention, and to the use of a compound of formula (I) or (I*) according to the present invention in an optical data communication system.

Preferably, the optical data communication system according to the present invention comprises:
(i) an input (A),
(ii) a transmitter (T),
(iii) an optical path (C),
(iv) a receiver (R), and
(v) an output (E),
wherein at least one compound of formula (I) or (I*) according to the present invention is present in the transmitter and/or receiver of the optical data communication system.

In FIG. 1 a general example for an optical data communication system is shown. In FIG. 1:
A is an input (A),
B is a transmitter (T),
C is an optical path (C),
D is a receiver (R), and
E is an output (E).

Transmitter T

In the transmitter an electrical signal is transformed to an optical signal. Generally, transmitters useful in an optical data communication system, especially optical wireless communication (OWC) system, according to the present invention are known to a person skilled in the art. See for example "Principles of LED light communications", S. Dimitrov, H. Haas, Cambridge University Press 2015, Chapter 2.1 to Chapter 2.4.

In one embodiment of the present invention, at least one compound of formula (I) or (I*) according to the present invention is present in the transmitter.

The transmitter generally comprises a digital signal processor (DSP) with a digital-to-analog converter (DAC), which is employed for the modulation of the digital information bits (input (A)) and their transformation into an analog current signal. The current drives an optical emitter, i.e. a light source (L). In the case that the input (A) is already an analog signal, the conversion of the signal to an analog signal is omitted.

Light Source (L)

The light source (L) is usually either one or more light-emitting diodes (LED) or one or more laser diodes (LD), preferably one or more LEDs.

The light source (L) preferably generates white light. Suitable LEDs and LDs for generating white light are known by a person skilled in the art.

Suitable light sources (L) in the transmitter of the present invention are for example selected from the group consisting of an UV-LED, a phosphor converted white LED, an organic LED and a cool white LED, said cool white LED usually having a correlated color temperature between 4000 K and 20000 K. An UV-LED is a light emitting diode emitting ultraviolet electromagnetic radiation, i.e. electromagnetic radiation having wavelengths below 400 nm.

In one preferred embodiment of the present invention, phosphor converted LEDs, more preferably phosphor converted white LEDs, are employed as light source (L). In phosphor converted LEDs, light is generated based on wavelength (color) converters and LEDs.

Di-, tri- and tetrachromatic methods are adopted to optimize the wavelength for producing white light in phosphor converted white LEDs. Suitable di-, tri- and tetrachromatic methods for generating white light in LEDs are mentioned above (background of the invention). In said methods, one or more phosphors are employed as color converters. The color converter used in the transmitter in said embodiment of the present invention, preferably in the case when at least one compound of formula (I) or (I*) is used in the transmitter (preferably as at least one color converter), provides the advantage that modulated first electromagnetic radiation (emitted by a radiation source) is converted by a color converter into modulated second electromagnetic radiation, said second electromagnetic radiation may be in a desired spectral range.

The color converters mentioned above are usually employed in form of a frequency converter. Suitable frequency converters are described below.

Preferably, the light source (L) therefore comprises a radiation source (L1) for emitting a first electromagnetic radiation and a frequency converter (L2), comprising at least one color converter, for emitting a second electromagnetic radiation.

The first electromagnetic radiation preferably comprises at least a wavelength in a spectral range between 350 nm and 500 nm. Within this spectral range, cost efficient radiation sources are available. Suitable radiation sources, especially LEDs, are known by a person skilled in the art. Semiconductors useful for providing LEDs emitting in the spectral range between 350 nm and 500 nm ("blue") are known by a person skilled in the art and mentioned above. Furthermore, this spectral range is advantageous for conversion into a broader visible spectral range, in particular into white light. It is noted that the radiation source may emit only electromagnetic radiation that is in the above-mentioned spectral range or a part thereof. Furthermore, the radiation source may also emit electromagnetic radiation outside this spectral range as far as at least an emitted wavelength is within this spectral range.

The radiation sources (L1) used for the first electromagnetic radiation by the transmitter of the present invention, are the light sources mentioned above, i.e. one or more LEDs or one or more LDs, preferably one or more LEDs. Preferably, especially in the case when the compound of formula (I) or (I*) is used in the transmitter as phosphor (color converter), the radiation source is a light emitting diode (LED). In particular, the radiation source is a "blue" LED with a center wavelength of emission from 350 nm to 500 nm. A blue LED is a light emitting diode emitting blue light. However, generally also other radiation sources may be used that emit electromagnetic radiation with a center wavelength of emission between 350 nm and 500 nm.

Color Converter (Phosphor)

The color converter used in the transmitter in one embodiment of the present invention provides the advantage that modulated first electromagnetic radiation is converted into modulated second electromagnetic radiation, said second electromagnetic radiation may be in a desired spectral range. Therefore, the full bandwidth of a desired spectral range may be used for data transmission. Therefore, the distance and/or data transmission rate for such data transmission may be increased.

According to an embodiment of the transmitter of the present invention, the wavelength of the modulated second electromagnetic radiation is ranging from 380 nm to 750 nm. Therefore, visible light, in particular white light, that is emitted by the transmitter is directly generated by the color converter, so that no further elements for converting the color of the light are necessary if visible light shall finally be emitted.

A phosphor material is used to convert light emitted by one or more LEDs to broad spectrum white light. Suitable phosphor converted white LEDs are known by a person skilled in the art and generally described above.

Preferably, the color converter has a luminescence decay time in the range from 0.1 to 9 ns. It is a particular advantage of the above defined frequency converter to have a very short decay time. Such short decay times provide the advantage that the modulation of the converted electromagnetic radiation remains essentially unchanged, so that signal transmission is possible by means of the converted modulated electromagnetic radiation. All the longer the decay time is, the modulation of the first electromagnetic radiation is blurred, so that the signal transmission is negatively affected.

In one embodiment, the compound of formula (I) or (I*) is used as phosphor material (color converter). The compounds of formula (I) and (I*) are characterized by short luminescence lifetimes (decay times), preferably of 0.1 ns to 5 ns, more preferably 0.2 ns to 4.5 ns, further more preferably 0.3 ns to 4 ns, most preferably 0.4 ns to 3.5 ns.

Frequency Converter (L2)

The color converters mentioned above are usually employed in a frequency converter (L2).

In one embodiment, the present invention therefore relates to a frequency converter (L2) comprising at least one compound of formula (I) or (I*).

Preferably, the frequency converter (L2), comprising in one embodiment at least one compound of formula (I) or (I*), is arranged in a remote arrangement from the radiation source responsible for the first electromagnetic radiation. Preferably, the distance of the radiation source is in the range from 0.01 to 10 cm, preferably 0.1 to 8 cm. Such arrangement is also known as remote phosphor if the frequency converter is phosphor-based. According to this concept, the luminescent material (phosphor) is dissolved or dispersed in a polymeric matrix which is at a certain distance from the emitting LED chip. Therefore, the frequency converter is not directly applied to the radiation source. The life time of the frequency converter is advantageously extended by such remote arrangement.

If the frequency converters (L2) comprise more than one phosphor, it is possible in one embodiment of the invention for a plurality of phosphors to be present alongside one another in one layer.

In another embodiment, the various phosphors are present in various layers.

In a special embodiment, the frequency converter (L2) has a multi-layer structure, preferably a two-layer structure, wherein each layer comprises at least one phosphor. In this embodiment, one of the layers or more than one but not all of the layers or all of the layers comprise a scattering body. Suitable scattering bodies are described below. A preferred scattering body is $TiO_2$.

In one embodiment, the frequency converter (L2) consists of a plurality of polymer layers which have been laminated together to form a composite and wherein the various phosphors and/or scattering bodies may be present in different polymer layers. Suitable polymers for the polymer layers (polymeric matrix) are mentioned below.

In a further embodiment, at least one polymer layer of the frequency converter (L2) has been mechanically reinforced with glass fibers.

Suitable frequency converters (L2) may be in any desired geometric arrangement. The frequency converters may, for example, be in the form of films, sheets or plaques. Equally, the matrix containing phosphors may be in droplet form or hemispherical form or in the form of lenses with convex and/or concave, flat or spherical surfaces. "Casting" refers to the embodiment, where LEDs or components comprising LEDs are cast or enveloped fully with a polymer comprising at least one phosphor. In one embodiment of the invention, the polymer layers (matrices) comprising at least one phosphor are 25 to 1000 micrometers (μm) thick, preferably 35 to 400 μm and particularly 50 to 300 μm.

In another embodiment, the polymer layers comprising at least one phosphor are 0.2 to 5 mm thick, preferably 0.3 to 3 mm and more preferably 0.4 to 1 mm.

If the frequency converters (L2) consist of one layer or they have a laminate structure, the individual layers, in a preferred embodiment, are continuous and do not have any holes or interruptions.

Polymeric Matrix Material

As mentioned before, the color converter, in one embodiment the compound of formula (I) or (I*), is preferably arranged as remote phosphor. According to this concept, the luminescent material (phosphor) is dissolved or dispersed in a polymeric matrix.

The present invention therefore also relates to a composition comprising a polymeric material and at least one compound of formula (I) or (I*). Suitable and preferred compounds of formula (I) and (I*) are mentioned above and suitable and preferred polymeric materials are the polymeric matrix materials mentioned below.

The polymeric matrix for the frequency converter (phosphor) according to the present invention is preferably selected from the group consisting of polystyrene, polycarbonate, polymethyl-methacrylate, polyvinylpyrrolidone, polymethacrylate, polyvinyl acetate, polyvinyl chloride, poly-butene, silicone, polyacrylate, epoxy resin, polyvinyl alcohol, poly(ethylene vinylalcohol)-copolymer (EVA, EVOH), polyacrylonitrile, polyvinylidene chloride (PVDC), polystyrene acrylonitrile (SAN), polybutylene terephthalate (PBT), polyethylene terephthalate (PET), polyvinyl butyrate (PVB), polyvinyl chloride (PVC), polyamides, polyoxymethylenes, polyimides, polyetherimides, 2,5-furandicarboxylate polyester and mixtures thereof. In one embodiment of the present invention, at least one compound of formula (I) or (I*) is employed as color converter.

Preferably, the polymeric matrix material comprises at least one polymer selected from polystyrene, polycarbonate, polyethylene terephthalate and mixtures thereof.

Polystyrene is understood here to mean, inter alia, all homo- or copolymers which result from polymerization of styrene and/or derivatives of styrene. Derivatives of styrene are, for example, alkylstyrenes such as alpha-methylstyrene, ortho-, meta-, para-methylstyrene, para-butylstyrene, especially para-tert-butylstyrene, alkoxystyrene such as para-methoxystyrene, para-butoxystyrene, para-tert-butoxystyrene. In general, suitable polystyrenes have a number average molecular weight Mn of 10000 to 1000000 g/mol (determined by GPC), preferably 20000 to 750000 g/mol, more preferably 30000 to 500000 g/mol.

In one preferred embodiment of the invention, the polymeric matrix of the frequency converter comprises or is a homopolymer of styrene or styrene derivatives. More particularly, the polymeric matrix consists of polystyrene.

In a further preferred embodiment of the invention, the polymeric matrix comprises or is a styrene copolymer, which is likewise regarded as polystyrene in the context of this application.

Styrene copolymers may comprise, as further constituents, for example, butadiene, acrylonitrile, maleic anhydride, vinylcarbazole or esters of acrylic, methacrylic or itaconic acid as monomers.

Suitable styrene copolymers generally comprise at least 20% by weight of styrene, preferably at least 40% and more preferably at least 60% by weight of styrene. In another embodiment, they comprise at least 90% by weight of styrene.

Preferred styrene copolymers are styrene-acrylonitrile copolymers (SAN) and acrylonitrile-butadiene-styrene copolymers (ABS), styrene-1,1'-diphenylethene copolymers, acrylic ester-styrene-acrylonitrile copolymers (ASA), methyl methacrylate-acrylonitrile-butadiene-styrene copolymers (MABS). A further preferred polymer is alpha-methylstyrene-acrylonitrile copolymer (AMSAN). The styrene homo- or copolymers can be prepared, for example, by free-radical polymerization, cationic polymerization, anionic polymerization or under the influence of organometallic catalysts (for example Ziegler-Natta catalysis). This can lead to isotactic, syndiotactic or atactic polystyrene or copolymers. They are preferably prepared by free-radical polymerization. The polymerization can be performed as a suspension polymerization, emulsion polymerization, solution polymerization or bulk polymerization. The preparation of suitable polystyrenes is described, for example, in Oscar Nuyken, Polystyrenes and Other Aromatic Polyvinyl Compounds, in Kricheldorf, Nuyken, Swift, New York 2005, p. 73-150 and references cited therein; and in Elias, Macromolecules, Weinheim 2007, p. 269-275.

In another preferred embodiment, the polymeric matrix comprises or is polyethylene terephthalate. Polyethylene terephthalate is obtainable by condensation of ethylene glycol with terephthalic acid.

In a further preferred embodiment, the polymeric matrix comprises or is polycarbonate. Polycarbonates are polyesters of carbonic acid with aromatic or aliphatic dihydroxyl compounds. Preferred dihydroxyl compounds are, for example, methylenediphenylenedihydroxyl compounds, for example bisphenol A. One means of preparing polycarbonates is the reaction of suitable dihydroxyl compounds with phosgene in an interfacial polymerization. Another means is the reaction with diesters of carbonic acid such as diphenyl carbonate in a condensation polymerization. The preparation of suitable polycarbonates is described, for example, in Elias, Macromolecules, Weinheim 2007, p. 343-347.

In a further preferred embodiment, the polymeric matrix comprises at least one 2,5-furandicarboxylate polyester (A) obtainable by reacting (i) at least one diol selected from an aliphatic $C_2$-$C_{20}$-diol and a cycloaliphatic $C_3$-$C_{20}$-diol, with (ii) 2,5-furandicarboxylic acid and/or an ester forming derivative thereof and (iii) optionally at least one further dicarboxylic acid selected from 1,2-cyclohexanedicarboxylic acid, 1,4-cyclohexanedicarboxylic acid, 3,4-furandicarboxylic acid, terephthalic acid and 2,5-naphthalic acid and/or an ester forming derivative thereof.

Suitable aliphatic $C_2$-$C_{20}$-diols are preferably linear or branched $C_2$-$C_{15}$-alkanediols, especially linear or branched $C_2$-$C_{10}$-alkanediols, such as ethane-1,2-diol (ethylene glycol), propane-1,2-diol, propane-1,3-diol (propylene glycol), butane-1,3-diol, butane-1,4-diol (butylene glycol), 2-methyl-1,3-propanediol, pentane-1,5-diol, 2,2-dimethyl-1,3-propanediol (neopentyl glycol), hexane-1,6-diol, heptane-1,7-diol, octane-1,8-diol, nonane-1,9-diol, decane-1,10-diol, etc. Suitable cycloaliphatic $C_3$-$C_{20}$-diols are preferably $C_3$-$C_{10}$-cycloalkylenediols, such as 1,2-cyclopentanediol, 1,3-cyclopentanediol, 1,2-cyclohexanediol, 1,4-cyclohexanediol, 1,2-cycloheptanediol or 1,4-cycloheptanediol. Other suitable cycloaliphatic $C_3$-$C_{20}$-diols include 1,3-cyclohexane dimethanol and 1,4-cyclohexane dimethanol, or 2,2,4,4-tetramethyl-i1,3-cyclobutanediol, or combinations thereof. Particularly preferred diols are $C_2$-$C_6$-alkanediols, in particular ethane-1,2-diol, propane-1,2-diol, propane-1,3-diol, butane-1,3-diol, butane-i1,4-diol, pentane-1,5-diol, 2,2-dimethyl-1,3-propanediol and mixtures thereof. More particularly preferred are ethane-1,2-diol and propane-1,3-diol. Especially preferred is ethane-1,2-diol.

More particularly preferred are also biologically derived ("bio-derived") $C_2$-$C_{10}$-alkanediols, especially $C_2$-$C_6$-alkanediols, such as ethane-1,2-diol and propane-1,3-diol. Bio-based ethane-1,2-diol may be obtained from a lignocellulosic biomass source by the conversion of the carbohydrates therein contained. Methods for preparing $C_2$-$C_{10}$-alkanediols from biomass are known in the art, for example from US 2011/0306804.

Preferably, the diol component (i) is made up exclusively of one diol mentioned as preferred, especially ethane-1,2-diol. The diol component (i) may also comprise two, three or more than three different diols. If two, three or more than three different diols are used, preference is given to those mentioned above as being preferred. In this case, based on the total weight of component (i), ethane-1,2-diol is preferably the major component.

Ester forming derivatives of 2,5-furandicarboxylic acids are especially $C_1$-$C_{10}$-dialkyl esters of 2,5-furandicarboxylic acid. Particularly preferred diesters are $C_1$-$C_6$-dialkyl esters of 2,5-furandicarboxylic acid, especially the dimethyl ester and diethyl ester. Component (ii) may also comprise two, three or more than three different diesters of 2,5-furandicarboxylic acid. 2,5-Furandicarboxylic acid can be produced from bio-based sugars. Routes for the preparation of 2,5-furandicarboxylic acid using air oxidation of 2,5-disubstituted furans, such as 5-hydroxymethylfurfural with catalysts comprising Co, Mn and/or Ce were reported recently in WO 2010/132740, WO 2011/043660, WO 2011/043661, US 2011/0282020, US 2014/0336349 and WO 2015/137804.

Routes for the preparation of dialkyl esters of 2,5-furandicarboxylic acid are also described for example in WO 2011/043661.

Preferably, component (ii) is made up exclusively of 2,5-furandicarboxylic acid or of diester(s) of 2,5-furandicarboxylic acid.

Preferably, the 2,5-furandicarboxylate polyester (A) is selected from poly(ethylene-2,5-furandicarboxylate), poly(propylene-2,5-furandicarboxylate), poly(ethylene-co-propylene-2,5-furandicarboxylate), poly(butylene-2,5-furandicarboxylate), poly(pentylene-2,5-furandicarboxylate), poly(neopentylene-2,5-furandicarboxylate) and mixtures thereof.

In particular, the polymeric matrix material for use in combination with the frequency converter according to the invention, in one embodiment the compound of formula (I) or (I*), is selected from the group consisting of poly(ethylene-2,5-furandicarboxylate), poly(trimethylene-2,5-furan-dicarboxylate) and poly(butylene-2,5-furandicarboxylate). More preferably, the polymeric matrix material for use in combination with the frequency converter according to the invention, in one embodiment the compound of formula (I) or (I*), is poly(ethylene-2,5-furandicarboxylate).

In a further specific embodiment, the polymeric matrix material for use in combination with the frequency converter, in one embodiment the compound of formula (I) or (I*), comprises a mixture (blend) of different 2,5-furandicarboxylate polyesters (A) as defined above, for example, a blend of poly(ethylene-2,5-furandicarboxylate) and poly(propylene-2,5-furandicarboxylate) Poly(propylene-2,5-furandicarboxylate) is also referred to as poly(trimethylene-2,5-furandicarboxylate); poly(butylene-2,5-furandicarboxylate) is also referred to as poly(tetramethylene-2,5-furan-dicarboxylate), poly(pentylene-2,5-furandicarboxylate) is also referred to as poly(pentamethylene-2,5-furan-dicarboxylate).

Likewise suitable are 2,5-furandicarboxylate polyesters (A) obtainable by reacting at least one diol component (i) as defined above, component (ii) as defined above and at least one further diacid or diester component (iii) selected from 1,2-cyclohexane-dicarboxylic acid, 1,4-cyclohexanedicarboxylic acid, 3,4-furandicarboxylic acid, terephthalic acid and 2,6-naphthalic acid and/or an ester forming derivative thereof. Ester forming derivatives of 1,2-cyclohexanedicarboxylic acid, 1,3-cyclohexanedicarboxylic acid, 3,4-furandicarboxylic acid, terephthalic acid and 2,5-naphthalic acid are especially the $C_1$-$C_{10}$-dialkyl ester. Particularly preferred esters are $C_1$-$C_6$-dialkyl ester, especially the dimethyl ester and diethyl ester. When using a combination of component (ii) and component (iii), component (ii) is usually the major component based on the total weight of component (ii) and (iii). Examples are poly(ethylene-2,5-furandicarboxylate-co-1,2-cyclohexanedicarboxylate), poly(ethylene-2,5-furandicarboxylate-co-1,4-cyclohexanedicarboxylate), poly(ethylene-2,5-furandicarboxylate-co-terephthalate), poly(ethylene-2,5-furandicarboxylate-co-2,5-naphthalate) or poly(ethylene-2,5-furandicarboxylate-co-3,4-furandicarboxylate), preferably poly(ethylene-2,5-furandicarboxylate-co-terephthalate), poly(ethylene-2,5-furandicarboxylate-co-2,6-naphthalate) or poly(ethylene-2,5-furandicarboxylate-co-3,4-furandicarboxylate.

The 2,5-furandicarboxylate polyester (A) can be prepared as described in U.S. Pat. No. 2,551,731.

In a preferred embodiment, polymers which have been polymerized with exclusion of oxygen are used. Preferably, the monomers during the polymerization comprised a total of not more than 1000 ppm of oxygen, more preferably not more than 100 ppm and especially preferably not more than 10 ppm.

In one embodiment of the invention, suitable polymers are optically transparent polymers. In another embodiment, suitable polymers are opaque polymers.

In the meaning of the present application optically transparent means completely optically transparent as well semi-transparent. Therefore, optically transparent means that at least 30% of the incident light enter through the polymer, preferably 30% to 100%, more preferably at least 50%, even more preferably 50% to 100%, most preferably at least 80%, even more most preferably 80% to 100%.

The transparency (light transmission) of at least 30%, preferably 30% to 100%, more preferably at least 50%, even more preferably 50% to 100%, most preferably at least 80%, even more most preferably 80% to 100% is preferably determined as light transmission TL (380-780 nm) based on EN 410.

Opaque polymers do not allow transmission of light waves. In other words, one cannot see through an opaque polymer. Opacity occurs because of the reflection of light waves off the surface of a polymer.

Suitable matrix polymers may comprise, as further constituents, additives, such as flame retardants, antioxidants, light stabilizers, UV absorbers, free-radical scavengers, antistats. Stabilizers of this kind are known to those skilled in the art.

Suitable antioxidants or free-radical scavengers are, for example, phenols, especially sterically hindered phenols, such as butylhydroxyanisole (BHA) or butylhydroxytoluene (BHT), or sterically hindered amines (HALS). Stabilizers of this kind are sold, for example, by BASF under the Irganox® trade name. In some cases, antioxidants and free-radical scavengers can be supplemented by secondary stabilizers, such as phosphites or phosphonites, as sold, for example, by BASF under the Irgafos® trade name.

Suitable UV absorbers are, for example, benzotriazoles, such as 2-(2-hydroxyphenyl)-2H-benzotriazole (BTZ), triazines, such as (2-hydroxyphenyl)-s-triazine (HPT), hydroxybenzophenones (BP) or oxalanilides. UV absorbers of this kind are sold, for example, by BASF under the Uvinul® trade name.

In a preferred embodiment of the invention, suitable matrix polymers do not comprise any antioxidants or free-radical scavengers.

The concentration of the color converters, in one embodiment the compounds of formula (I) or (I*), in the polymer matrix is set as a function of the thickness of the frequency converter and the type of polymer. If a thin polymer layer is used, the concentration of the organic fluorescent colorant(s) is generally higher than in the case of a thick polymer layer. Typically, the amount of color converters, in one embodiment the compounds of formula (I) or (I*), in the matrix polymer also depends on the correlated color temperature CCT to be achieved. A skilled person will appreciate that by increasing the concentration of yellow fluorescent colorant(s) and red fluorescent colorant(s), the light emitted from the LED is tuned to longer wavelength to obtain white light with a required CCT.

Typically, the concentration of the red colorant(s) is usually in the range from 0.0001 to 0.5% by weight, preferably 0.001 to 0.1% by weight, based on the amount of matrix polymer used. The concentration of (a) yellow or yellow-green colorant(s) typically is 0.002 to 0.5% by weight, preferably 0.003 to 0.4% by weight, based on the amount of the matrix polymer used.

It may be advantageous, for example in view of CCT or color rendering index (CRI), to use a mixture of yellow colorant(s) and red colorant(s). The ratio of yellow or yellow-green emitting colorant(s) to red colorant(s) is typically in the range from 1:1 to 25:1, preferably 2:1 to 20:1, more preferably 2:1 to 15:1, such as 10:1 or 3:1 or 4:1. A skilled person will readily appreciate that the ratio of the colorants depends on the chosen light source. For a desired CCT, the ratio of yellow colorant/red colorant is much greater, if the light is generated by a blue LED with a center wavelength of emission between 420 nm and 480 nm in comparison to the ratio of yellow colorant/red colorant if the light is generated by a white LED having a CCT between 6 000 to 20 000 K.

Pigments/Scattering Bodies

In a special embodiment, the color converter, in one embodiment the compound of formula (I) or (I*), is additionally employed with at least scattering body. Preferably, the color converter is additionally employed with at least one inorganic white pigment as a scattering body.

The present invention therefore further relates to a composition comprising at least one compound of formula (I) or (I*) and at least one scattering body. Suitable and preferred compounds of formula (I) and (I*) are mentioned above and suitable and preferred scattering bodies are mentioned below.

Preferably, the composition comprises at least one compound of formula (I) or (I*), at least one polymeric material and at least one scattering body. Suitable and preferred polymeric materials are the polymeric matrix materials mentioned above.

Suitable scattering bodies are inorganic white pigments, for example titanium dioxide, barium sulfate, lithopone, zinc oxide, zinc sulfide, calcium carbonate with a mean particle size to DIN 13320 of 0.01 to 10 µm, preferably 0.1 to 1 µm, more preferably 0.15 to 0.4 µm, especially scattering bodies based on $TiO_2$.

Scattering bodies are included in a composition comprising at least one color converter, at least one polymeric matrix and at least one scattering body typically in an amount of 0.01 to 2.0% by weight, preferably 0.05 to 1% by weight, more preferably 0.1 to 0.5% by weight, based in each case on the polymeric matrix.

Examples of suitable light scattering organic agents include those based on poly(acrylates); poly (alkyl methacrylates), for example poly(methyl methacrylate) (PMMA); poly (tetrafluoroethylene) (PTFE); silicone-based scattering agents, for example hydrolyzed poly(alkyl trialkoxysilanes), and mixtures thereof. The size of these light scattering agents (average diameter-weight average) is usually in the range from 0.5 to 50 µm, preferably 1 to 10 µm. These scattering agents are typically included in an amount of 1 to 10% by weight, based in each case on the polymer of the layer comprising scattering bodies. Useful scattering agents are for example a mixture of 3 to 5% by weight of PMMA based scattering agent and 1.5 to 2% by weight of silicone base scattering agent.

Also suitable are light-scattering compositions which contain polymeric particles based on vinyl acrylate with a core/shell morphology in combination with $TiO_2$ as described in EP-A 634 445.

Preferably, the at least one scattering agent is a poly (methyl methacrylate)-based scattering agent, silicone-based scattering agent or $TiO_2$.

The frequency converters (L2) may optionally comprise further constituents, such as a backing layer.

Backing layers serve to impart mechanical stability to the frequency converter. The type of material for the backing layers is not crucial, provided that it is transparent and has the desired mechanical strength. Suitable materials for backing layers are, for example, glass or transparent rigid organic polymers, such as polycarbonate, polystyrene or polymethacrylates or polymethyl methacrylates.

Backing layers generally have a thickness of 0.1 mm to 10 mm, preferably 0.2 mm to 5 mm, more preferably 0.3 mm to 2 mm.

In one embodiment of the invention, the frequency converters (L2) have at least one barrier layer against oxygen and/or water, as disclosed in WO 2012/152812. Examples of suitable barrier materials for barrier layers are, for example, glass, quartz, metal oxides, $SiO_2$, a multilayer system composed of alternating layers of $M_2O_3$ and $SiO_2$ layers, titanium nitride, $SiO_2$/metal oxide multilayer materials, polyvinyl alcohol, polyacrylonitrile, polyvinylidene chloride (PVDC), liquid crystal polymers (LCP), polystyrene-acrylonitrile (SAN), polybutylene terephthalate (PBT), polybutylene naphthalate (PBN), polyethylene terephthalate (PET), polyethylene naphthalate (PEN), polyvinyl butyrate (PBT), polyvinyl chloride (PVC), polyamides, polyoxymethylenes, polyimides, polyetherimides, epoxy resins, polymers which derive from ethylene-vinyl acetate (EVA) and polymers which derive from ethylene-vinyl alcohol (EVOH).

A preferred material for barrier layers is glass or a multilayer system composed of alternating layers of $AlO_3$ and $SiO_2$ layers.

Preferably, suitable barrier layers have low permeability for oxygen.

More preferably, suitable barrier layers have low permeability for oxygen and water.

The preparation of the frequency converter (L2) is generally known by a person skilled in the art. In particular, the frequency converter present in a remote arrangement is formed by extrusion, printing, coating or molding.

The radiation source (L1) and the frequency converter (L2) are preferably arranged within a housing. The housing is partly transparent for electromagnetic radiation to be emitted by the transmitter. The frequency converter (L2) is applied to the inside surface of the transparent part of the housing.

The light, preferably white light, generated by the frequency converter (L2) is the second electromagnetic radiation finally emitted by the transmitter (T). The transmitter (T) therefore usually emits electromagnetic radiation in the visible spectral range.

The value of the luminous flux of the second electromagnetic radiation, i.e. preferably of the white light, is preferably at least in the range from 100 lm to 30 000 lm. Therefore, in a preferred embodiment of the present invention, an optical data communication system is formed comprising the transmitter (T) for transmitting data on the one hand and for emitting illumination light on the other hand. Such optical data communication system may be used wherever a luminaire, a lamp or any other lighting device may conventionally be used.

In addition, the light source of the transmitter (T) may also be dimmed, so that a lower luminous flux that is not perceptible may also be generated, so that data transmission may also be carried out when the illumination device is not used for lighting.

Modulator (M)

Furthermore, the transmitter (T) comprises a modulator (M), preferably being adapted to modulate the first electromagnetic radiation emitted by the radiation source (L1) depending on data to be transmitted.

The modulator (M) is coupled to the input (A). The input (A) transfers the data to be transmitted to the modulator (M) that converts such data into a modulation signal.

For example, a blue LED forming the radiation source (L1) emits blue light as first electromagnetic radiation that is modulated in accordance with the data to be transmitted. Such modulated blue light is converted by the frequency converter (L2) into modulated white light that forms modulated second electromagnetic radiation.

The second electromagnetic radiation is modulated in correspondence to the modulation of the first electromagnetic radiation, i.e. the modulation used for data transmission is maintained by the frequency converter (L2).

Optical carrier modulation and demodulation are usually achieved through intensity modulation for example with direct detection (IM/DD). The desired waveform is modulated onto the instantaneous power of the optical carrier, and the detector generates a current proportional to the received instantaneous power; that is, only the intensity of the optical wave is detected, and there is no frequency or phase information (as for example mentioned H. Elgala et al., Indoor optical wireless communication: Potential and state-of-the-art, TOPICS IN OPTICAL COMMUNICATIONS, Article in IEEE Communications Magazine October 2011).

Suitable modulation technics are for example also described in H. Elgala et al., Indoor optical wireless communication: Potential and state-of-the-art, TOPICS IN OPTICAL COMMUNICATIONS, Article in IEEE Communications Magazine October 2011: High average power efficiency can be achieved by employing single-carrier (SC) pulsed modulation techniques in which the time-dependent characteristics of the optical pulse is used to convey information. Among several techniques, two schemes are widely used, on-off keying (OOK) and pulse-position modulation (PPM). OOK is one of the oldest formats and is the simplest in terms of hardware implementation and integration. It also exhibits a good compromise between complexity and performance. In PPM, an optical pulse is transmitted in one out of S slots per symbol time. The occupied slot position denotes the bit combination conveyed by the symbol. PPM expands the signal bandwidth compared to OOK, but provides higher power efficiency. Besides, the use of PPM imposes more system complexity than OOK since both slot- and symbol-level synchronizations, critical to system performance, are required at the receiver.

Multiple-Subcarrier Modulation MSM techniques for OW (optical wireless) links are also generally suitable. OFDM is a practical realization of multiple-subcarrier modulation (MSM). OFDM is a parallel data transmission scheme in which high data rates can be achieved by transmitting orthogonal subcarriers. OFDM systems do not require complex channel equalizers, the time-varying channel can easily be estimated using frequency-domain channel estimation, and adaptive modulation can be applied based on the uplink/downlink (UL/DL) requested data rates and quality of service (QoS). Also, the possibility to combine OFDM with any multiple access scheme makes it an excellent preference for indoor OW applications.

As mentioned above, according to the present invention, preferably the first electromagnetic radiation is modulated. Such modulation may be implemented by control of the radiation source.

According to another embodiment, the first electromagnetic radiation may also be modulated after this radiation has been emitted by the radiation source but before conversion into the second electromagnetic radiation. In this case, the modulator (M) is arranged between the radiation source and the frequency converter.

According to even another embodiment, the modulator (M) may be coupled to the frequency converter if the frequency converter is an active element that may be controlled. However, also in this case, the modulation is carried out before the conversion of the first electromagnetic radiation.

According to the invention, the frequency converter is preferably adapted, so that the second electromagnetic radiation is modulated in correspondence to the modulation of the first electromagnetic radiation. In particular, the modulation remains essentially unchanged due to the preferred short decay time of the frequency converter used by the transmitter according to the present invention.

Receiver (R)

The optical data communication system comprises in addition a receiver to detect at least a part of the modulated electromagnetic radiation emitted by the transmitter (T). The receiver (R) may comprise a detector, for example photodetector (photodiode), a camera or a solar cell, such as a camera of a computer or smartphone, preferably a photodetector. The photodetector may be a photodetector (PD) or an array of PDs. At the detector, preferably the photodetector, the optical signal is converted back to electrical current.

The receiver (R) is usually located to be irradiated by the modulated electromagnetic radiation.

The current signal may be electronically pre-amplified by means of a transimpedance amplifier (TIA), which is optionally present in the receiver. The transimpedance amplifier (TIA) is preferably coupled to the output of the detector.

The receiver (R) usually further comprises a data analyzer that is coupled to the detector, preferably the photodiode, respectively to the optionally present TIA. The data analyzer is adapted to extract data from the detected modulated electromagnetic radiation as it is known in the art. The data analyzer may comprise for example a digital signal processor (DSP) with an analog-to-digital converter (ADC) for transformation of the analog current signal into a digital signal and demodulation of the information bits. The demodulated information bits form the output (E). In the case that the output (E) is digital signal, the conversion of the signal to a digital signal is omitted.

Further, an optical filter may be arranged before the detector, preferably the photodiode (PD or array of PDs), to select the modulated electromagnetic radiation emitted by the transmitter (T) in the optical spectrum. In addition, the optical filter greatly reduces the interference from ambient light.

To collect the modulated electromagnetic radiation and concentrate it onto a usually small detector, traditional optics, like focusing elements, as known by a person skilled in the art may be used. In some embodiments, the focusing element includes a lens. In some embodiments, the focusing element includes a compound parabolic concentrator (CPC).

However, since the response times of commonly used photodiodes as detectors are limited by the junction capacitance and the carrier transit time, and scale with detector size, in one preferred embodiment of the present invention, especially in the case when at least one compound of formula (I) or (I*) is used in the receiver, a combined system of wavelength shifting material and a detector, preferably a photodiode (PD or array of PDs), is employed in the receiver according to the present invention, instead of a detector alone as mentioned in the embodiment described above. The wavelength shifting material may be used instead of traditional optics to collect the modulated electromagnetic radiation or together with traditional optics to collect the modulated electromagnetic radiation. The wavelength shifting materials are optical waveguides (usually polymeric matrix materials) doped with dyes, preferably with at least one compound of formula (I) or (I*). In the combined system of the wavelength shifting materials and detector, preferably photodiode, preferably at least one compound of formula (I) or (I*) is used as dyes.

The incident light, modulated with a communication signal (i.e. the modulated electromagnetic radiation, preferably emitted by the transmitter (T)), is absorbed by the dyes, preferably by at least one compound of formula (I) or (I*), independently of the light incidence angle and subsequently re-emitted at a different wavelength. At least a portion of the emitted light, in an ideal case all of the emitted light, is collected, for example by a fiber or a sheet, and guided to a detector, preferably a photodiode, more preferably a small area photodiode.

An example for a structure of a suitable receiver is for example mentioned in T. G. Tiecke et al., Optica, Vol. 3, No. 7, July 2016, 787-792 and in US 2017/0346556 A. The detector in Tiecke et al. contains a spherical bundle of special fluorescent fibers. The bundle, between the size of a golf ball and tennis ball, is able to absorb (blue laser) light from any direction and re-emit it as green light. The green light is funneled to a small receiver that converts the light back to data. Further examples for suitable receivers are given in US 2017/075191 A1, Collins et al., Optics Letters, Vol. 39, NO. 7, Apr. 1, 2014, 1756-1759, Mulyawan et al., IEEE Photonics Technology Letters, Vol. 29, No. 3, Feb. 1, 2017 and Manousiadis et al., Optica, Vol. 3, No. 7, July 2016, 702-706.

Preferably, the receiver according to the present invention comprises a material (wavelength shifting material) comprising at least one compound of formula (I) or (I*). The compound of formula (I) or (I*) preferably absorbs the modulated electromagnetic radiation emitted by a transmitter (T), i.e. a photon having a wavelength in a first wavelength band, and emits one or more photons having a wavelength in a second wavelength band.

The wavelength shifting material is preferably a solid that includes at least one compound of formula (I) or (I*) as a dye, preferably present in a polymeric matrix. Usually, the dye, especially at least one compound of formula (I) or (I*), is molecularly dissolved in the polymeric matrix.

Suitable polymeric matrix materials are mentioned above. Further suitable polymeric matrix materials are also UV curable or thermally curable resists like epoxy, acrylates or silicones.

The concentration of dye, preferably the compounds of formula (I) or (I*), in the polymeric matrix materials of the wavelength shifting material is set as a function of the thickness of the receiver and the type of polymer. If a thin polymer layer is used, the concentration of the dye, preferably the compounds of formula (I) or (I*), is generally higher than in the case of a thick polymer layer.

Typically, the concentration of the dye, preferably the compounds of formula (I) or (I*), is usually in the range from 0.0001 to 5% by weight, preferably 0.001 to 0.5% by weight, based on the amount of matrix polymer used.

The dye may be applied in the form of particles, which are usually molecularly dissolved in the polymeric matrix. In a further embodiment, the dye is dissolved in a liquid contained in a container (e.g. glass) that includes at least one compound of formula (I) or (I*) (wavelength shifting particles) in dissolved form.

The wavelength shifting material may be present in form of sheets which may be curved and/or flexible, or may be composed of one or more fibers.

The receiver preferably additionally comprises a focusing element focusing and/or otherwise directing the photons having a wavelength in the second wavelength band to a detector. In some embodiments, the focusing element includes a lens. In some embodiments, the focusing element includes a compound parabolic concentrator (CPC). In some embodiments, the focusing element includes another wavelength shifting material configured to absorb photons having wavelengths in the second wavelength band and emit photons in a third wavelength band. In these embodiments, the detector is configured to detect the photons having wavelengths in the third wavelength band. In the last-mentioned embodiments, the wavelength shifting material may be configured to absorb and emit photons having wavelengths in multiple different (non-overlapping) wavelength bands. For example, the wavelength shifting material may include one or more types of dyes. The dyes may include at least one compound of formula (I) or (I*) or different dyes known by a person skilled in the art.

The output of the detector is preferably coupled to a transimpedance amplifier (TIA) (as mentioned above) that converts a current signal produced by the detector into a voltage.

From this point on, the receiver resembles a standard receiver topology as mentioned above.

The surface of one or more of the components of the optical data communication system according to the present invention, especially the surface of one or more of the components of the receiver and/or one or more components of the transmitter may be coated and/or structured. Suitable structures and coatings are known by a person skilled in the art.

One or more components of the receiver may for example coated with an antireflection coating and/or a coating for improving properties like demolding, heat resistance, chemical resistance, corrosion resistance, low friction performance, and weather resistance, for example a coating comprising $SiO_2$ and/or fluoropolymers (fluorocoating).

Especially, the fibers in the optical data communication system, especially in the receiver, are in one preferred embodiment coated by a cladding. A cladding is a layer surrounding the fiber core ("coating") with a thickness of typically 1 to 10 percent of the fiber radius. Its refractive index $n_{clad}$ is lower than $n_{core}$. Typical materials for claddings of fibers, especially plastic fibers, are PMMA or fluorinated polymers (FP) (fluoropolymers). Suitable Fluoropolymers are known by a person skilled in the art. An optical fiber may have one cladding or multiple claddings each with a lower refractive index than the underlying one. The claddings provide interfaces with decreasing refractive indices allowing repeated TIR (total internal reflection) which is used to confine and propagate light inside fiber. Fibers with only one cladding are called singleclad fibers while those with additional claddings are referred to as multiclad fibers.

Input (A) and Output (E)

Input (A) and output (E) are usually information to be transferred, in the form of electrical digital or analog signals. Usually, the information to be transferred is in form of digital information bits.

Optical Path (C)

The optical path (C) may in general be any optical path suitable for optical communication known by a person skilled in the art. Preferably, the optical path (C) is the free space, i.e. an optical wireless channel.

The optical path is in an indoor and/or in an outdoor environment. Preferably, the optical path is in an indoor environment.

Outdoor optical wireless communications can be divided into ultra long-range free space links, medium-/long range links and short-range links. The ultra long-range free space links are for example used for networking a constellation of satellites. The medium-/long range links are for example used for inter-building networks or mobile backhaul. The short-range links are used for example car-to-car communications.

Indoor optical wireless communication can be divided into short-range links and ultra-short range links. Short range links are for example optical WLAN, in-flight communications, car-to-infrastructure communications, indoor positioning and wireless automation. Indoor optical wireless communication is applied for example in homes, offices and warehouses ranging from TV control to IrDA (Infrared Data Association) ports on portable electronic devices such as mobile phones, digital cameras, personal digital assistants and laptops. Ultra short range links are for example interchip interconnections and in-body networks.

More preferably, the optical path is the free space in an indoor environment.

Further Optional Components

In addition, the optical data communication system according to the present invention may further comprise an optical system in order to further shape the modulated electromagnetic radiation emitted by the transmitter (T). For example, an optical amplifier lens, a collimator, and/or a diffusor can be employed to concentrate or broaden the modulated electromagnetic radiation.

EXAMPLES

The following FIGURES and examples serve to illustrate the invention and should not be interpreted as limiting.

Comparative Example 1C 4,4'-Bis[(N-carbazole)styryl]biphenyl (BSB-Cz)
(Zhang et al. Optical Materials 32 (2009)94-98)

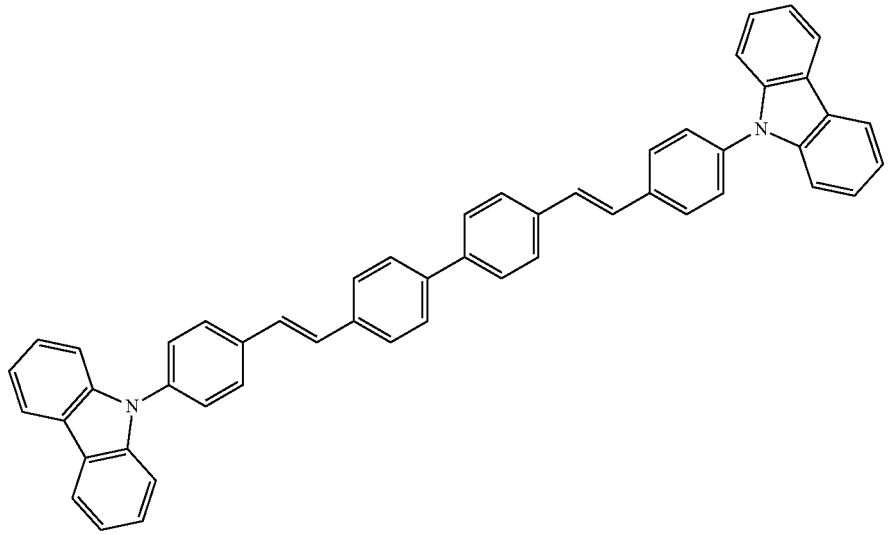 [SMILES: C(=C\c1ccc(-n2c3ccccc3c3ccccc32)cc1)/c1ccc(-c2ccc(/C=C/c3ccc(-n4c5ccccc5c5ccccc54)cc3)cc2)cc1]

Example 1.1

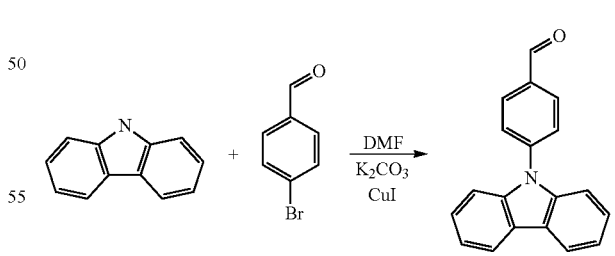

A mixture of 9.53 g (57 mmol) carbazole, 21.31 g (114 mmol) 4-bromobenzaldehyde, 11.89 g $K_2CO_3$ (86 mmol), 1.80 g (9.4 mmol) CuI in 60 ml of DMF was reacted for 19 hours at 140° C.

The reaction mixture was cooled to room temperature, filtered, washed with DMF and the filtrate diluted with ice. The residue was filtered and washed with water and ethanol. 11.36 g (74%) of a beige solid were obtained.

Example 1.2

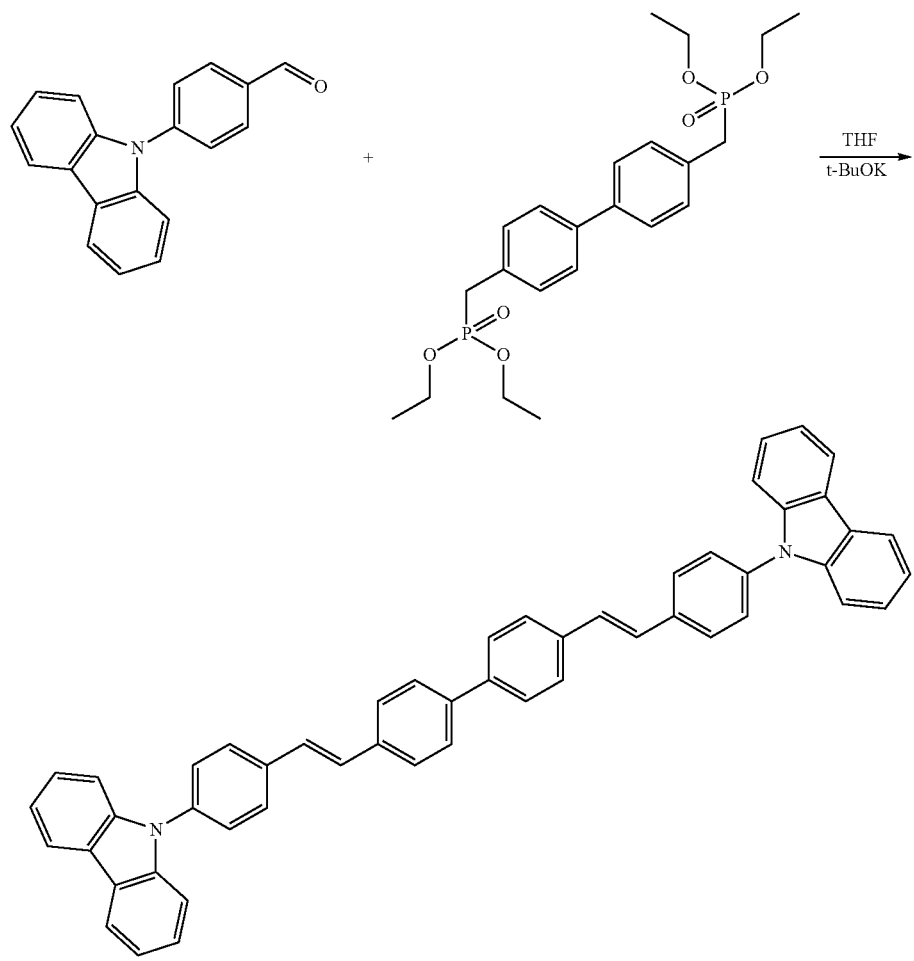

A mixture of 0.9 g (3.3 mmol) of the above-mentioned compound of example 1.1 was reacted with 0.65 g (1.4 mmol) 4,4-bis(diethylphosphonomethyl)-biphenyl (example 1.3), 0.41 g KOtBu (3.5 mmol) and 40 ml of THF at room temperature for four hours.

The reaction mixture was diluted with ethanol, filtered and the residue washed with ethanol and pentane and dried under reduced pressure. 0.95 g of a yellowish residue were recrystallized from 1,2-dichlorobenzene. 0.77 g (79%) of a light yellow solid were obtained.

Example 1.3: Michaelis Arbuzov Reaction

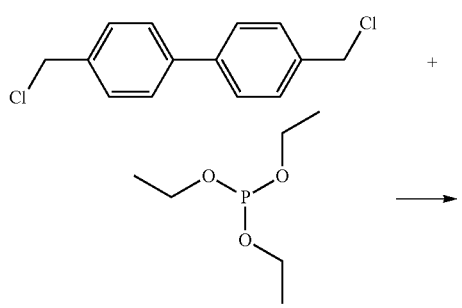

-continued

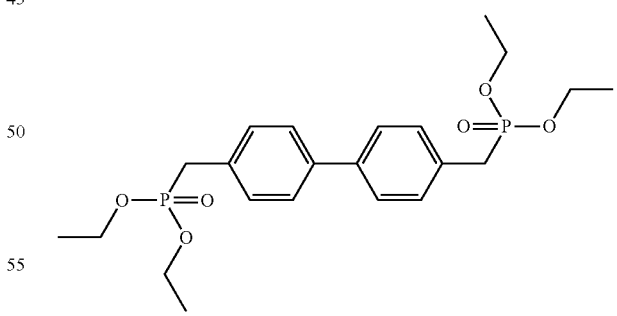

5.8 g (199.71 mmol) 4,4'-Bis-chloromethyldiphenyle were reacted with 105 g (600.00 mmol) triethylphosphite at 159° C. for 4 hours. The excess amount of triethylphosphite was distilled off. The residue was diluted with toluene. The precipitated product was filtered, washed with toluene and dried under reduce pressure. 53.2 g (59%) of a white solid was obtained.

Melting point: 111° C.

Example 2

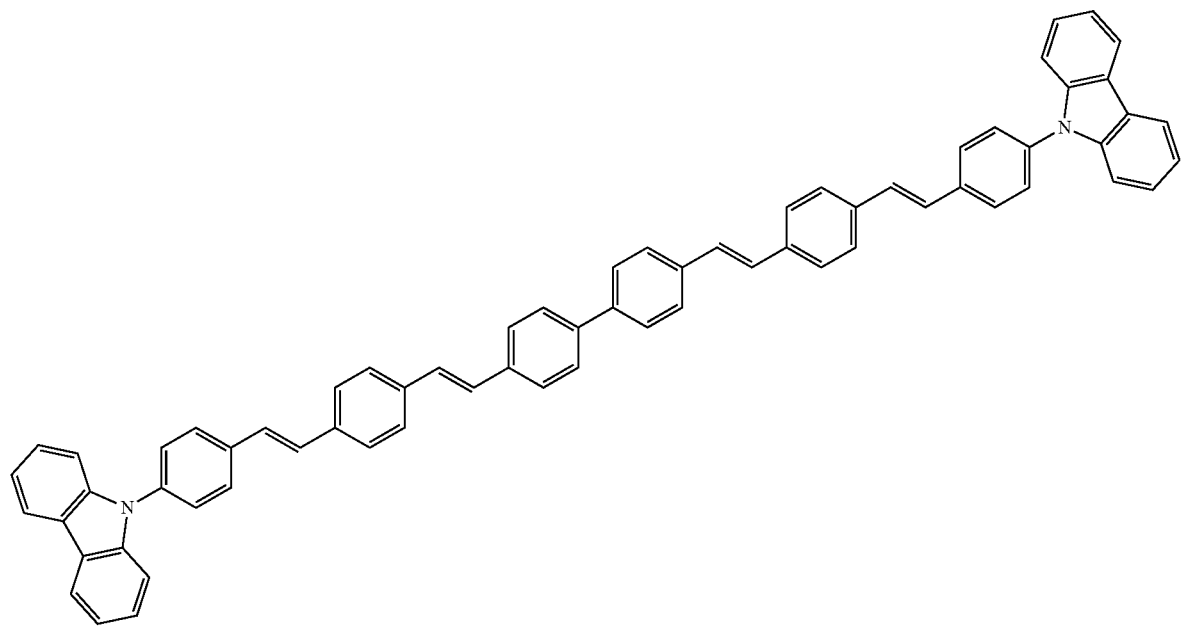 [SMILES: C(=C\c1ccc(-c2ccc(/C=C/c3ccc(/C=C/c4ccc(-n5c6ccccc6c6ccccc65)cc4)cc3)cc2)cc1)/c1ccc(/C=C/c2ccc(-n3c4ccccc4c4ccccc43)cc2)cc1]

Example 2.1

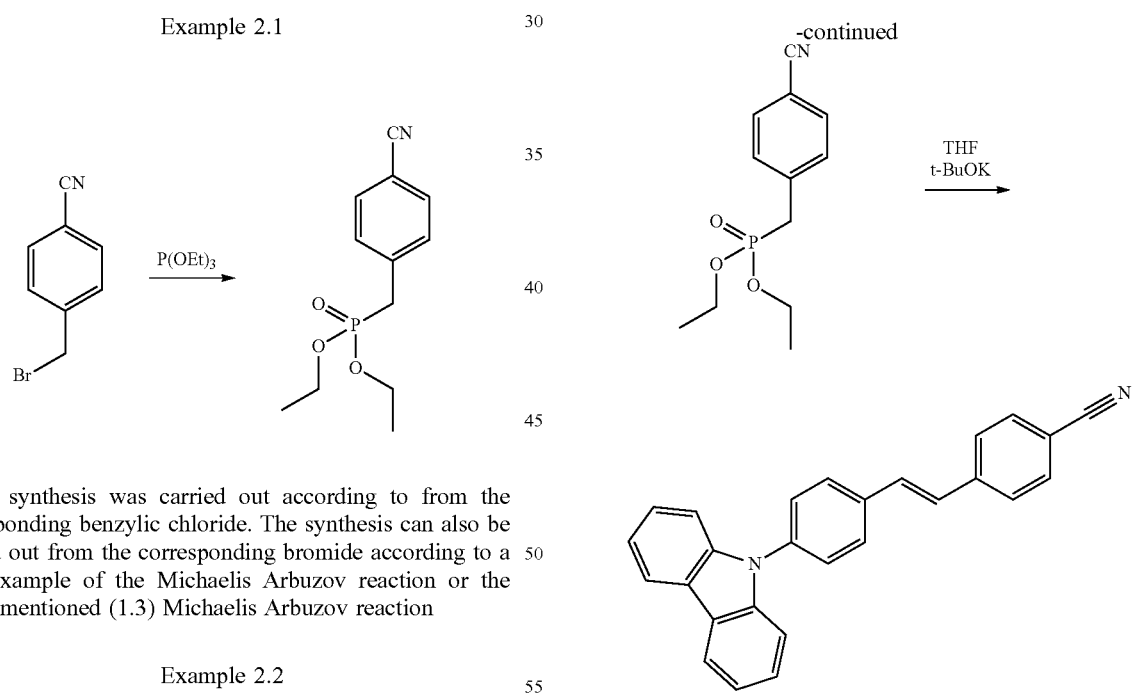

The synthesis was carried out according to from the corresponding benzylic chloride. The synthesis can also be carried out from the corresponding bromide according to a later example of the Michaelis Arbuzov reaction or the above mentioned (1.3) Michaelis Arbuzov reaction

Example 2.2

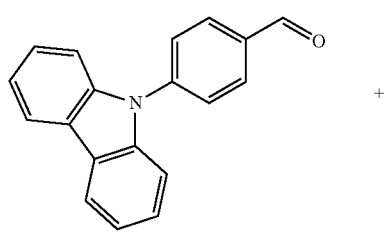 +

A mixture of 3.00 g (11.06 mmol) 4-(9H-carbazole-9-yl) benzaldehyde (example 1.1) was reacted with 2.69 g (10.53 mmol) (4-cyanobenzyl)-phosphonic acid-diethylester, 1.33 g (11.6 mmol) KOtBu and 100 mL of THF at room temperature for 4 hours.

The solvent was removed from the reaction mixture. The residue was worked up with water and ethyl acetate. The insoluble residue in the aqueous layer was filtered, washed with water und dried under reduced pressure. 1.41 g (36%) of a yellow solid were obtained.

The solvent from the organic phase from the extraction was removed. The residue was mixed with MTBE (Methyl-tert-butylether), filtered and washed with MTBE and n-pentane. The residue was dried under reduced pressure. 1.12 g (29%) of a yellow solid were obtained.

Example 2.3

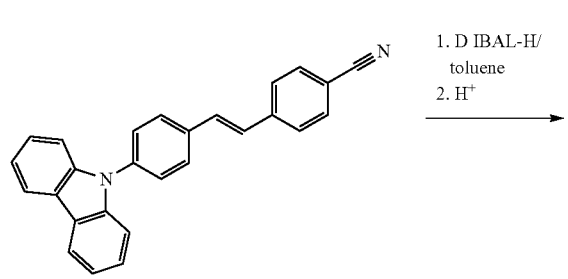

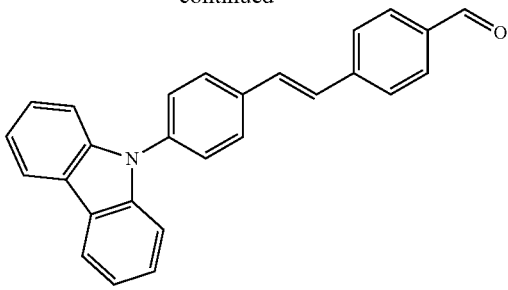

A mixture of 1.08 g (2.9 mmol) of the corresponding nitrile of example 2.2 was dissolved in 15 ml toluene and cooled to 0° C. A solution of 0.54 g of a 1M diisobutylaluminiumhydride in toluene (3.8 ml, 3.8 mmol) was added within 10 minutes. The mixture was stirred at this temperature for 1 hour. 4.5 ml of 3M hydrochloric acid was added and 2.0 ml of 1M hydrochloric acid was added. The reaction mixture was warmed to room temperature. The precipitated product was isolated by filtration, washed with ethyl acetate and dried. 0.65 g (60%) of an orange compound were isolated.

TLC (cyclohexane:ethyl acetate 3:1): $R_f$=0.53

Example 2.4

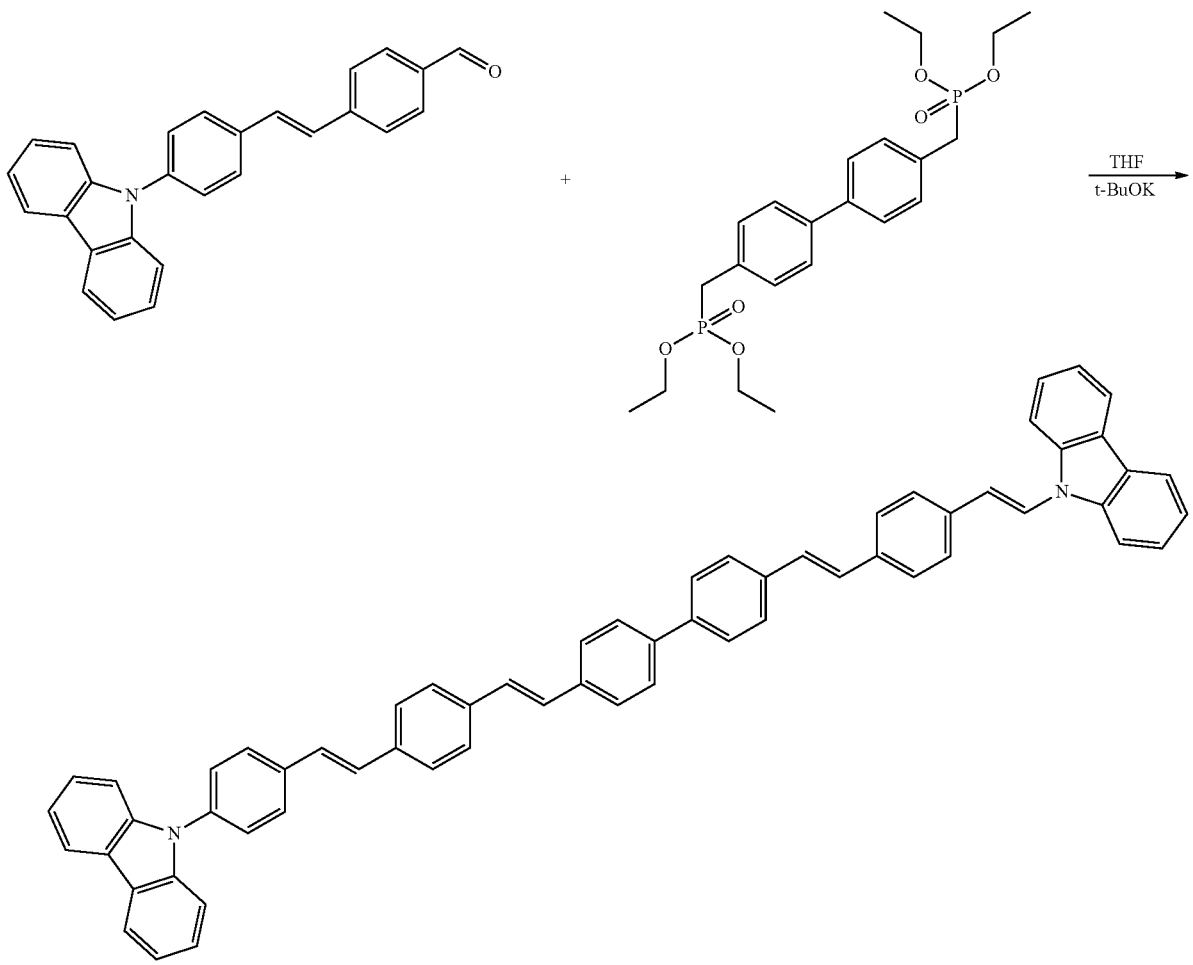

The Wittig Horner Wadsworth Emmons reaction of the compounds mentioned in example 2.3 and 4,4-bis(diethylphosphonomethyl)-biphenyl (example 1.3) was carried out according to example 1.2 without recrystallization.

0.77 g (71%) of a yellow solid were obtained.

TLC (cyclohexane:ethyl acetate 3:1): $R_f$=0

Example 3

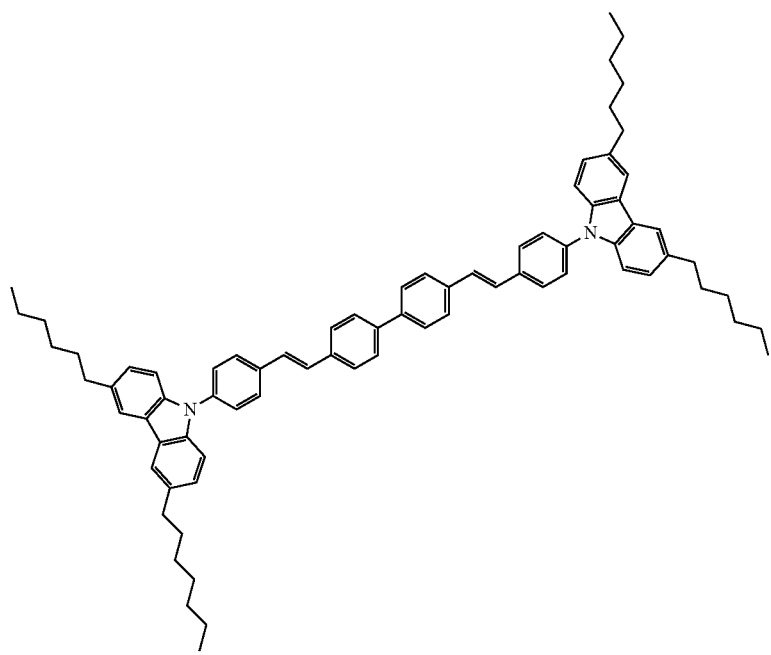 [SMILES: CCCCCCCc1ccc2c(c1)c1cc(CCCCCC)ccc1n2-c1ccc(/C=C/c2ccc(-c3ccc(/C=C/c4ccc(-n5c6ccc(CCCCCC)cc6c6cc(CCCCCC)ccc65)cc4)cc3)cc2)cc1]

The synthesis was carried out according to example 1 using the corresponding dihexylcarbazole as starting material. The corresponding 4,7-dihexylcarbazole was made according to X.Y. Wang Chemistry A European Journal 2015, 21, 24, 8867-8873.

Example 3.1

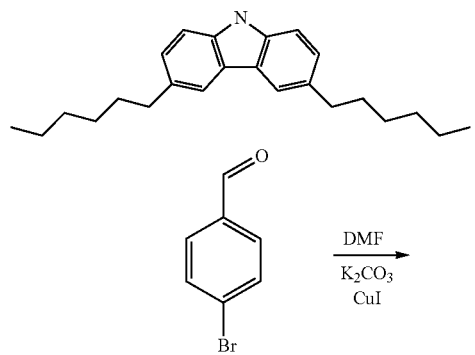

-continued

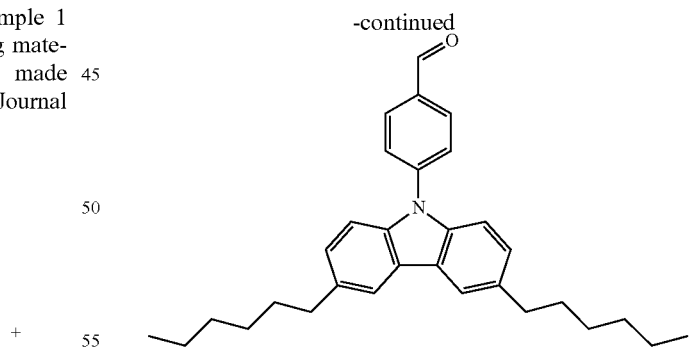

The reaction of 3,6-dihexyl-9H-carbazole and 4-bromobenzaldehyde was carried out analogous to example 1.1. The reaction time was 23 hours at 140° C. and 22 hours at 150° C.

The reaction mixture was cooled to room temperature and extracted with MTBE and water. The organic layer was dried with $MgSO_4$ and the solvent was removed. The residue was purified by liquid chromatography with cyclohexane/dichloromethane. 6.41 g (49%) of a yellow crystalline solid were obtained.

TLC (cyclohexane:acetone 10:1): $R_f$=0.62

Example 3.2

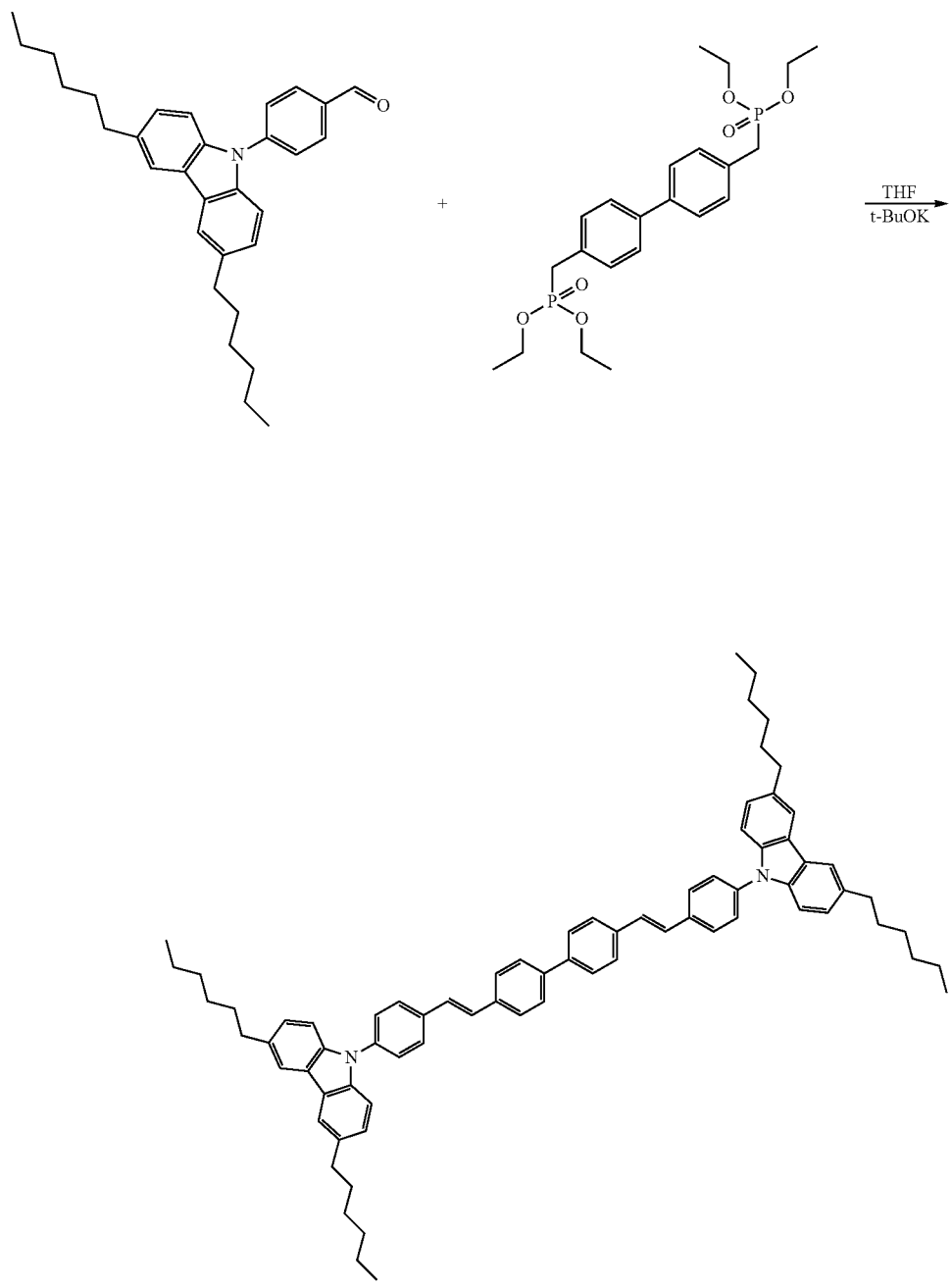

The Wittig Horner Wadsworth Emmons reaction of the compounds mentioned in example 3.1 and 4,4-bis(diethylphosphonomethyl)-biphenyl (example 1.3) was carried out according to example 1.2.

The solvent of the reaction mixture was removed. The residue was extracted with water and dichloromethane. The organic layer was dried with $MgSO_4$ and the solvent was removed. The residue was dissolved in n-pentane. Acetone was added. The precipitated product was filtered off, washed with acetone and dried under reduced pressure. 0.86 g (86%) of a yellow solid were obtained.

TLC (cyclohexane:acetone 10:1): $R_f$=1

Example 4
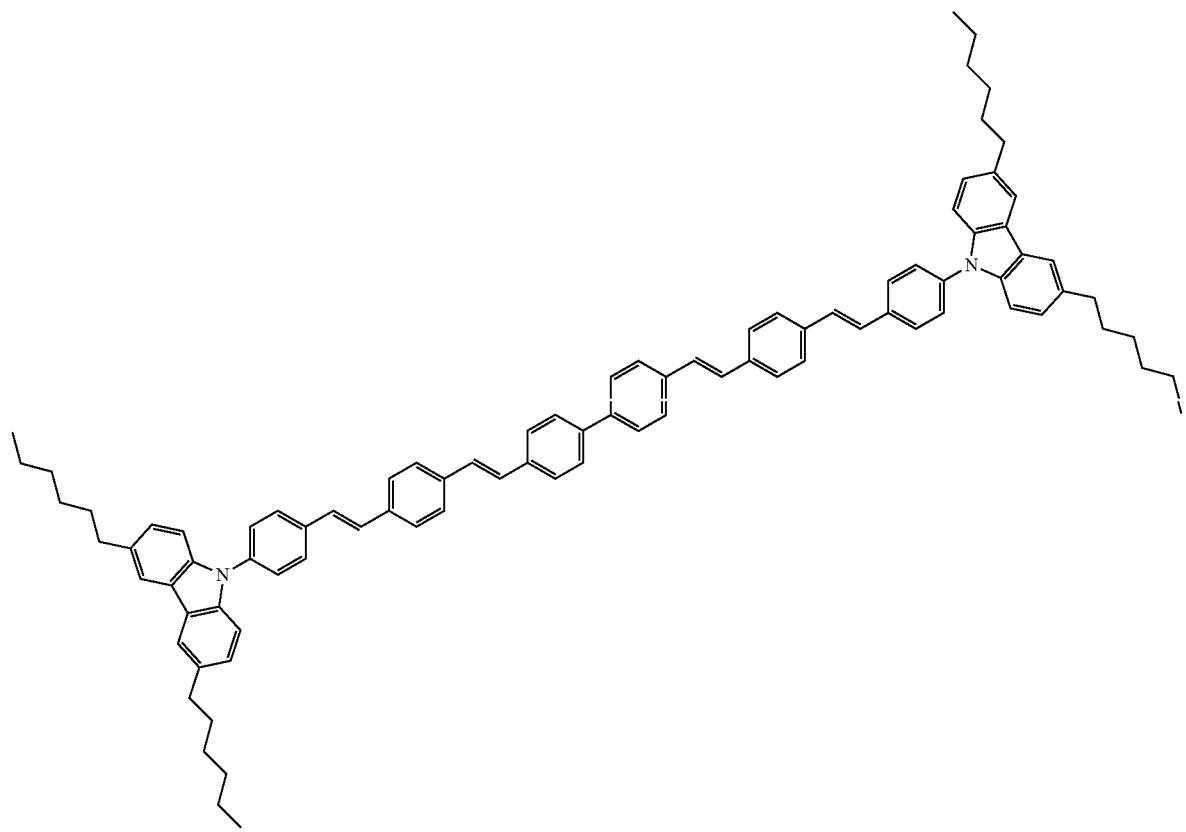 [SMILES: CCCCCCc1ccc2c(c1)c1cc(CCCCCC)ccc1n2-c1ccc(/C=C/c2ccc(/C=C/c3ccc(-c4ccc(/C=C/c5ccc(/C=C/c6ccc(-n7c8ccc(CCCCCC)cc8c8cc(CCCCCC)ccc87)cc6)cc5)cc4)cc3)cc2)cc1]
The synthesis was carried out according to example 2 using the corresponding dihexylcarbazole as starting material.
Example 4.1
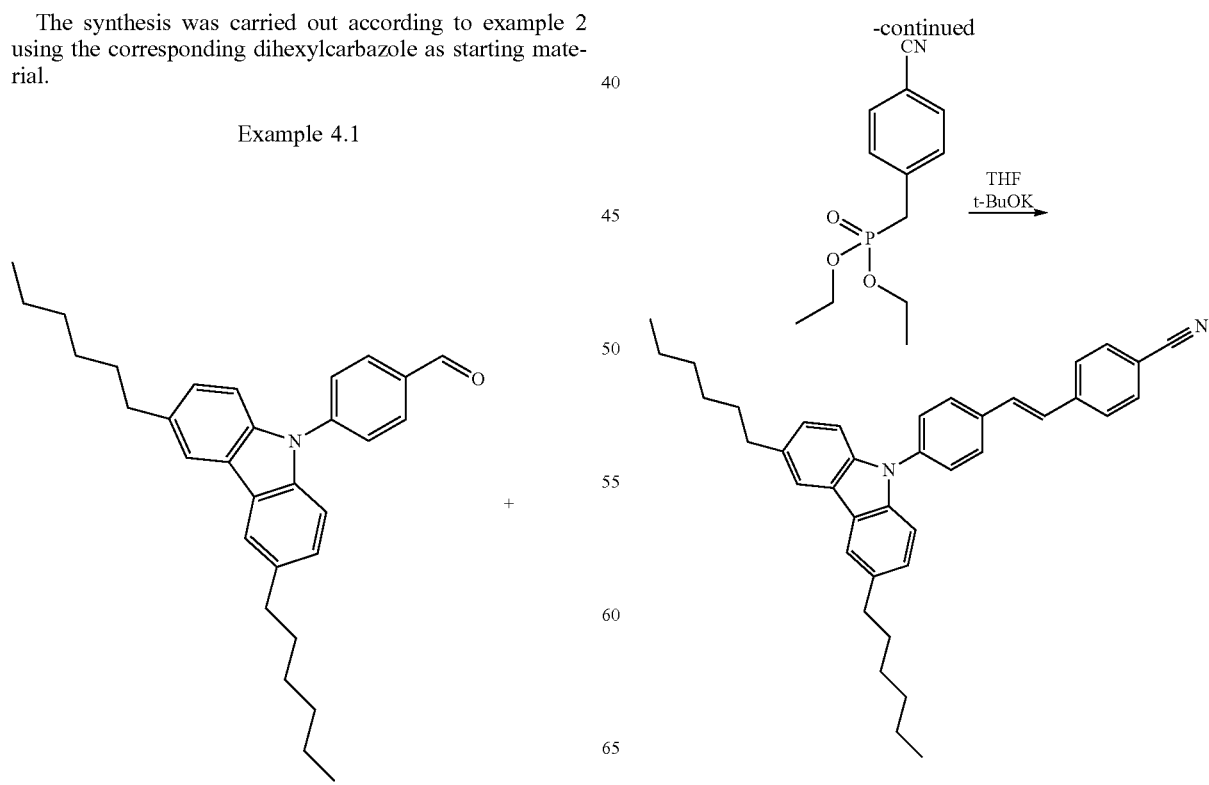

The Wittig Horner Wadsworth Emmons reaction of 4-(3,6-dihexylcarbazol)-9-yl)benzaldehyde (example 3.1) and 4,4-bis(diethylphosphonomethyl)-biphenyl (example 2.1) was carried out analogous to example 2.2.

The reaction mixture was worked up with water and dichloromethane. The organic layer was dried and the solvent removed. The residue was purified by liquid chromatography with cyclo-hexane/dichlormethane. 3.75 g (91.8) of a green-yellow crystalline solid were obtained.

TLC (cyclohexane:acetone 10:1): $R_f$=0.49

Example 4.2

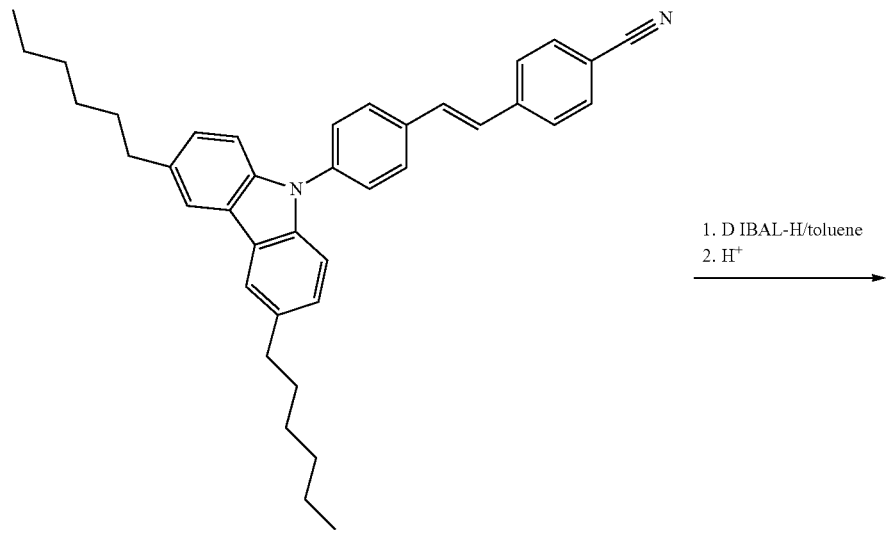

1. DIBAL-H/toluene
2. $H^+$

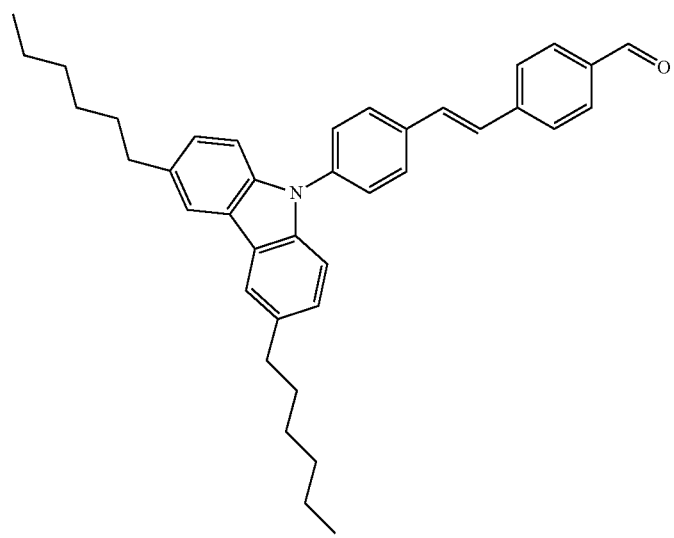

The reaction of the above-mentioned nitrile (example 4.1) was carried out analogous to example 2.3.

The reaction mixture was worked up with water and MTBE. The organic layer was dried and the solvent was removed. 1.85 g (87%) of an orange-yellow crystalline solid were obtained.

TLC (dichlormethane: cyclohexane 3:1): $R_f$=0.6

Example 4.3

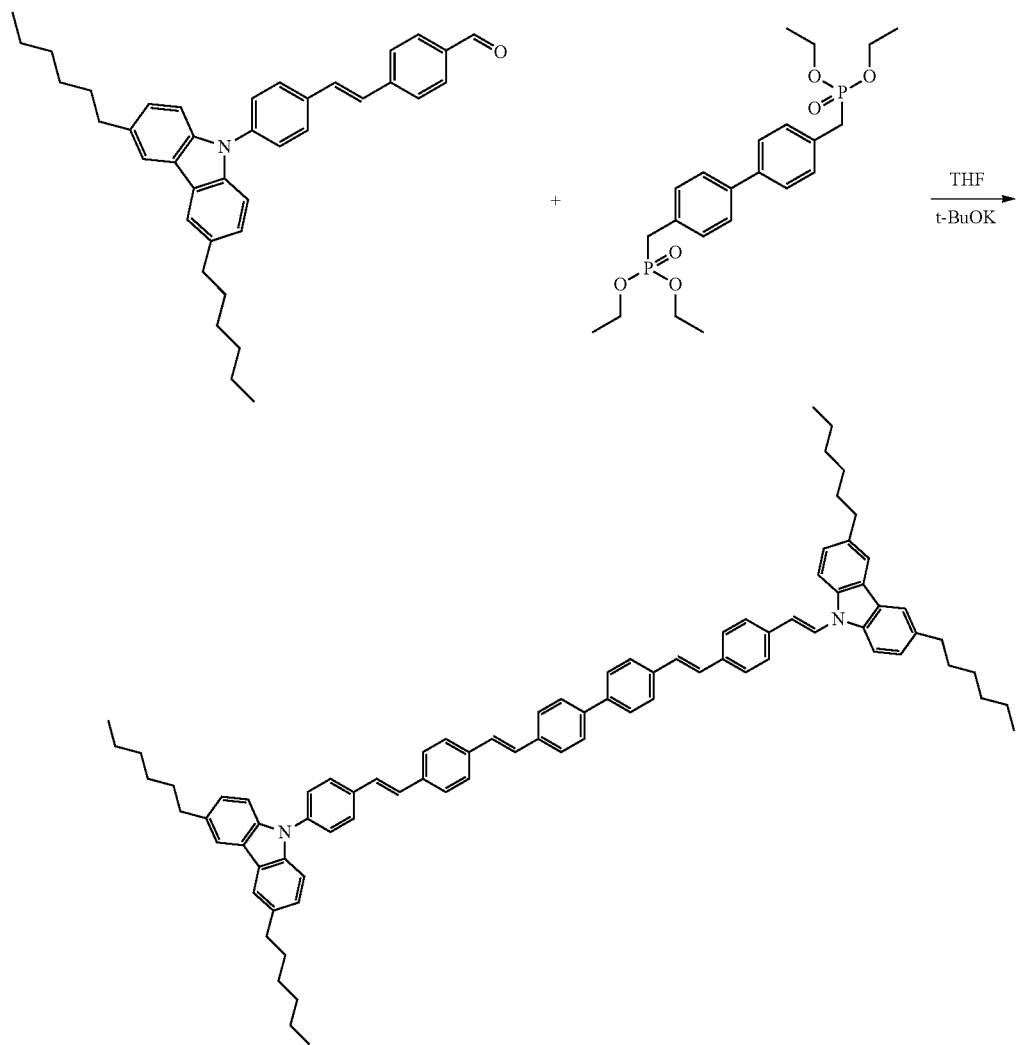

The Wittig Horner Wadsworth Emmons reaction of above-mentioned compound (example 4.2) with 4,4-bis(di-ethylphosphonomethyl)-biphenyl (example 1.3) was carried out according to example 1.2

The reaction mixture was diluted with ethanol. The solid was filtered off, washed with ethanol and dried. 0.92 g (86%) of a yellow solid were obtained.

TLC (cyclohexane:dichloromethane 1:3): $R_f$=0

Example 5

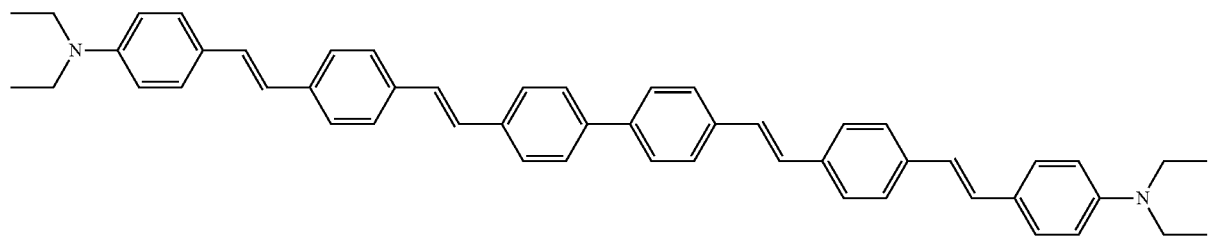 [SMILES: CCN(CC)c1ccc(/C=C/c2ccc(/C=C/c3ccc(-c4ccc(/C=C/c5ccc(/C=C/c6ccc(N(CC)CC)cc6)cc5)cc4)cc3)cc2)cc1]

Example 5.1

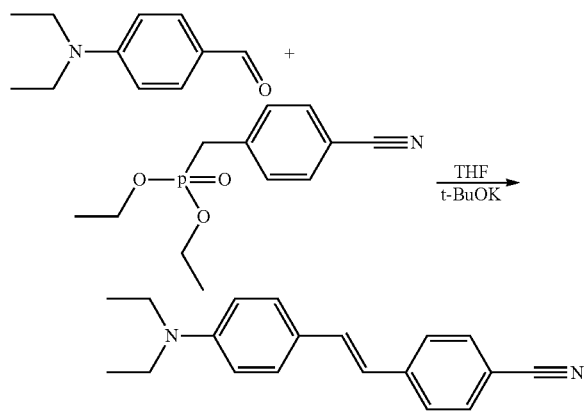

The Wittig Horner Wadsworth Emmons reaction of 4-diethylamino-benzaldehyde and 4,4-Bis(diethylphosphonomethyl)-biphenyl (example 2.1) was carried out analogous to example 2.2. The solvent from the reaction mixture was removed. The residue was worked up with a hydrochloric acid solution and dichloromethane. The organic layer was dried and the solvent was removed. 5.66 g (100%) of a golden yellow solid were obtained.

Example 5.2

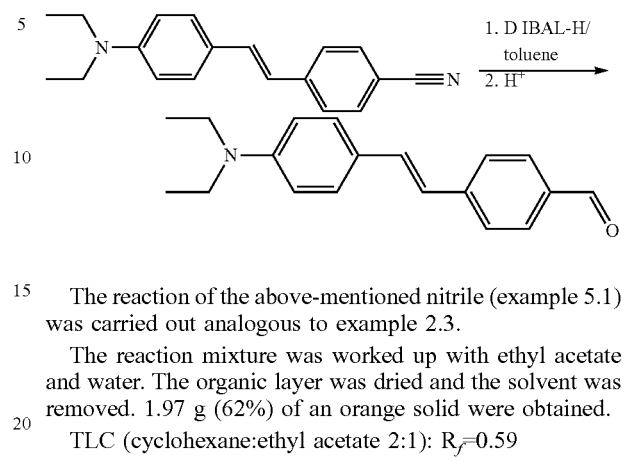

The reaction of the above-mentioned nitrile (example 5.1) was carried out analogous to example 2.3.

The reaction mixture was worked up with ethyl acetate and water. The organic layer was dried and the solvent was removed. 1.97 g (62%) of an orange solid were obtained.

TLC (cyclohexane:ethyl acetate 2:1): $R_f$=0.59

Example 5.3

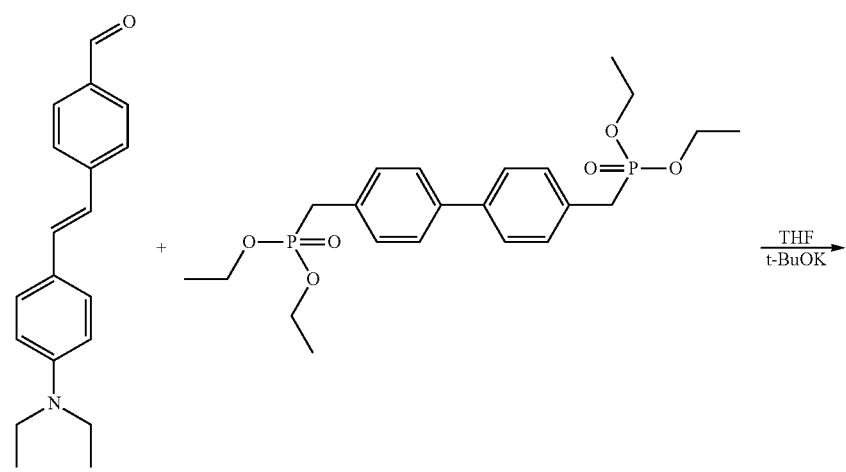

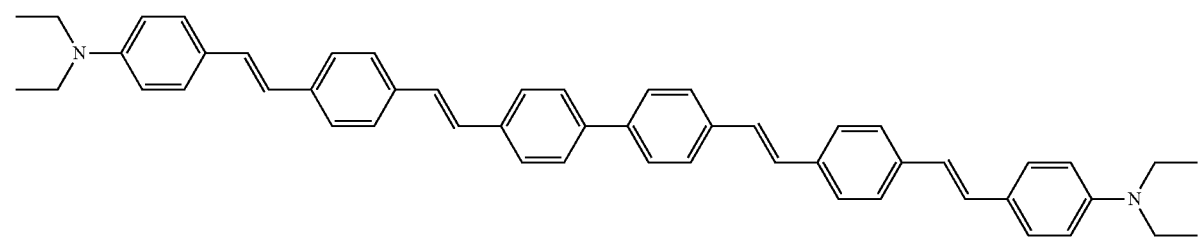

The Wittig Horner Wadsworth Emmons reaction of above-mentioned compound (example 5.2) with 4,4-bis(diethylphosphonomethyl)-biphenyl (example 1.3) was carried out according to example 1.2.

The reaction mixture was diluted with ethanol. The solid was filtered off and washed with ethanol and n-pentane. The residue was recrystallized with NMP and the residue was washed with methanol and n-pentane and dried. 0.37 g (51%) of a yellow solid were obtained.

TLC (cyclohexane:dichloromethane 1:3): $R_f$=0

Example 6

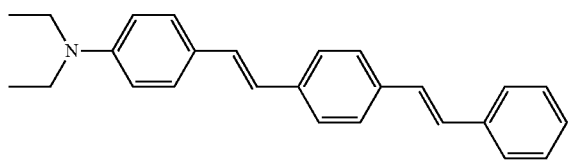

Example 6.1

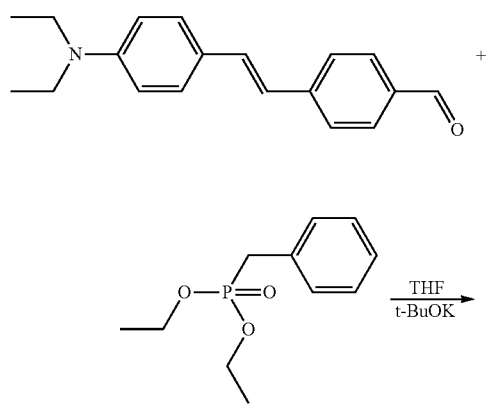

The reaction of 4-[(E)-2[4-(diethylamino)phenyl]vinyl]-benzaldehyde and diethylbenzylphosphonate was carried out analogous to example 2.2.

The solvent from the reaction mixture was removed. The residue was worked up with hydrochloric acid solution and dichloromethane. The organic layer was dried and the solvent was removed. The residue was purified by liquid chromatography with cyclohexane/dichloromethane. 0.13 g (15%) of a yellow solid were obtained.

TLC (cyclohexane:dichloromethane 1:3): $R_f$=0.66

Example 7

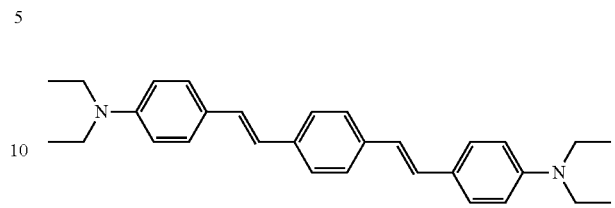

Example 7.1

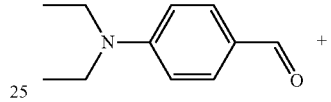

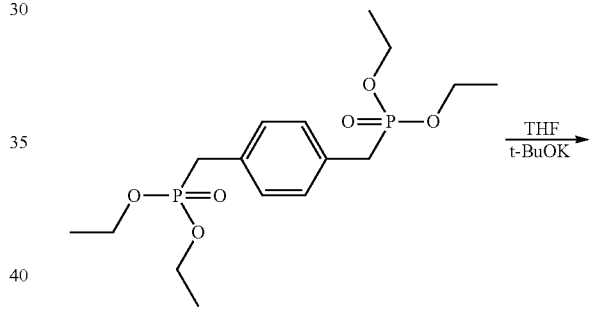

The reaction of 4-diethylamino-benzaldehyde and tetraethyl p-xylylenediphosphonate was carried out analogous to example 1.2.

The solvent was removed from the reaction mixture. The residue was worked up with water and dichloromethane. The organic layer was dried and the solvent was removed. The residue was purified by liquid chromatography with cyclohexane/dichloromethane. The residue was worked up with n-pentane and 1.32 g (81%) of a yellow solid were obtained.

TLC (cyclohexane:dichloromethane 1:3): $R_f$=0.5

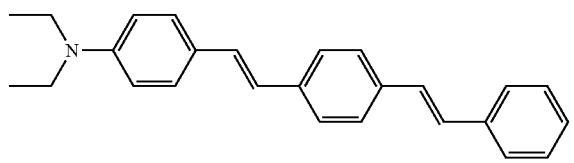 [SMILES: CCN(CC)c1ccc(/C=C/c2ccc(/C=C/c3ccccc3)cc2)cc1]

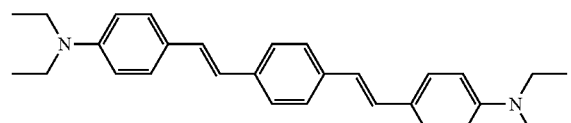

Example 8
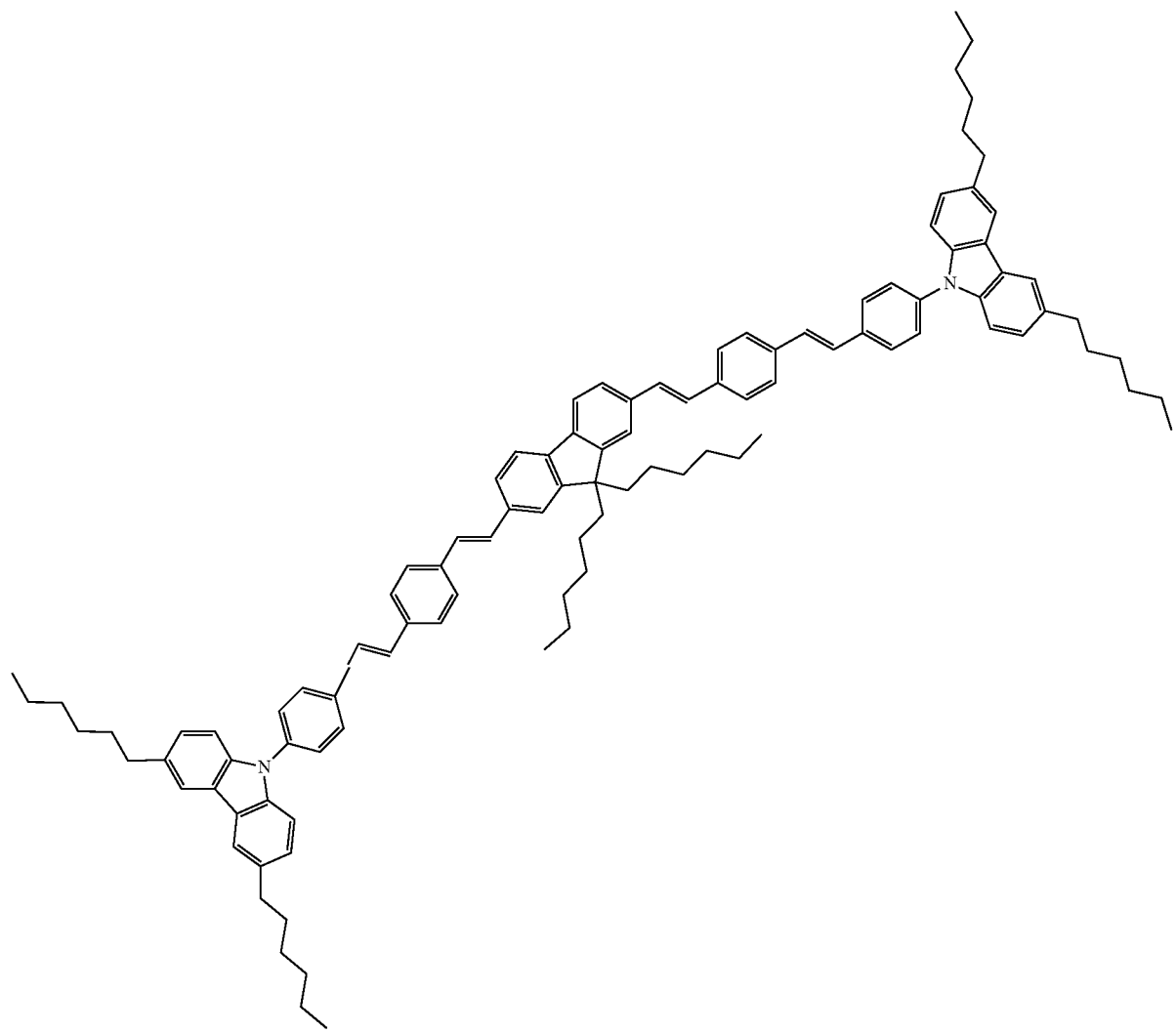 [SMILES: CCCCCCCC1(CCCCCC)c2cc(/C=C/c3ccc(/C=C/c4ccc(-n5c6ccc(CCCCCC)cc6c6cc(CCCCCC)ccc65)cc4)cc3)ccc2-c2ccc(/C=C/c3ccc(/C=C/c4ccc(-n5c6ccc(CCCCCC)cc6c6cc(CCCCCC)ccc65)cc4)cc3)cc21]
Example 8.1
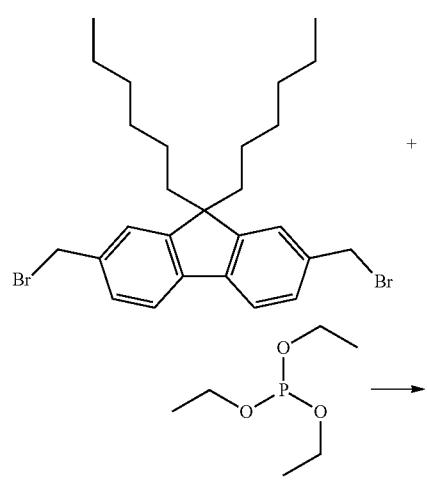
The reaction of 2,7-bis(bromomethyl)-9,9-dihexyl-9H-fluorene and triethylphosphite was carried out analogous to example 1.3.

The excess amount of triethylphosphite was distilled off. The residue was purified by liquid chromatography with ethyl acetate/methanol. 0.93 g (79%) of a colorless oil were obtained.
TLC (ethyl acetate:methanol 20:1): $R_f$=0.38
Example 8.2
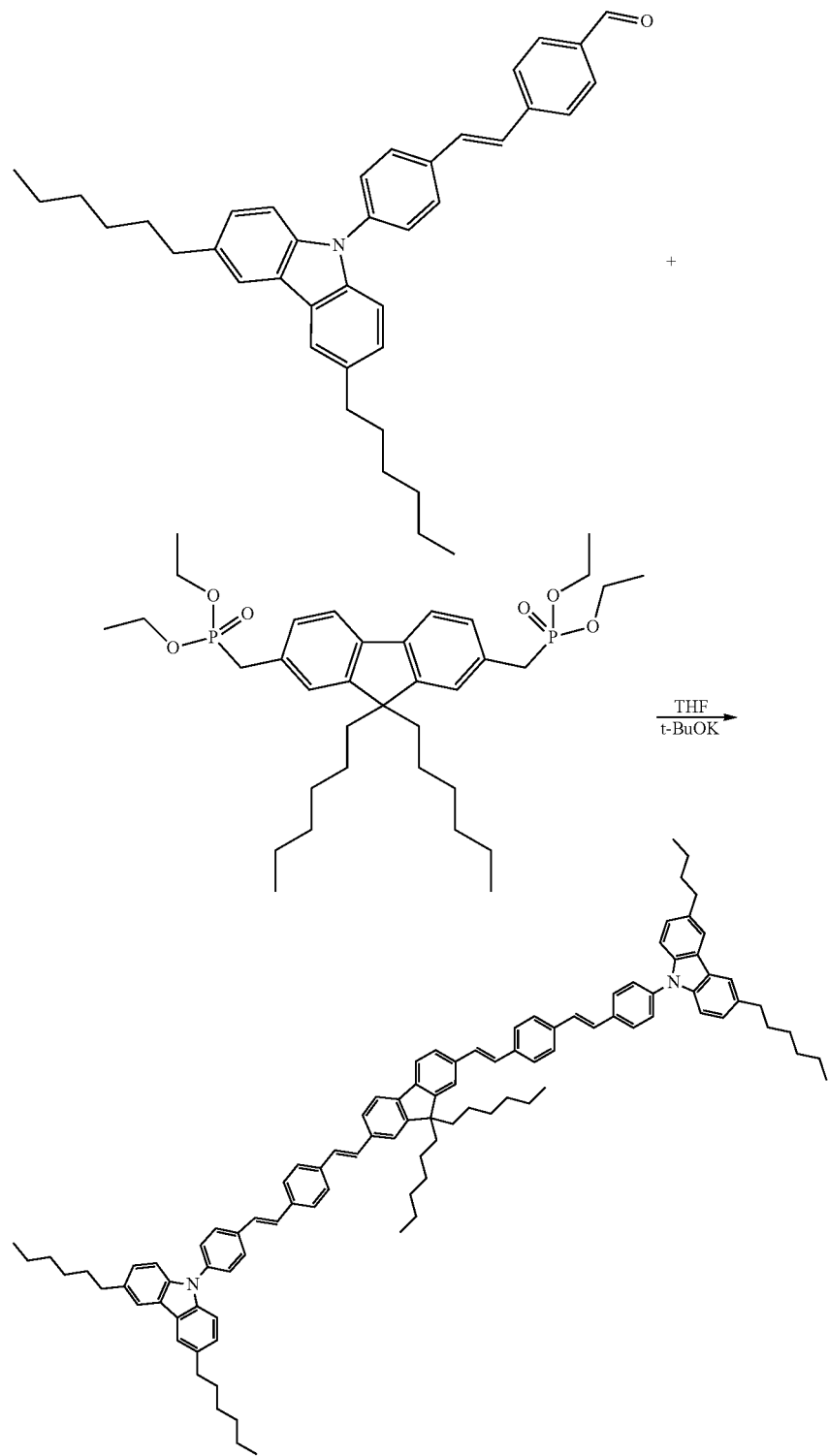

The Wittig Horner Wadsworth Emmons reaction of above-mentioned compound (example 8.1) with 4-[(E)-2-[4-(3,6-dihexylcarbazol-9-yl)phenyl]vinyl]benzaldehyde (example 4.1) was carried out according to example 1.2.

The solvent was removed from the reaction mixture. The residue was worked up with water and dichloromethane. The organic layer was dried and the solvent was removed. The obtained solid was purified by liquid chromatography with cyclohexane and dichloromethane. 0.29 g (22%) of a green-yellow solid were obtained.

TLC (cyclohexane:dichloromethane 1:3): $R_f$=1

Example 9

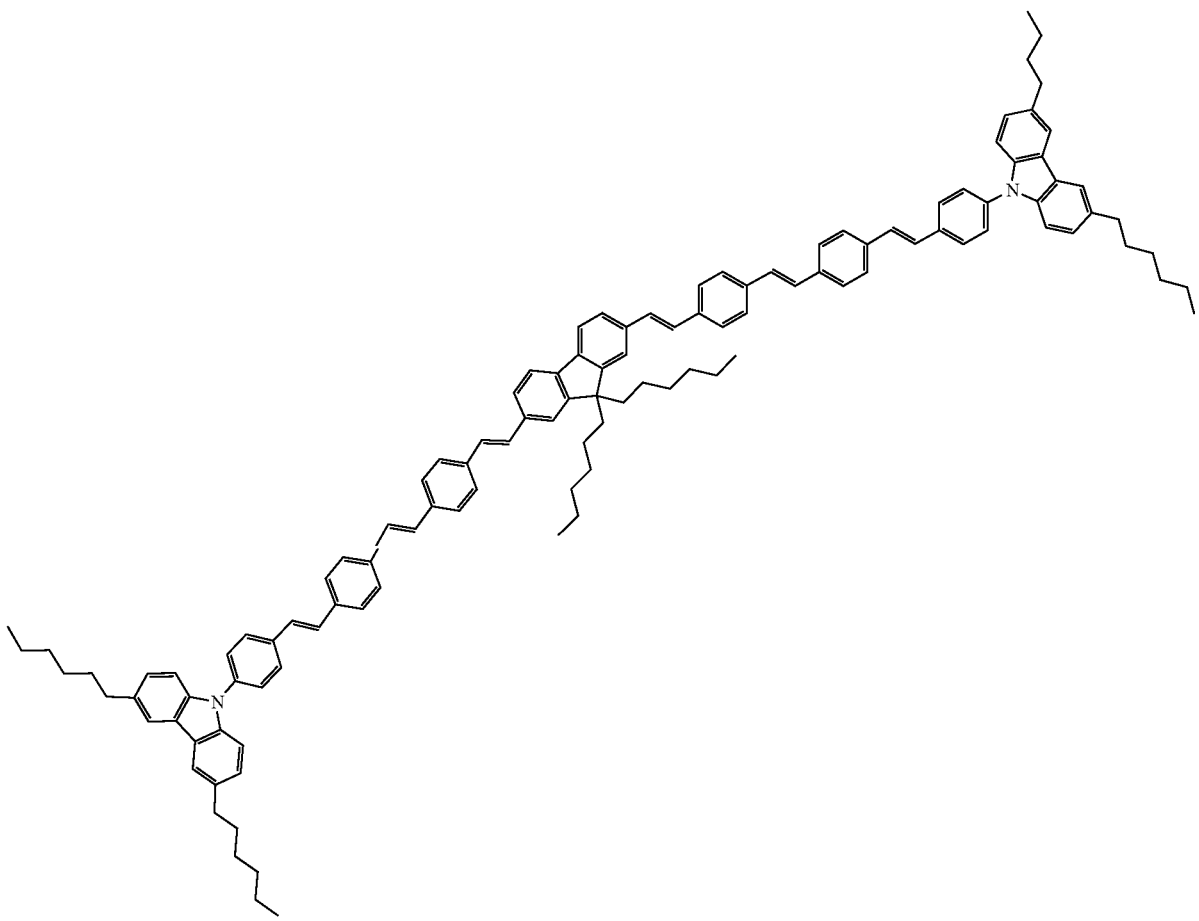 [SMILES: CCCCCCc1ccc2c(c1)c1cc(CCCC)ccc1n2-c1ccc(/C=C/c2ccc(/C=C/c3ccc(/C=C/c4ccc5c(c4)C(CCCCCC)(CCCCCC)c4cc(/C=C/c6ccc(/C=C/c7ccc(/C=C/c8ccc(-n9c%10ccc(CCCCCC)cc%10c%10cc(CCCCCC)ccc%109)cc8)cc7)cc6)ccc4-5)cc3)cc2)cc1]

Example 9.1

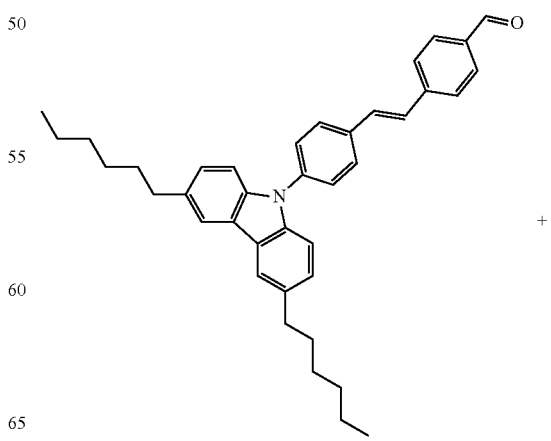

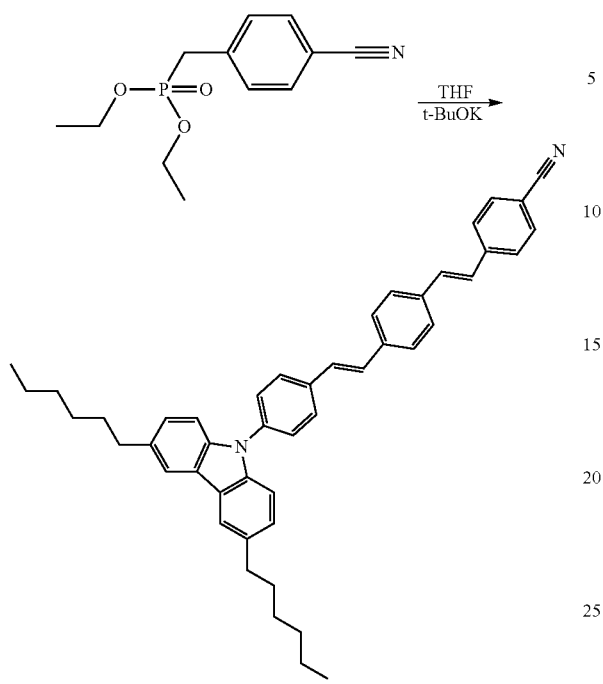

The Wittig Horner Wadsworth Emmons reaction of 4-[(E)-2-[4-(3,6-dihexylcarbazol-9-yl)phenyl]vinyl]benzaldehyde (example 4.1) and 4,4-bis(diethylphosphonomethyl)-biphenyl (example 2.1) was carried out according to example 2.2.

The reaction mixture was worked up with water and dichloromethane. The organic layer was dried and the solvent was removed. The residue was purified by liquid chromatography with cyclohexane/dichloromethane. 0.12 g (18.2%) of a yellow solid were obtained.

TLC (cyclohexane:dichloromethane 1:3) $R_f$=0.76

Example 9.2

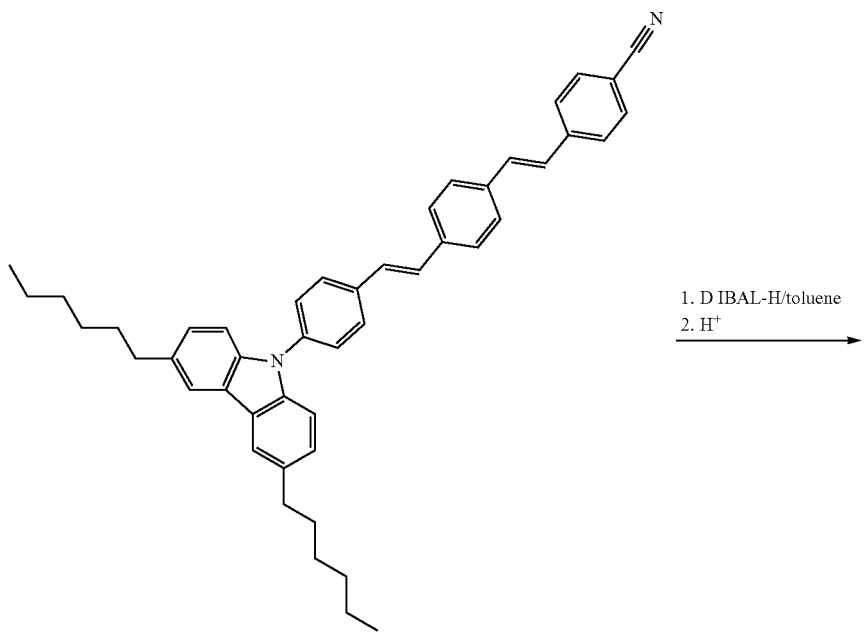

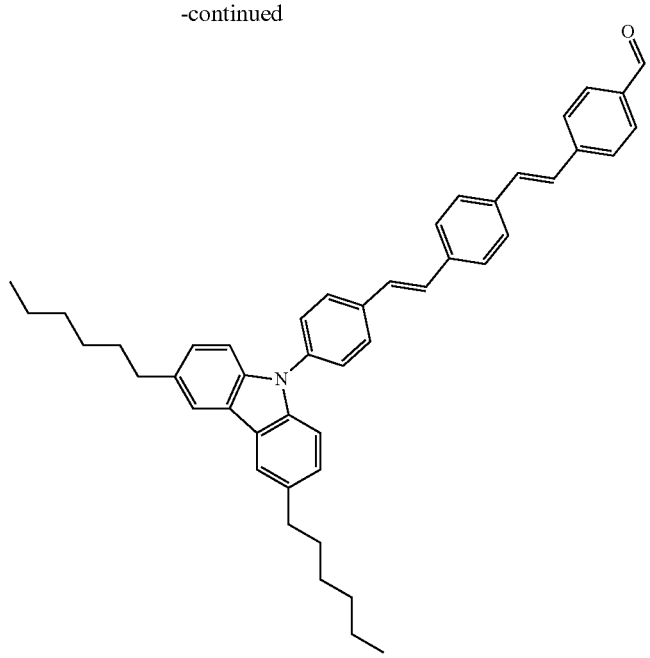
The reaction of the above-mentioned nitrile (example 9.1) was carried out analogous to example 2.3.
The reaction mixture was worked up with water and MTBE. The organic layer was dried and the solvent was removed. 96 mg (98%) of an orange yellow solid was obtained.
TLC/cyclohexane:dichloromethane 1:3): $R_f$=0.68
Example 9.4
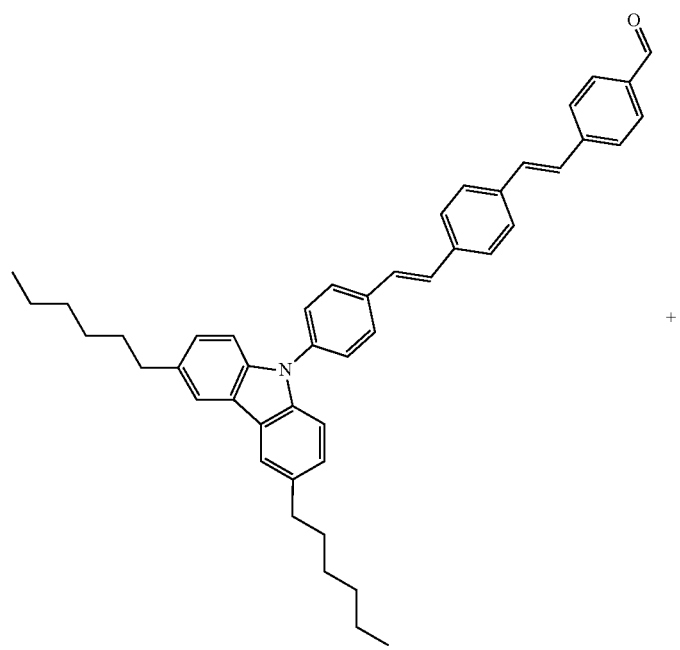
+

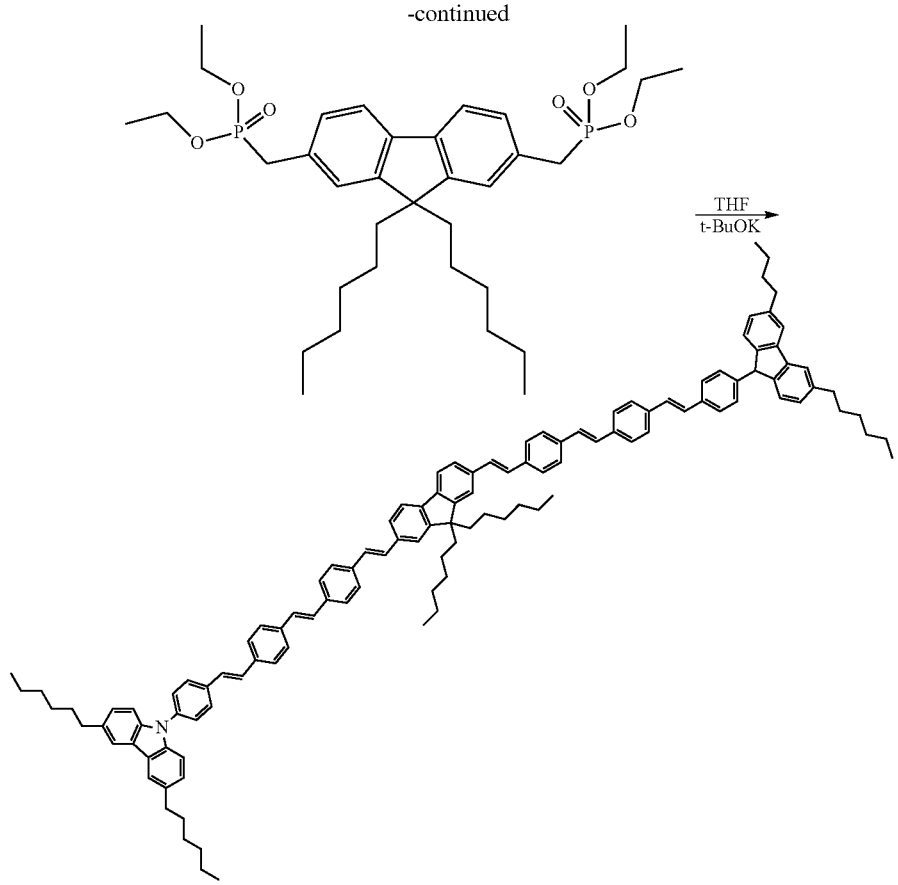

The Wittig Horner Wadsworth Emmons reaction of above-mentioned compounds (example 9.2) with 2,7-bis(diethoxyphosphorylmethyl)9,9-dihexyl-fluorene (example 8.1) was carried out according to example 1.2.

The reaction mixture was worked up with water and dichloromethane. The organic layer was dried and the solvent removed. The residue was purified by liquid chromatography with cyclo-hexane/dichloromethane. The obtained solid was worked up with n-pentane. 112 mg (47%) of a yellow solid were obtained.

TLC (cyclohexane:dichloromethane 1:3): $R_f$=1

Example 10

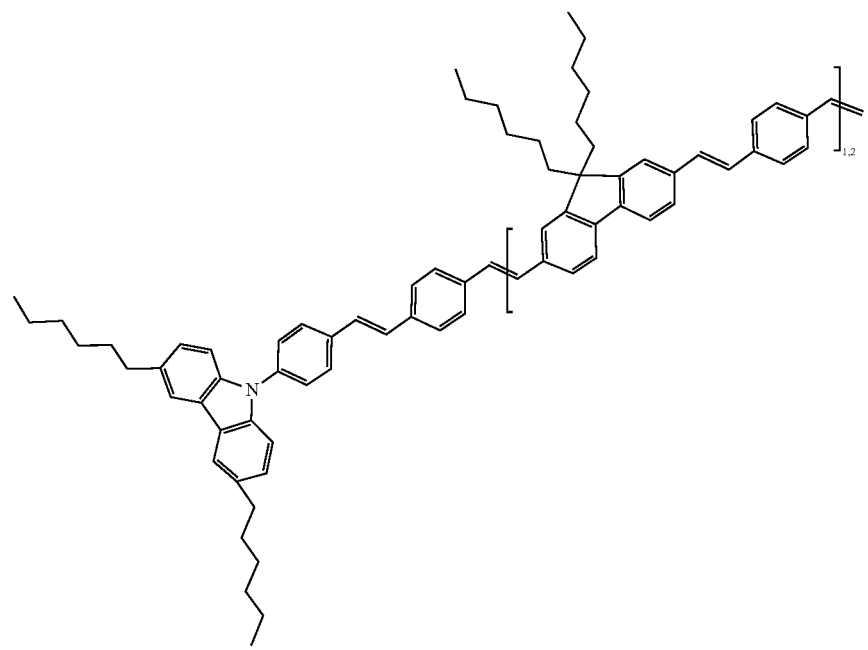

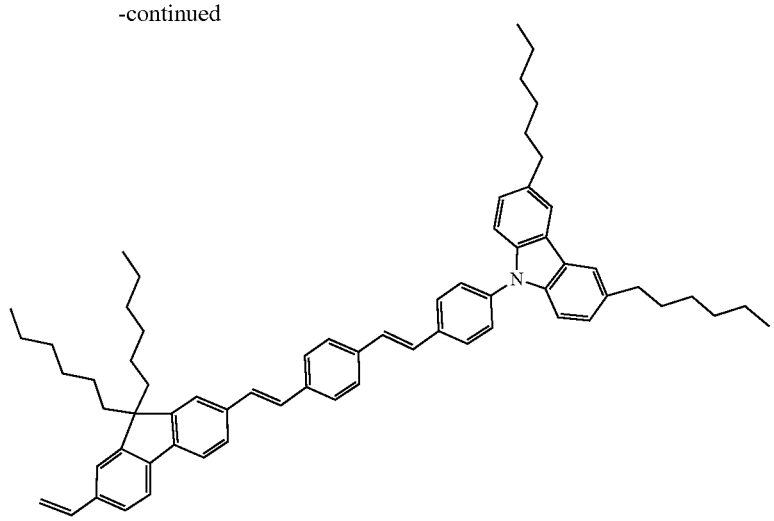

Example 10.1

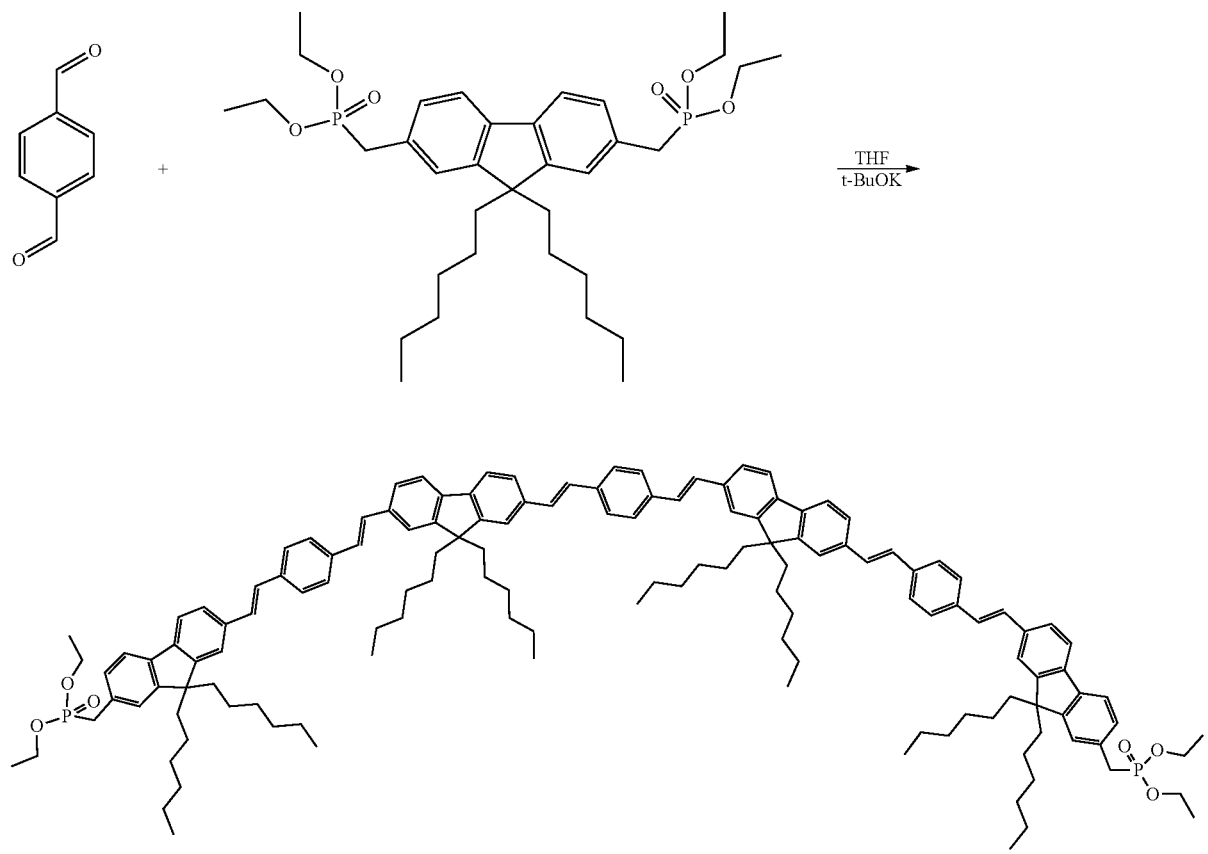

A mixture of 15 mg (0.112 mmol) terephtalaldehyde was reacted with 150 mg (0.224 mmol) 2,7-bis(diethoxyphosphoryl-methyl)-9,9-diehxylfluorene (example 8.1), 27 mg (0.236 mmol) KOtBu and 10 mL of THF at room temperature for 4 hours.

The solvent from the reaction was removed. The residue was worked up with water and dichloromethane. The organic layer was dried and the solvent was removed. After further purification by liquid chromatography with dichloromethane/methanol, 30 mg (13%) of a yellow solid were obtained.

TLC (ethyl acetate:methanol 10:1): $R_f$=between 0.6 and 1.0

Example 10.2
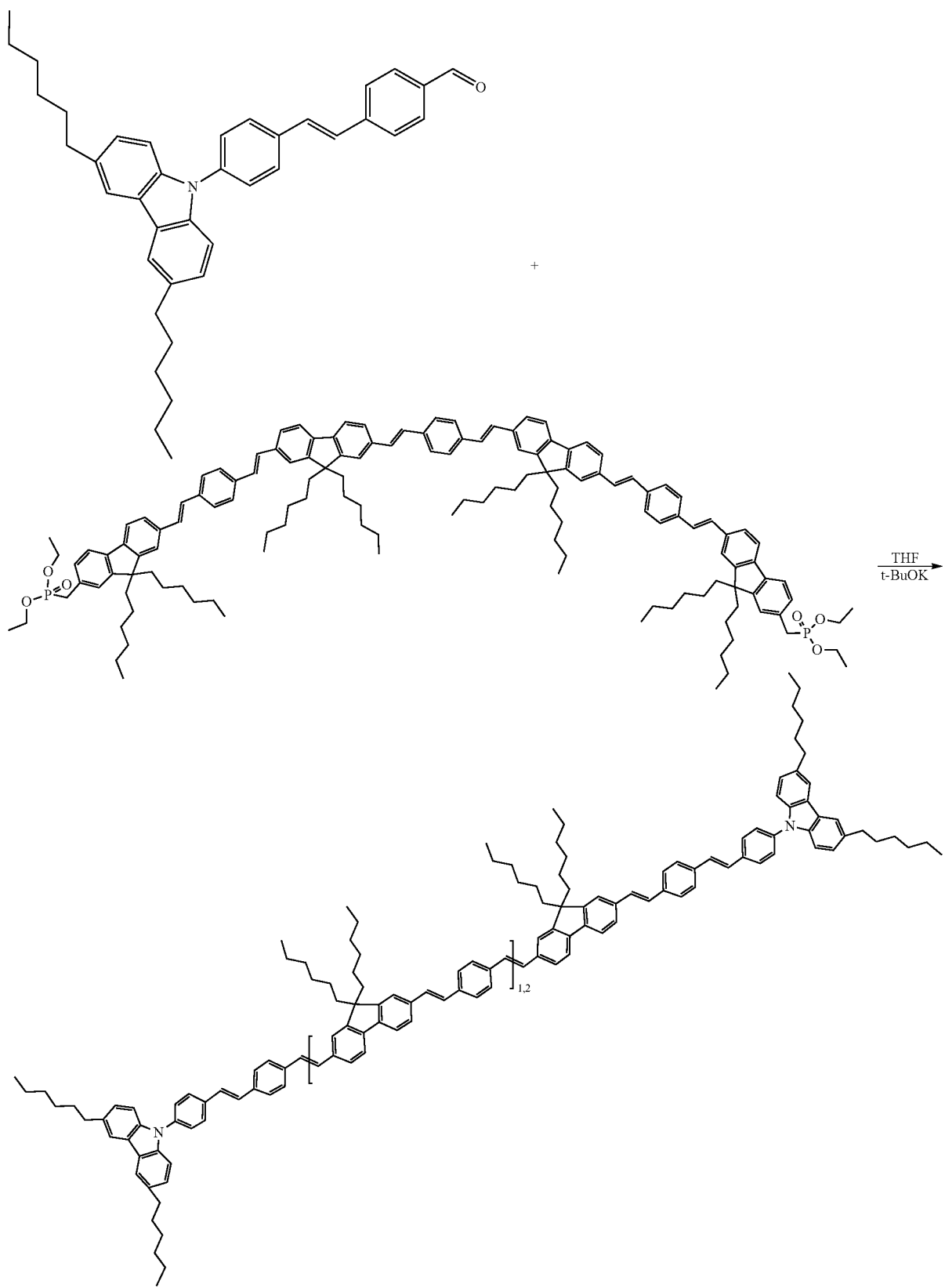

The Wittig Horner Wadsworth Emmons reaction of above-mentioned compound (example 10.1) with 4-[(E)-2-[4-(3,6-dihexylcarbazol-9-yl)phenyl]vinyl]benzaldehyde (example 4.1) was carried out according to example 1.2.

The solvent from the reaction was removed. The residue was worked up with water and dichloromethane. The organic layer was dried and the solvent was removed. After further purification by liquid chromatography with cyclohexane/dichloromethane, the residue was worked up with methanol. 11 mg of a green solid were obtained.

TLC (cyclohexane:dichloromethane 1:1): $R_f$=1

Example 11

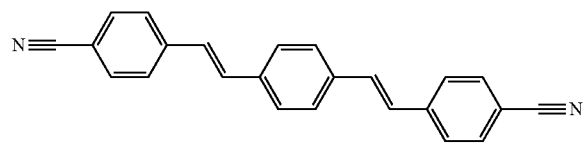

Example 11.1

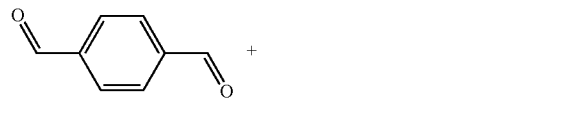

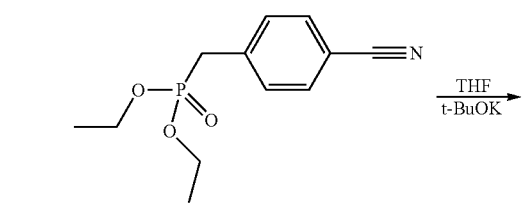

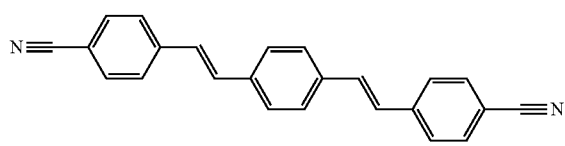 [SMILES: N#Cc1ccc(/C=C/c2ccc(/C=C/c3ccc(C#N)cc3)cc2)cc1]

A mixture of 0.5 g (3.7 mmol) terephthalaldehyde was reacted with 1.98 g (7.75 mmol) 4-cyanobenzyl)-phosphonsäure-diethylester (example 2.1), 0.89 g (7.75 mmol) KOtBu and 40 mL of THF at room temperature for one hour.

The solvent from the reaction mixture was removed. The residue was worked up with dichloromethane and water. The insoluble solid was filtered off. The organic layer was dried and the solvent removed. Both solids were recrystallized with DMF. 0.64 g (52%) of a yellow solid were obtained.

TLC (cyclohexane:dichloromethane 1:3): $R_f$=0.35

Example 12

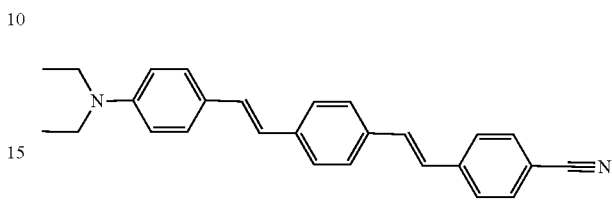

Example 12.1

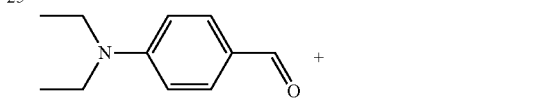

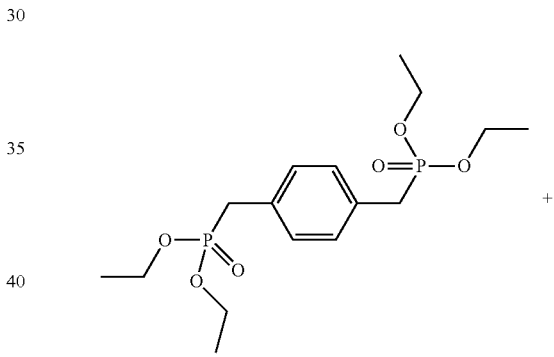

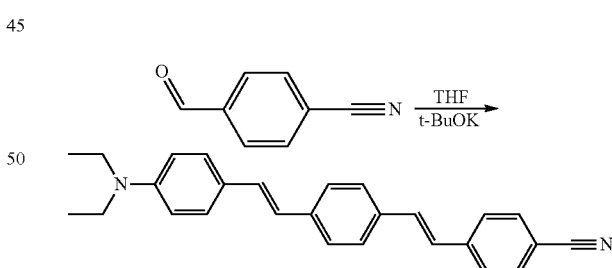

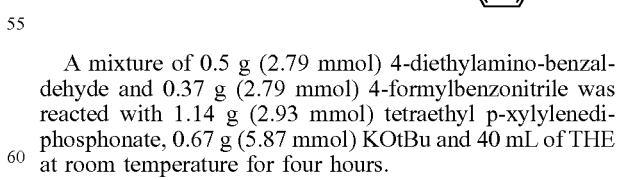

A mixture of 0.5 g (2.79 mmol) 4-diethylamino-benzaldehyde and 0.37 g (2.79 mmol) 4-formylbenzonitrile was reacted with 1.14 g (2.93 mmol) tetraethyl p-xylylenediphosphonate, 0.67 g (5.87 mmol) KOtBu and 40 mL of THF at room temperature for four hours.

The solvent was removed from the reaction mixture. The residue was worked up with dichloromethane and water. The organic layer was dried and the solvent removed. The residue was purified by liquid chromatography with cyclohexane and dichloromethane. 0.22 g (21%) of an orange solid were obtained.

TLC (cyclohexane:dichloromethane 1:3): $R_f$=0.45

Example 13

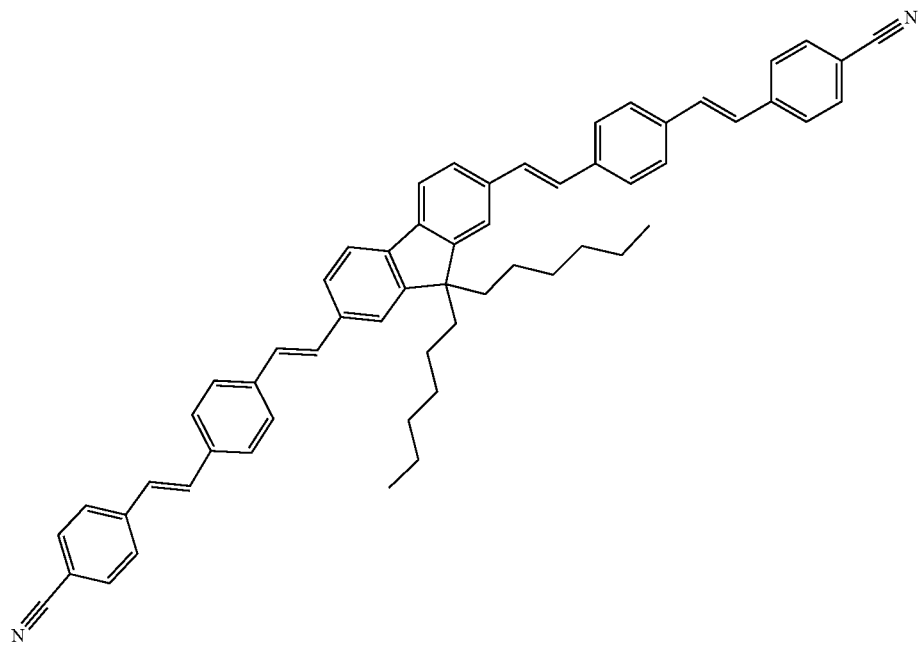 [SMILES: CCCCCCC1(CCCCCC)c2cc(/C=C/c3ccc(/C=C/c4ccc(C#N)cc4)cc3)ccc2-c2ccc(/C=C/c3ccc(/C=C/c4ccc(C#N)cc4)cc3)cc21]

Example 13.1

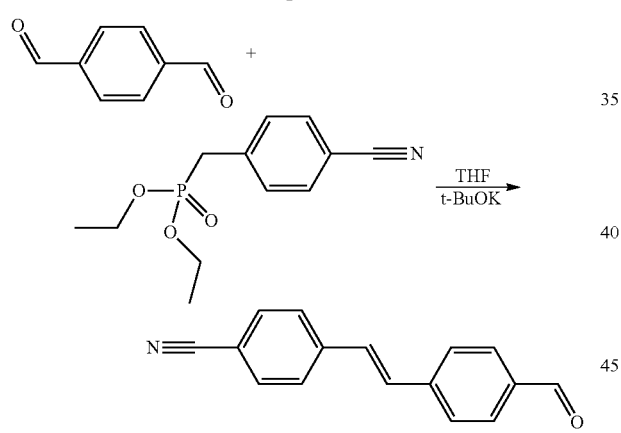

A mixture of 2.00 g (14.76 mmol) terephtalaldehyde was reacted with 3.78 g (14.76 mmol) 4-Cyanobenzyl)-phosphonsäure-diethylester (example 2.1), 1.86 g (16.24 mmol) KOtBu and 50 mL of THF at room temperature for 3 hours.

The solvent from the reaction mixture was removed. The residue was worked up with dichlormethane and water. The organic layer was dried and the solvent removed. After further purification by liquid chromatography with cyclohexane/dichloromethane, 1.59 g (44%) of a yellow solid was obtained.

TLC (cyclohexane:dichloromethane 1:3): $R_f$=0.41

Example 13.2

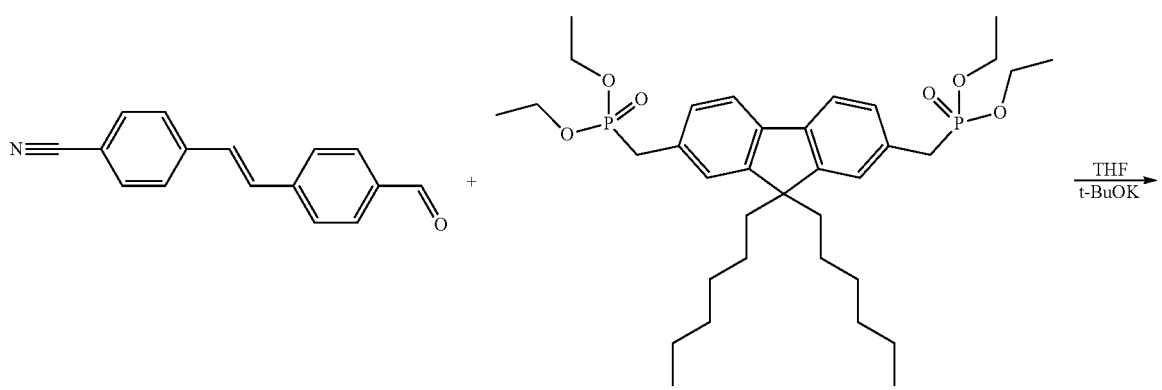

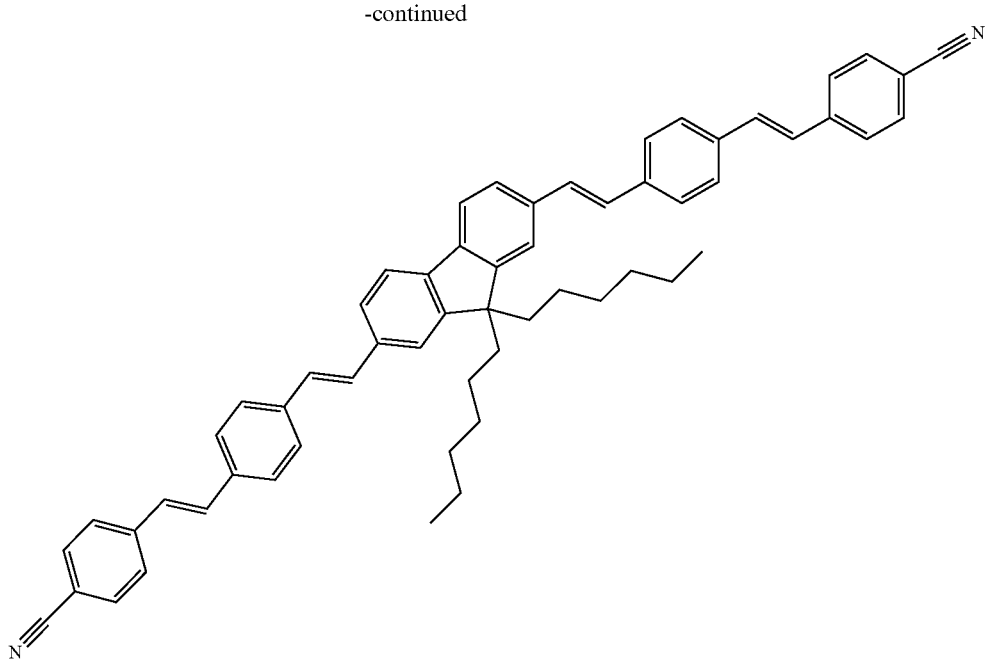

The Wittig Horner Wadsworth Emmons reaction of above-mentioned compound (example 13.1) with 2,7-bis (diethoxyphosphoryl-methyl)-9,9-diehxylfluorene (example 8.1) was carried out according to example 1.2.

The solvent was removed from the reaction mixture. The residue was purified by liquid chromatography with cyclohexane/dichloromethane and washed with methanol. 0.44 g (74%) of a yellow solid were obtained.

TLC (cyclohexane:ethyl acetate:methanol 10:10:1): $R_f=0.93$

Example 14

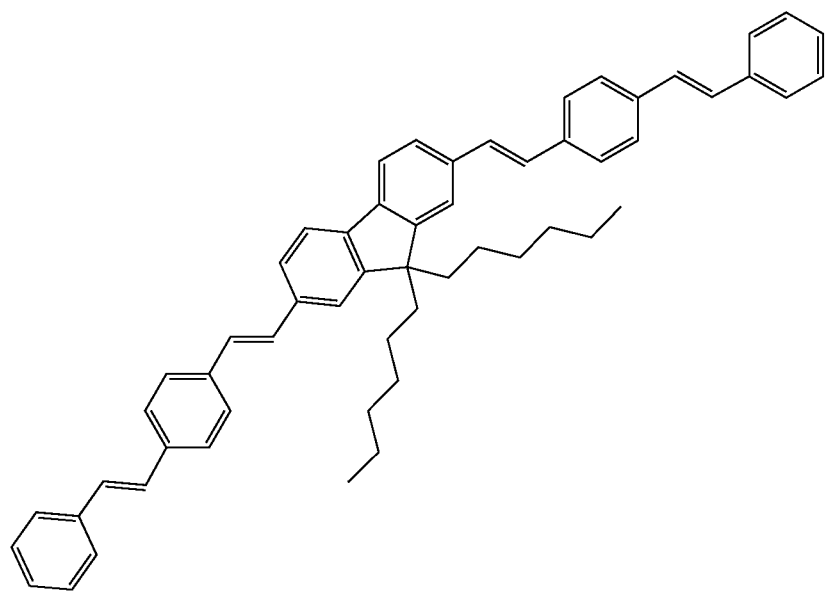 [SMILES: CCCCCCC1(CCCCCC)c2cc(/C=C/c3ccc(/C=C/c4ccccc4)cc3)ccc2-c2ccc(/C=C/c3ccc(/C=C/c4ccccc4)cc3)cc21]

Example 14.1

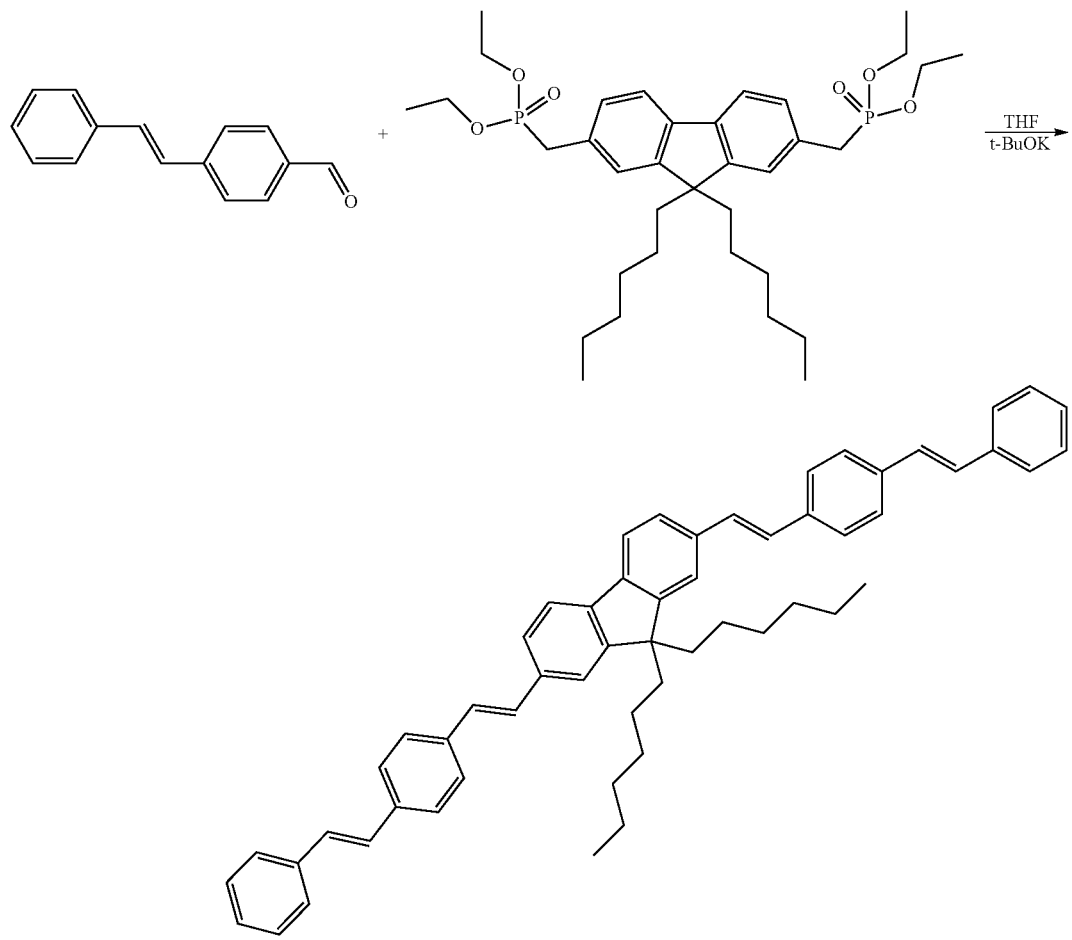

The Wittig Horner Wadsworth Emmons reaction of trans-4-stilbenecarboxaldehyde with 2,7-bis(diethoxyphosphorylmethyl)-9,9-diehxylfluorene (example 8.1) was carried out according to example 1.2.

The solvent was removed from the reaction mixture. The residue was purified by liquid chromatography with cyclohexane/dichloromethane and washed with methanol. 0.5 g (90%) of a yellow solid were obtained.

TLC (cyclohexane:ethyl acetate:methanol 10:10:1): $R_f$=0.96 Properties of the fluorescent dyes (phosphors) of preparation examples 1 to 14
Production of the Films for Testing of the Materials:

The fluorescent dyes synthesized according to the examples were characterized both in solution and in thin film. For the film, they were incorporated as described hereinafter into a matrix composed of a polymer. The polymer used was PMMA (Plexiglas® 6N from Evonik), polystyrene (PS) (PS168 N from BASF), Cyclo Olefin Polymer (Zeonex® from Zeon) and PC (polycarbonate) (Macrolon® 2808 from Covestro).

About 2.5 g of polymer and 0.01%-1% by weight of the dye were dissolved in about 5 mL of methylene chloride, and 0.5% by weight of $TiO_2$ (Kronos 2220) was dispersed therein, based in each case on the amount of polymer used. The solution/dispersion obtained was coated onto a glass surface using an applicator frame (wet film thickness 15-30 μm). After the solvent had dried off, the film was dried for 4 h at 50° C. in vacuum.
Measurement of Quantum Yields Fluorescence quantum yields (QY) of the analysis samples were measured with a Hamamatsu Quantaurus. This was done by illuminating each of the samples with light of 370 nm in an integrating sphere (Ulbricht sphere). By comparison with the reference measurement in the Ulbricht sphere without sample, the unabsorbed fraction of the excitation light and the fluorescent light emitted by the sample are determined by means of a CCD spectrometer. Integration of the intensities of the spectrum of the unabsorbed excitation light and of that of the emitted fluorescent light gives the degree of absorption and fluorescence intensity, respectively and thus the fluorescence quantum yield of each sample can be calculated.

Determination of the Excited-State Lifetime $\tau_v$ and the Emissive Lifetime $\tau_0$ The excited-state lifetime ($\tau_v$) of the prepared thin films is measured by exciting the thin films with a pulsed diode laser with an excitation wavelength of 370 nm (Picoquant) operated at 10 MHz and detecting the emission with time correlated single photon counting (TCSPC). A mono-exponential or bi-exponential fit to the decay curve was used to determine the excited-state lifetime ($\tau_v$).

$$I(t) = \sum_{i=1}^{j} a_i e^{\left(-\frac{t}{\tau_i}\right)}$$

For a bi-exponential fit the average lifetime was calculated according to the following equation.

$$\tau_v = \frac{a_1 \tau_1^2 + a_2 \tau_2^2}{a_1 \tau_1 + a_2 \tau_2}$$

The emissive lifetime $\tau_0$ is calculated by $\tau_0 = \tau_v / QY$.

The following table summarizes the results. The decay rate was determined at the emission maximum. Some of the materials were measured in different matrices, and some samples were also measured without adding $TiO_2$ into the film to see the influence of the scatterer.

| Example | Dye | matrix/solution | $\lambda_{max}^{4)}$ [nm] | QY[1] [%] | $\tau_V^{2)}$ [ns] | $\tau_0^{3)}$ [ns] |
|---|---|---|---|---|---|---|
| 5 | (structure) | PC | 535 | 6 | | |
| | | Chloroform | 471 | 83 | | |
| | | DCM[6] | 516 | 62 | | |
| 6 | (structure) | PC | 491 | 79 | 1.48 | 1.87 |
| 7 | (structure) | DCM | 488 | 61 | | |

-continued
| Example | Dye | matrix/ solution | $\lambda_{max}^{4)}$ [nm] | $QY^{1)}$ [%] | $\tau_V^{2)}$ [ns] | $\tau_0^{3)}$ [ns] |
|---|---|---|---|---|---|---|
| 8 | 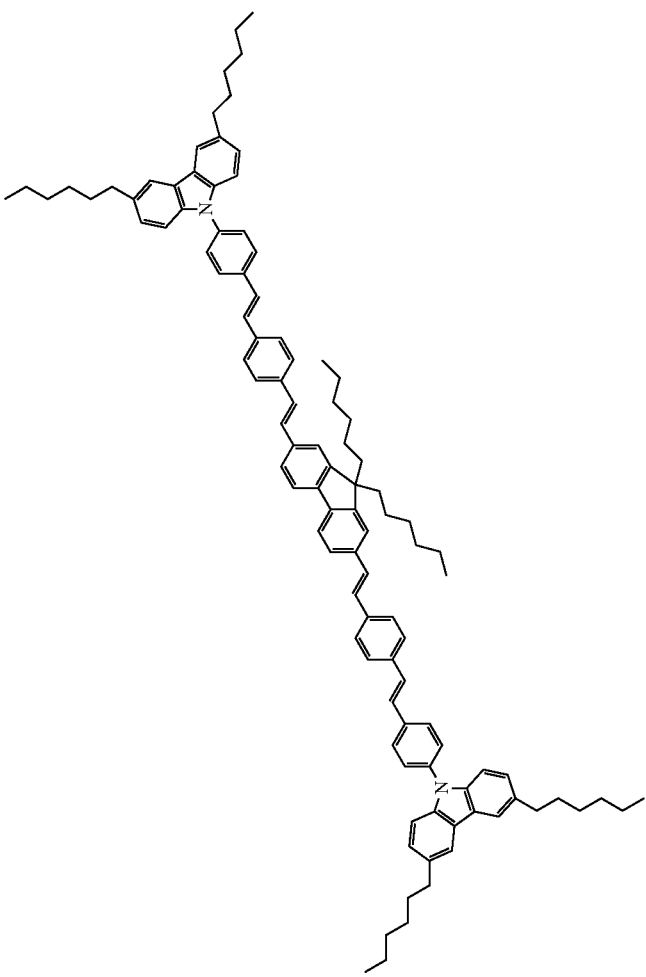 | PS | 491 | 94 | 1.34 | 1.42 |
| | | DCM | 485 | 87 | | |

-continued
| Example | Dye | matrix/ solution | λ_max[4] [nm] | QY[1] [%] | τ_V[2] [ns] | τ_0[3] [ns] |
|---|---|---|---|---|---|---|
| 9 | 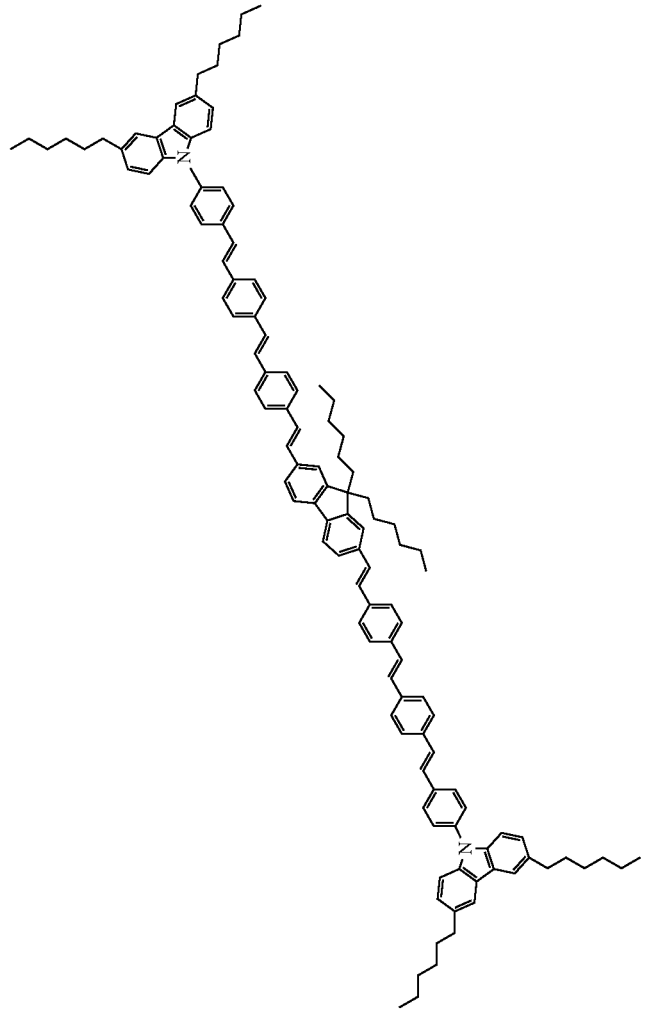 | PS | 514 | 76 | 1.49 | 1.96 |
| | | DCM | 472 | 90 | | |

-continued

| Example | Dye | matrix/ solution | $\lambda_{max}^{4)}$ [nm] | QY[1] [%] | $\tau_V^{2)}$ [ns] | $\tau_0^{3)}$ [ns] |
|---|---|---|---|---|---|---|
| 11 | (4-cyanophenyl–CH=CH–phenyl–CH=CH–4-cyanophenyl) | DCM | 436 | 60 | 1.38 | 2.29 |
| 12 | (4-cyanophenyl–CH=CH–phenyl–CH=CH–4-(diethylamino)phenyl) | PC | 540 | 81 | 1.92 | 2.37 |

[1] Fluorescence quantum yield
[2] Excited-state lifetime
[3] Emissive lifetime
[4] Emission maximum of the dye
[5] PS w/o TiO$_2$: Polystyrene without TiO$_2$
[6] DCM: dichloromethane As the TCSPC is not able to measure decay times around or below 1 ns accurately, a streak camera was used for more precise time-resolved measurements below 1 ns. A Hamamatsu Universal Streak Camera C10910 with Acton SpectraPro SP2300 spectrometer was used. Excitation pulses at 400 nm were generated from the second harmonic of the output of a Coherent Chameleon Ti:Sapphire oscillator and the streak camera was operated in the sychroscan mode.

| Example | Dye | matrix/solution | $\lambda_{max}^{4)}$ [nm] | $QY^{1)}$ [%] | $\tau_{V}^{2)}$ [ns] | $\tau_{0}^{3)}$ [ns] |
|---|---|---|---|---|---|---|
| 1C | 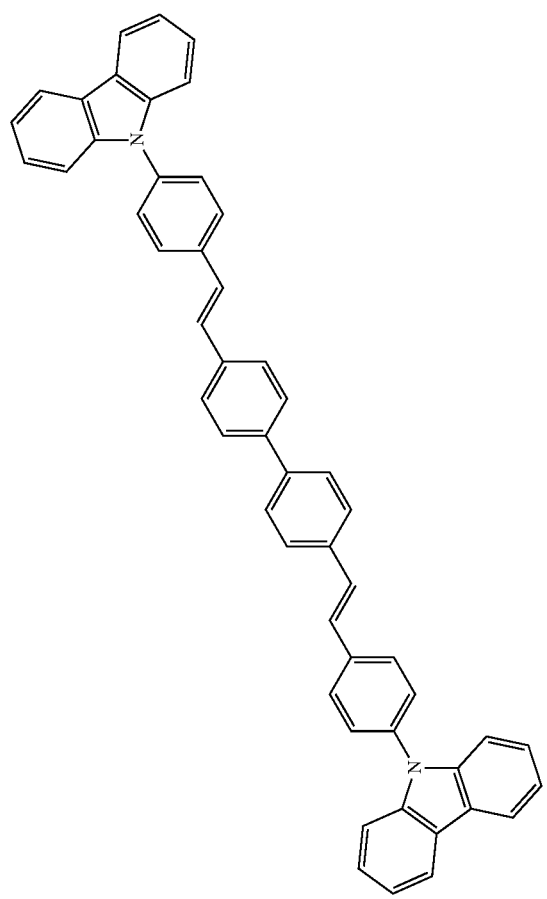<br>(BSBCz) | PS | 448 | 76 | 0.70 | 0.934 |

-continued

| Example | Dye | matrix/solution | $\lambda_{max}$[4] [nm] | QY[1] [%] | $\tau_v$[2] [ns] | $\tau_0$[3] [ns] |
|---|---|---|---|---|---|---|
| 2 | (structure shown) | PS w/o TiO$_2$[5] | 512 | 46 | 0.61 | 1.33 |
| | | PS | | 37 | 0.41 | 1.10 |
| | | Zeonex® | | 50 | 0.43 | 0.85 |

-continued
| Example | Dye | matrix/solution | $\lambda_{max}^{4)}$ [nm] | $QY^{1)}$ [%] | $\tau_V^{2)}$ [ns] | $\tau_0^{3)}$ [ns] |
|---|---|---|---|---|---|---|
| 3 | 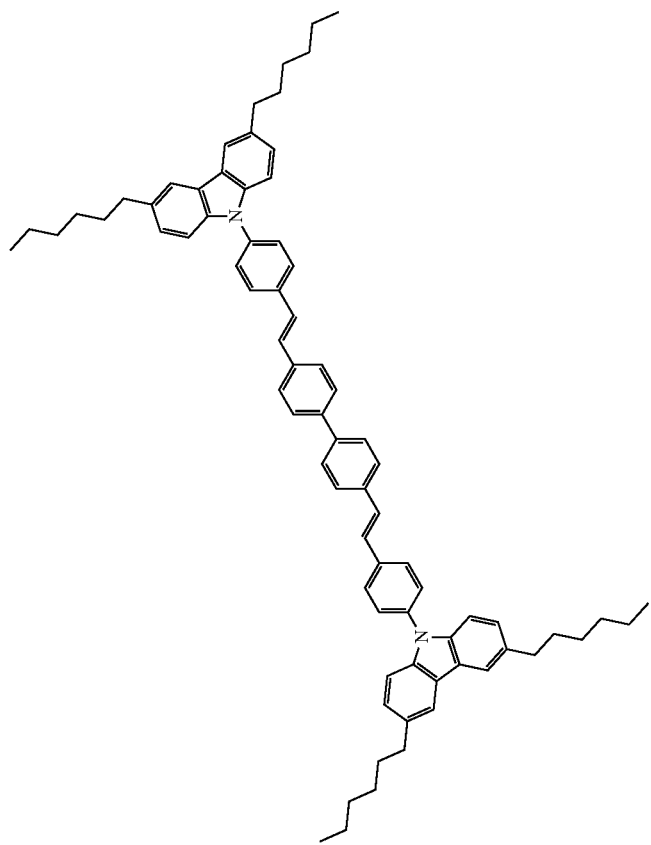 | PC | 452 | 96 | 0.77 | 0.80 |

-continued
| Example | Dye | matrix/solution | $\lambda_{max}$[4] [nm] | $QY$[1] [%] | $\tau_F$[2] [ns] | $\tau_0$[3] [ns] |
|---|---|---|---|---|---|---|
| 4 | 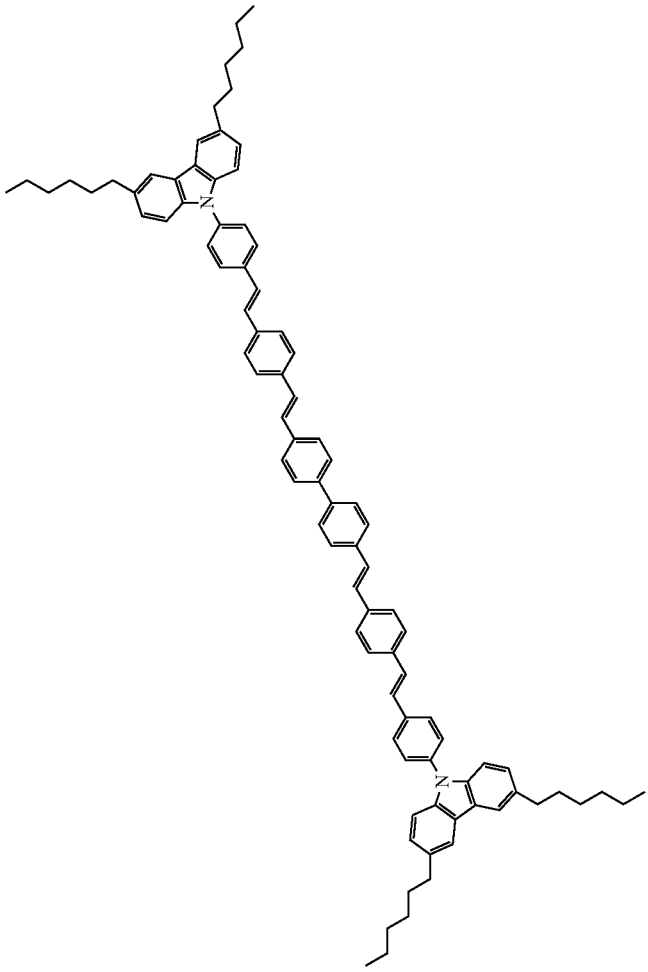 | PS | 509 | 45 | 0.43 | 0.96 |
| 6 | 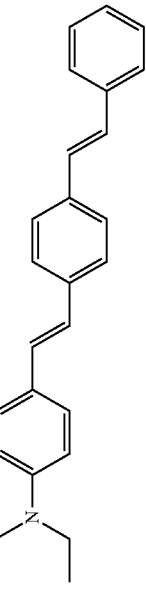 | PC | 486 | 78 | 0.98 | 1.25 |

-continued
| Example | Dye | matrix/solution | $\lambda_{max}^{4)}$ [nm] | $QY^{1)}$ [%] | $\tau_v^{2)}$ [ns] | $\tau_0^{3)}$ [ns] |
|---|---|---|---|---|---|---|
| 8 | 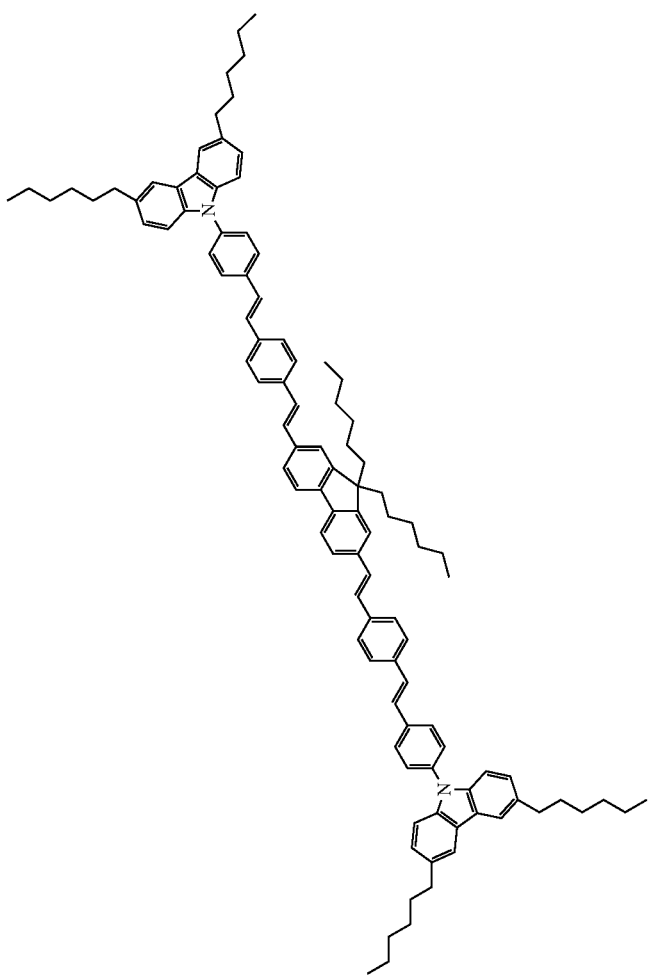 | PC | 489 | 89 | 0.63 | 0.71 |

-continued

| Example | Dye | matrix/solution | $\lambda_{max}^{4)}$ [nm] | $QY^{1)}$ [%] | $\tau_v^{2)}$ [ns] | $\tau_0^{3)}$ [ns] |
|---|---|---|---|---|---|---|
| 9 |  | PC | 496 | 56 | 0.63 | 1.13 |

-continued
| Example | Dye | matrix/solution | $\lambda_{max}^{4)}$ [nm] | $QY^{1)}$ [%] | $\tau_F^{2)}$ [ns] | $\tau_0^{3)}$ [ns] |
|---|---|---|---|---|---|---|
| 10 | 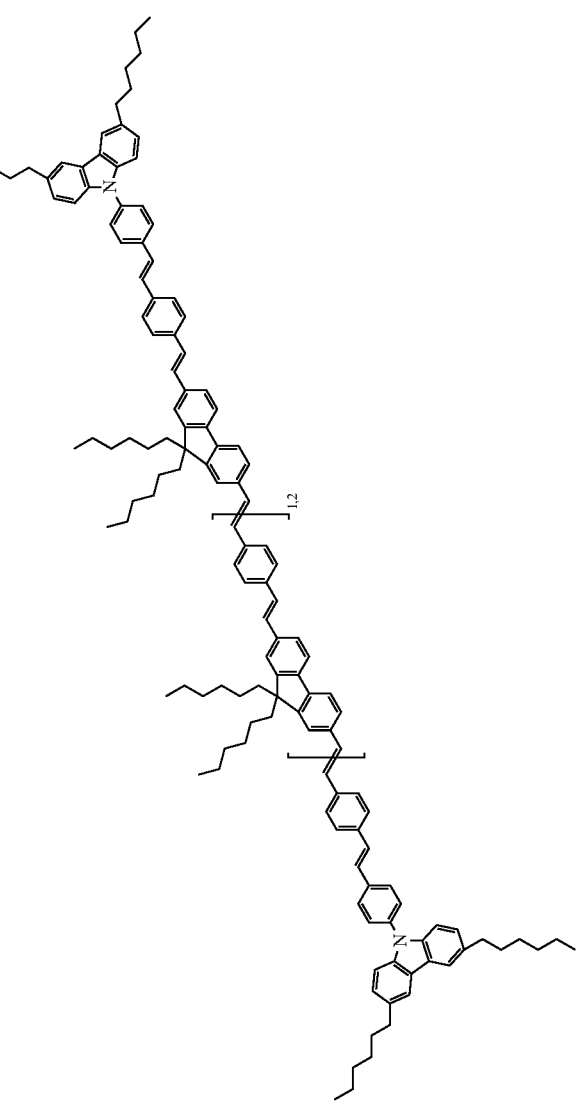 | PC | 506 | 75 | 0.55 | 0.73 |
| 11 | 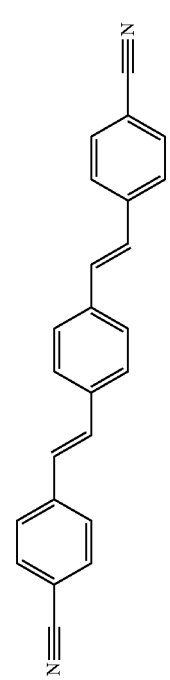 | PC | 440 | 90 | 0.74 | 0.82 |

-continued

| Example | Dye | matrix/solution | $\lambda_{max}$[4] [nm] | QY[1] [%] | $\tau_V$[2] [ns] | $\tau_0$[3] [ns] |
|---|---|---|---|---|---|---|
| 13 | (structure) | PC | 495 | 97 | 0.60 | 0.62 |
| 14 | (structure) | PC | 481 | 98 | 0.57 | 0.58 |

[1] Fluorescence quantum yield
[2] Excited-state lifetime
[3] Emissive lifetime
[4] Emission maximum of the dye
[5] PS w/o TiO$_2$: Polystyrene without TiO$_2$
[6] DCM: dichloromethane

The invention claimed is:

1. Optical data communication system, comprising:
a transmitter comprising a digital signal processor with a digital-to-analog converter, which is configured to modulate digital information bits (input) and their transformation into an analog current signal, and a light source, wherein when the input is already an analog signal, conversion of the signal to an analog signal is omitted, the light source being a phosphor converted LED, wherein light is generated based on a color converter and an LED; and
a receiver,
wherein the color converter compound of formula (I)

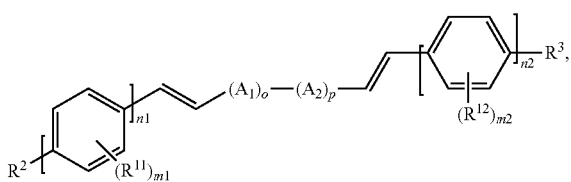

(I)

wherein
n1 and n2 are independently 1, 2, or 3,
m1 and m2 are independently 0, 1, 2, 3, or 4,
$R^{11}$ and $R^{12}$ are independently H, $C_1$-$C_{20}$alkyl, $C_1$-$C_{20}$alkoxy, $C_6$-$C_{30}$aryl, or $C_7$-$C_{31}$alkaryl,
$R^2$ and $R^3$ are independently H, $C_1$-$C_{20}$alkyl, $C_2$-$C_{20}$alkenyl, $C_1$-$C_{20}$alkoxy, $C_3$-$C_{20}$cycloalkyl, $C_6$-$C_{24}$aryl, aliphatic heterocycle comprising a ring formed of 3 to 24 atoms; heteroaryl comprising a ring formed of 3 to 24 atoms, amino, CN, $CF_3$, $COOC_1$-$C_{20}$alkyl, $OCOC_1$-$C_{20}$alkyl, or $C_7$-$C_{31}$ alkaryl,
$A_2$ is

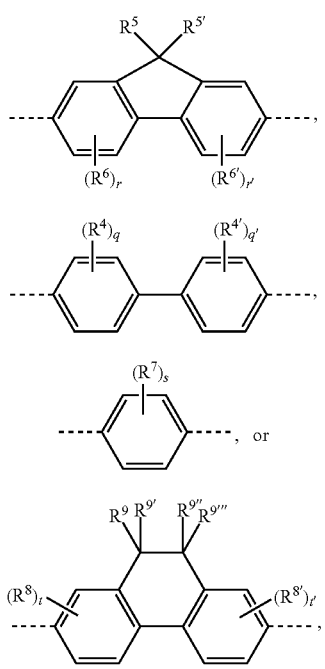

$A_1$ is

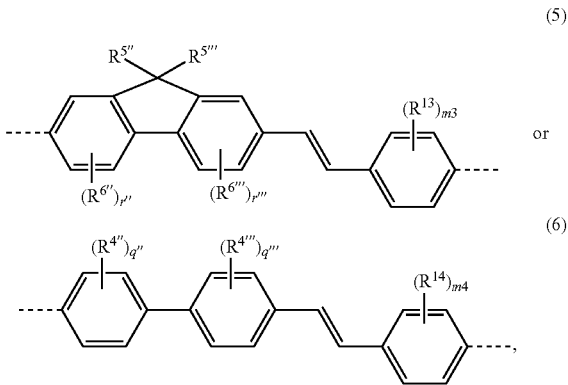

p is 1 or 2,
o is 0, 1 or 2,
q, q', q", q'", s, m3, and m4 are independently 0, 1, 2, 3, or 4,
r, r', r", r'", t, and t' are independently 0, 1, 2, or 3,
$R^4$, $R^{4'}$, $R^{4''}$, $R^{4'''}$, $R^6$, $R^{6'}$, $R^{6''}$, $R^{6'''}$, $R^7$, $R^8$, $R^{8'}$, $R^{13}$, and $R^{14}$ are independently H, $C_1$-$C_{20}$alkyl, $C_1$-$C_{20}$alkoxy, $C_6$-$C_{30}$aryl, or $C_7$-$C_{31}$alkaryl,
$R^5$, $R^{5'}$, $R^{5''}$, $R^{5'''}$, $R^9$, $R^{9'}$, $R^{9''}$, and $R^{9'''}$ are independently H, $C_1$-$C_{20}$alkyl, $C_6$-$C_{30}$aryl, or $C_7$-$C_{31}$alkaryl,
wherein the dotted lines are bonding sites.

2. The system of claim 1, wherein
$R^2$ and $R^3$ are independently H,

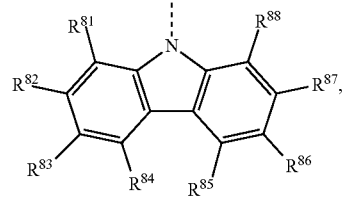

$C_1$-$C_8$alkylamino, $C_6$-$C_{10}$arylamino, CN, $CF_3$, or $COO(C_1$-$C_8)$alkyl,

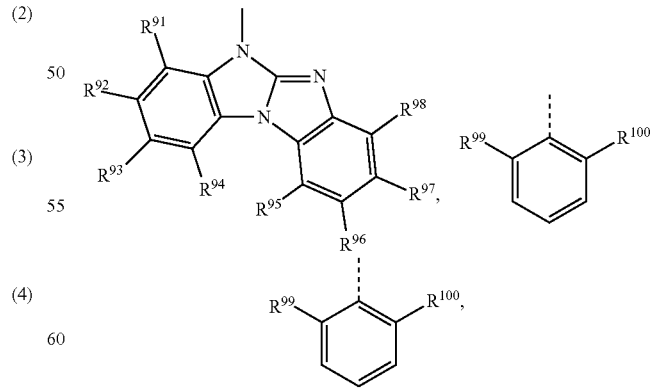

wherein
$R^{81}$, $R^{82}$, $R^{83}$, $R^{84}$, $R^{85}$, $R^{86}$, $R^{87}$, and $R^{88}$ are independently H, $C_1$-$C_{20}$alkyl, $C_1$-$C_{20}$alkoxy, $C_6$-$C_{30}$aryl, or $C_7$-$C_{31}$ alkaryl, $R^{91}$, $R^{92}$, $R^{93}$, $R^{94}$, $R^{95}$, $R^{96}$, $R^{97}$, and $R^{98}$ are independently H, $C_1$-$C_{20}$alkyl, $C_1$-$C_{20}$alkoxy, $C_6$-$C_{30}$aryl, or $C_7$-$C_{31}$ alkaryl, $R^{99}$ and $R^{100}$ are independently H, $C_1$-$C_{20}$alkyl, $C_1$-$C_{20}$alkoxy, $C_6$-$C_{30}$aryl, or $C_7$-$C_{31}$ alkaryl, wherein the dotted lines are bonding sites.

3. The system according to claim 2, wherein $R^2$ and $R^3$ are independently H,

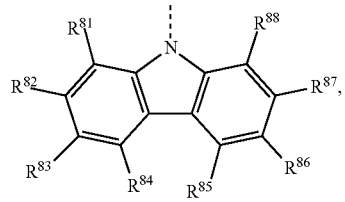

$CF_3$, or CN,
wherein
$R^{81}$, $R^{82}$, $R^{83}$, $R^{84}$, $R^{85}$, $R^{86}$, $R^{87}$, and $R^{88}$ are independently H, $C_1$-$C_{20}$alkyl, $C_1$-$C_{20}$alkoxy, $C_6$-$C_{30}$aryl, or $C_7$-$C_{31}$ alkaryl.

4. The system of claim 3, wherein
$R^{81}$, $R^{82}$, $R^{84}$, $R^{85}$, $R^{87}$, and $R^{88}$ are H, and
$R^{83}$ and $R^{86}$ are $C_1$-$C_{20}$alkyl.

5. The system of claim 3, wherein
$R^{81}$, $R^{82}$, $R^{84}$, $R^{85}$, $R^{87}$, and $R^{88}$ are H, and
$R^{83}$ and $R^{86}$ are $C_3$-$C_8$alkyl.

6. The system of claim 1, wherein $A_1$ is

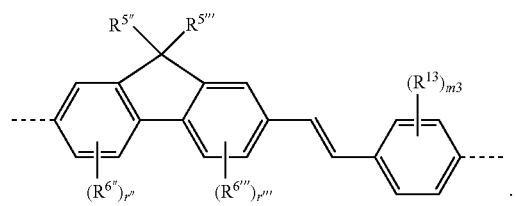
(4)

7. The system of claim 1, wherein o is 0.
8. The system of claim 1, wherein $A_2$ is

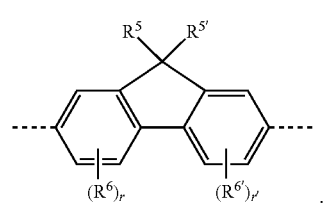
(I)

9. The system of claim 1, wherein $R^5$, $R^{5\prime}$, $R^{5\prime\prime}$ and $R^{5\prime\prime\prime}$ are independently $C_1$-$C_{20}$alkyl, $C_6$-$C_{30}$aryl, or $C_7$-$C_{31}$alkaryl.

10. The system of claim 1, wherein
p is 1;
o is 0;
n1 and n2 are independently 1 or 2;
q, q', q", q''', s, m3, and m4 are 0;
r, r', r", and r''' are 0.

11. The system of claim 1, comprising:
a compound of formula (Ia)

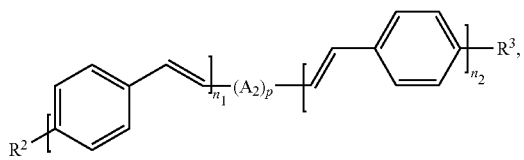
(Ia)

wherein
n1 and n2 are independently 1 or 2,
$R^2$ and $R^3$ are independently H,

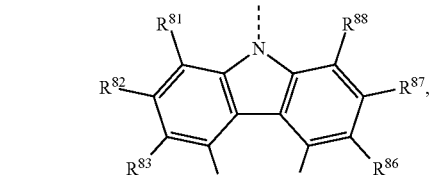

$CF_3$, or CN,
wherein
$R^{81}$, $R^{82}$, $R^{83}$, $R^{84}$, $R^{85}$, $R^{86}$, $R^{87}$, and $R^{88}$ are independently H, $C_1$-$C_{20}$alkyl, $C_1$-$C_{20}$alkoxy, $C_6$-$C_{30}$aryl, or $C_7$-$C_{31}$ alkaryl, $A_2$ is

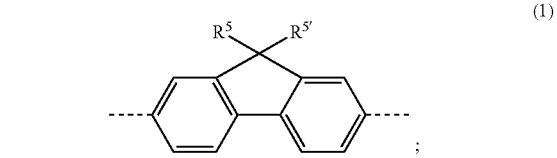
(1)

p is 1,
$R^5$ and $R^{5\prime}$ are independently $C_1$-$C_{20}$alkyl, $C_6$-$C_{30}$aryl, or $C_7$-$C_{31}$alkaryl,
wherein the dotted lines are bonding sites.

12. The system of claim 1, which is a free space optical data communication system.

13. A compound of formula (I*)

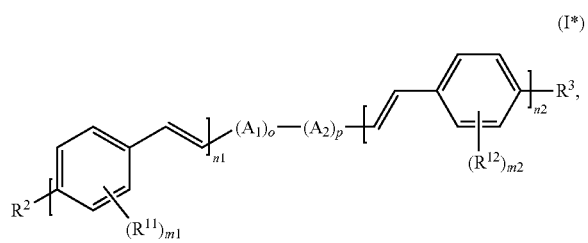
(I*)

wherein
n1 and n2 are 2,
$R^2$ and $R^3$ are each independently hydrogen,

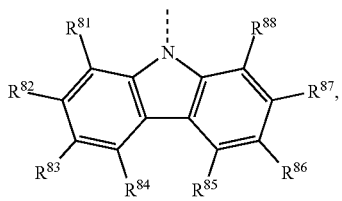

CF₃, or CN, $R^{81}$, $R^{82}$, $R^{83}$, $R^{84}$, $R^{85}$, $R^{86}$, $R^{87}$, $R^{88}$ are each independently hydrogen or unsubstituted or substituted $C_1$-$C_{20}$alkyl, unsubstituted or substituted $C_1$-$C_{20}$alkoxy, unsubstituted or substituted $C_6$-$C_{30}$aryl or unsubstituted or substituted $C_7$-$C_{31}$alkaryl, $A_2$ is,

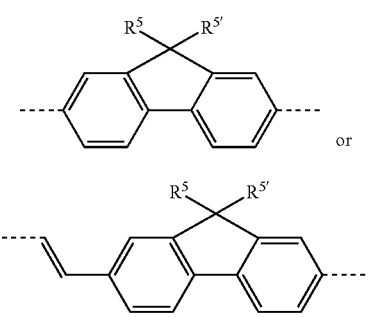

(1)

or (1')

p is 1, $R^5$ and $R^{5'}$ are unsubstituted or substituted $C_1$-$C_{20}$ alkyl;

wherein the dotted lines are bonding sites.

14. A process for preparing the compound of claim 13, the process comprising:

(i) coupling a group of formula (II*)

   (II*)

with a group of formula (III*) and a group of formula (IV*)

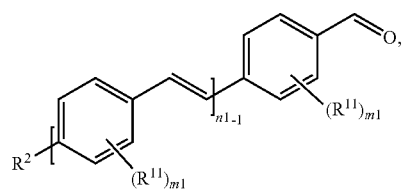   (III*)

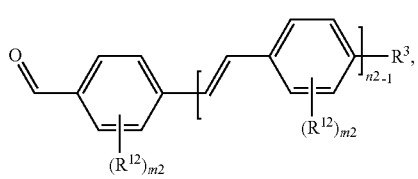   (IV*)

wherein

X and X' are independently a phosphonic acid ester group (V)

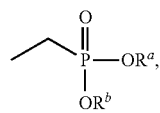   (V)

wherein $R^a$ and $R^b$ are independently unsubstituted or substituted $C_1$-$C_{20}$alkyl, n1 and n2 are 2, $R^{11}$ and $R^{12}$ are H, $R^2$ and $R^3$ are independently H

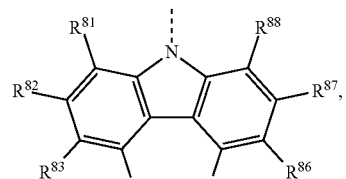

CF₃, or CN, $R^{81}$, $R^{82}$, $R^{83}$, $R^{84}$, $R^{85}$, $R^{86}$, $R^{87}$, $R^{88}$ are each independently hydrogen or unsubstituted or substituted $C_1$-$C_{20}$alkyl, unsubstituted or substituted $C_1$-$C_{20}$alkoxy, unsubstituted or substituted $C_6$-$C_{30}$aryl or unsubstituted or substituted $C_7$-$C_{31}$alkaryl, $A_2$ is,

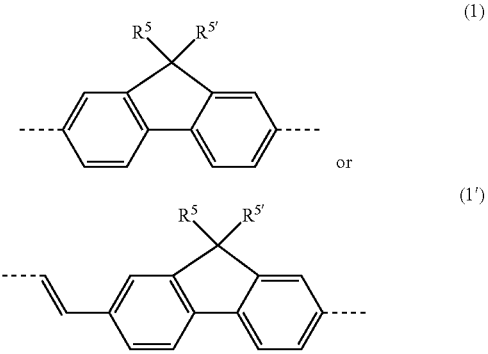

(1)

or (1')

p is 1, $R^5$ and $R^{5'}$ are unsubstituted or substituted $C_1$-$C_{20}$ alkyl, wherein the dotted lines are bonding sites.

15. A receiver, comprising:

a wavelength shifting material and a detector in a combined system, wherein the wavelength shifting material comprises a compound of formula (I)

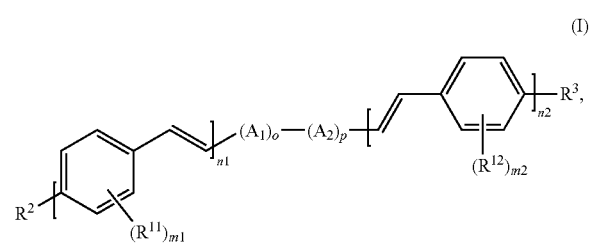   (I)

wherein n1 and n2 are independently 1, 2, or 3, m1 and m2 are independently 0, 1, 2, 3, or 4, $R^{11}$ and $R^{12}$ are independently H, $C_1$-$C_{20}$alkyl, $C_1$-$C_{20}$alkoxy, $C_6$-$C_{30}$aryl, or $C_7$-$C_{31}$alkaryl, $R^2$ and $R^3$ are independently H, $C_1$-$C_{20}$alkyl, $C_2$-$C_{20}$alkenyl, $C_1$-$C_{20}$alkoxy, $C_3$-$C_{20}$cycloalkyl, $C_6$-$C_{24}$aryl, aliphatic heterocycle comprising a ring formed of 3 to 24 atoms; heteroaryl comprising a ring formed of 3 to 24 atoms, amino, CN, $CF_3$, $COOC_1$-$C_{20}$alkyl, $OCOC_1$-$C_{20}$alkyl, or $C_7$-$C_{31}$alkaryl, $A_2$ is

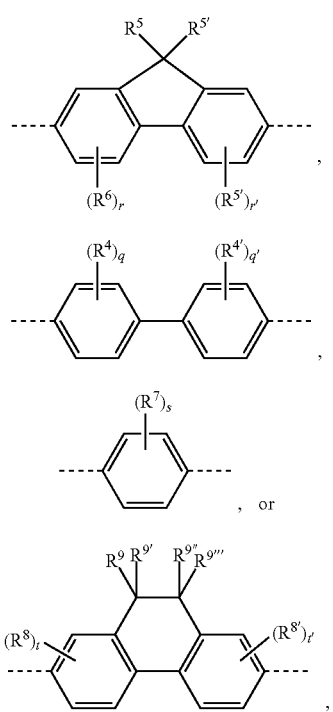

(1)

(2)

(3)

(4)

, or $A_1$ is

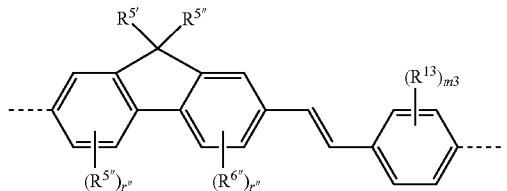

(5)

or

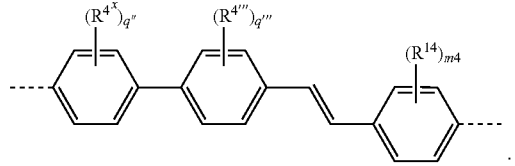

(6)

p is 1 or 2, is 0, 1 or 2, q, q', q", q''', s, m3, and m4 are independently 0, 1, 2, 3, or 4, r, r', r", r''''', t, and t' are independently 0, 1, 2, or 3, $R^4$, $R^{4\prime}$, $R^{4\prime\prime}$, $R^{4\prime\prime\prime}$, $R^6$, $R^{6\prime}$, $R^{6\prime\prime}$, $R^{6\prime\prime\prime}$, $R^7$, $R^8$, $R^{8\prime}$, $R^{13}$, and $R^{14}$ are independently H, $C_1$-$C_{20}$alkyl, $C_1$-$C_{20}$alkoxy, $C_6$-$C_{30}$aryl, or $C_7$-$C_{31}$alkaryl, $R^5$, $R^{5\prime}$, $R^{5\prime\prime}$, $R^{5\prime\prime\prime}$, $R^9$, $R^{9\prime}$, $R^{9\prime\prime}$, and $R^{9\prime\prime\prime}$ are independently H, $C_1$-$C_{20}$alkyl, $C_6$-$C_{30}$aryl, or $C_7$-$C_{31}$alkaryl, wherein the dotted lines are bonding sites.

16. An optical data communication system, comprising:

a transmitter, and the receiver of claim 15.

17. A method of making an optical data communication system, the method comprising:

contacting the compound of claim 13 with a component of the optical data communication system.

* * * * *